US011793574B2

(12) United States Patent
Hill et al.

(10) Patent No.: US 11,793,574 B2
(45) Date of Patent: Oct. 24, 2023

(54) AUTOMATED CUT PLANNING FOR REMOVAL OF DISEASED REGIONS

(71) Applicant: Stryker Australia PTY LTD, Artarmon (AU)

(72) Inventors: David Gibson Hill, Heathmont (AU); Tom Michael Williamson, Brunswick (AU); Chow Yin Lai, London (GB)

(73) Assignee: STRYKER AUSTRALIA PTY LTD, Artarmon Nsw (AU)

( * ) Notice: Subject to any disclaimer, the term of this patent is extended or adjusted under 35 U.S.C. 154(b) by 67 days.

(21) Appl. No.: 17/201,479

(22) Filed: Mar. 15, 2021

(65) Prior Publication Data

US 2021/0282858 A1  Sep. 16, 2021

Related U.S. Application Data

(60) Provisional application No. 62/990,038, filed on Mar. 16, 2020.

(51) Int. Cl.
*A61B 34/10* (2016.01)
*G16H 20/40* (2018.01)
(Continued)

(52) U.S. Cl.
CPC ............. *A61B 34/10* (2016.02); *G16H 20/40* (2018.01); *G16H 50/50* (2018.01); *A61B 34/30* (2016.02);
(Continued)

(58) Field of Classification Search
CPC .............. A61B 34/10; A61B 2034/105; A61B 2034/107; G16H 20/40; G16H 50/50
See application file for complete search history.

(56) References Cited

U.S. PATENT DOCUMENTS 6,711,432 B1   3/2004 Krause et al.
7,203,277 B2   4/2007 Birkenbach et al.
(Continued)

FOREIGN PATENT DOCUMENTS

WO   2005078666 A1   8/2005
WO   2006056614 A1   6/2006
(Continued)

OTHER PUBLICATIONS

Bian, Q., Zhang, X., Wang, Z., Liu, M., Li, B., Wu, D., & Liu, G. (Jan. 9, 2020). Virtual surgery system for liver tumor resection. Journal of Intelligent & Fuzzy Systems, 38(1), 263-276. (Year: 2020).*

(Continued)

*Primary Examiner* — Bijan Mapar
(74) *Attorney, Agent, or Firm* — Howard & Howard Attorneys PLLC

(57) ABSTRACT

Systems, computer-implemented methods, and computer program products are provided for automated planning of a cutting boundary for removal of a diseased region of an anatomy, such as a bone tumor. A model is provided for the diseased region of the anatomy, and optionally, a healthy region of the anatomy. One or more cutting geometries are defined relative the diseased region. Algorithms are provided which enable automated optimization of characteristics (e.g., shape, size, position, orientation) of the cutting geometries relative to the diseased region in order to plan for complete removal of the diseased region, en bloc, while minimizing an amount of healthy region to be removed.

16 Claims, 17 Drawing Sheets

(51) Int. Cl.
  *G16H 50/50* (2018.01)
  *A61B 34/20* (2016.01)
  *A61B 34/30* (2016.01)

(52) U.S. Cl.
  CPC ... *A61B 2034/105* (2016.02); *A61B 2034/107* (2016.02); *A61B 2034/2055* (2016.02)

(56) References Cited

U.S. PATENT DOCUMENTS

| | | | |
|---|---|---|---|
| 7,725,162 | B2 | 5/2010 | Malackowski et al. |
| 7,831,292 | B2 | 11/2010 | Quaid et al. |
| 8,010,180 | B2 | 8/2011 | Quaid et al. |
| 8,477,153 | B2 | 7/2013 | Lin et al. |
| 8,660,325 | B2 | 2/2014 | Kaus et al. |
| 8,675,939 | B2 | 3/2014 | Moctezuma de la Barrera |
| 8,977,021 | B2 | 3/2015 | Kang et al. |
| 9,008,757 | B2 | 4/2015 | Wu |
| 9,028,499 | B2 | 5/2015 | Keyak et al. |
| 9,119,655 | B2 | 9/2015 | Bowling et al. |
| 9,381,085 | B2 | 7/2016 | Axelson, Jr. et al. |
| 9,566,121 | B2 | 2/2017 | Staunton et al. |
| 9,588,587 | B2 | 3/2017 | Otto et al. |
| 9,707,043 | B2 | 7/2017 | Bozung |
| 10,117,713 | B2 | 11/2018 | Moctezuma de la Barrera et al. |
| 10,327,849 | B2 | 6/2019 | Post |
| 10,679,350 | B2 | 6/2020 | Groth et al. |
| 2004/0068187 | A1 | 4/2004 | Krause et al. |
| 2004/0171924 | A1 | 9/2004 | Mire et al. |
| 2006/0110017 | A1 | 5/2006 | Tsai et al. |
| 2007/0142751 | A1 | 6/2007 | Kang et al. |
| 2007/0255288 | A1 | 11/2007 | Mahfouz et al. |
| 2009/0089034 | A1 | 4/2009 | Penney et al. |
| 2009/0149977 | A1 | 6/2009 | Schendel |
| 2009/0310835 | A1 | 12/2009 | Kaus et al. |
| 2010/0153081 | A1 | 6/2010 | Bellettre et al. |
| 2010/0217400 | A1 | 8/2010 | Nortman et al. |
| 2016/0256279 | A1 | 9/2016 | Sanders et al. |
| 2019/0231447 | A1 | 8/2019 | Ebbitt et al. |
| 2019/0365475 | A1 | 12/2019 | Krishnaswamy et al. |
| 2019/0374295 | A1 | 12/2019 | Librot |
| 2020/0170604 | A1 | 6/2020 | Yildirim et al. |
| 2020/0188025 | A1 | 6/2020 | Becker et al. |

FOREIGN PATENT DOCUMENTS

| | | | |
|---|---|---|---|
| WO | 2006091494 | A1 | 8/2006 |
| WO | 2012017375 | A2 | 2/2012 |
| WO | 2013152341 | A1 | 10/2013 |

OTHER PUBLICATIONS

Zou, Y., Liu, P. X., Yang, C., Li, C., & Cheng, Q. (2017). Collision detection for virtual environment using particle swarm optimization with adaptive cauchy mutation. Cluster Computing, 20(2), 1765-1774. (Year: 2017).*

Chien, Chih-Chien et al., "Computation of Liver Deformations with Finite Elemenr Model", International Automatic Control Conference, 2017, pp. 1-6.

Lam, Fhkam, Ying-Lee et al., Is it Possible and Safe to Perform Acetablular-Preserving Resections for Malignant Neoplasms od the Periacetabular Region?:, Clin. Orthop. Related Res., vol. 475, 2017, pp. 656-665.

Palomar, Rafael et al., "A Novel Method for Planning Liver Resections Using Deformable Bezier Surfaces and Distance Maps", Computer Methods and Programs in Biomedicine, vol. 144, 2017, pp. 135-145.

Subburaj, K. et al., "Automated 3D Geometric Reasoning in Computer-Assisted Joint Reconstructive Surgery", 5th Annual IEEE Conference on Automation Science and Engineering, 2009, pp. 367-372.

Aponte-Tinao, L. A et al., "Multiplanar Osteotomies Guided by Navigation in Chondrosarcoma of the Knee," Orthopedics, vol. 36, No. 3, 2013, pp. e325-e330.

Aponte-Tinao, L.E.et al., "Does Intraoperative Navigation Assistance Improve Bone Tumor Resection and Allograft Reconstruction Results?," Clin. Orthop. Relat. Res.,vol. 473, No. 3, Mar. 2015, pp. 796-804.

Arad, N. et al., "Isometric Texture Mapping for Free-form Surfaces," Comput. Graph. Forum, vol. 16, No. 5, Dec. 1997, pp. 247-256.

Augello, M et al., "Performing Partial Mandibular Resection, Fibula Free Flap Reconstruction and Midfacial Osteotomies With a Cold Ablation and Robot-Guided Er:YAG Laser Ssteotome (CARLO®)—A study on Applicability and Effectiveness in Human Cadavers," J. Cranio-Maxillofacial Surg., vol. 46, No. 10, Oct. 2018, pp. 1850-1855.

Avedian R.S. et al. "Multiplanar Osteotomy With Limited Wide Margins: A Tissue Preserving Surgical Technique for High-Grade Bone Sarcomas," Clin. Orthop. Relat. Res., vol. 468, No. 10, 2010, pp. 2754-2764.

Bellanova, L. et al., "Surgical Guides (Patient-Specific Instruments) for Pediatric Tibial Bone Sarcoma Resection and Allograft Reconstruction," Sarcoma, 2013, pp. 1-7.

Bennis, C. et al., "Piecewise Surface Flattening for Non-Distorted Texture Mapping," ACM SIGGRAPH Comput. Graph., vol. 25, No. 4, Jul. 1991, pp. 237-246.

Bosma, E. et al., "A Cadaveric Comparative Study on the Surgical Accuracy of Freehand, Computer Navigation, and Patient-Specific Instruments in Joint-Preserving Bone Tumor Resections," Sarcoma, vol. 2018, Nov. 2018, pp. 1-9.

Carrillo, F. et al., "An Automatic Genetic Aalgorithm Framework for the Optimization of Three-Dimensional Ssurgical Plans of Forearm Corrective Osteotomies," Med. Image Anal., vol. 60, Feb. 2020, p. 101598.

Cartiaux L. et al., "Improved Accuracy With 3D Planning and Patient-Specific Instruments During Simulated Pelvic Bone Tumor Surgery.," Ann. Biomed. Eng., vol. 42, No. 1, Jan. 2014, pp. 205-213.

Cartiaux, O. et al., "Surgical Inaccuracy of Tumor Resection and Reconstruction Within the Pelvis: An Experimental Study.," Acta Orthop., vol. 79, No. 5, Oct. 2008, pp. 695-702.

Chen, H.-Y et al., "Approximation by Ruled Ssurfaces," J. Comput. Appl. Math., vol. 102, No. 1, Feb. 1999, pp. 143-156.

Cheong, D. et al., "Computer-Assisted Navigation and Musculoskeletal Sarcoma Surgery.," Cancer Control, vol. 18, No. 3, Jul. 2011, pp. 171-176.

Cho, H.S., "The Outcomes of Navigation-Assisted Bone Tumour Surgery: Minimum Three-Year Follow-Up.," J. Bone Joint Surg. Br., vol. 94, No. 10, Oct. 2012, pp. 1414-1420.

Choong, P. F. M.et al., "Limb-Sparing Surgery For Bone Tumors: New Developments," Semin. Surg. Oncol., vol. 13, No. 1, Jan. 1997, pp. 64-69.

Edelsbrunner, H. et al., "On the Shape of a Set of Points in the Plane," IEEE Trans. Inf. Theory, vol. 29, No. 4, Jul. 1983, pp. 551-559.

Elber, G. et al., "5-Axis Freeform Surface Milling Using Piecewise Ruled Surface Approximation," J. Manuf. Sci. Eng.,vol. 119, No. 3, Aug. 1997,Updated Mar. 2000, 25 pages.

Enneking, W. F. et al., "A System For the Surgical Staging of Musculoskeletal Sarcoma," Clin. Orthop. Relat. Res., vol. 153, 1980, pp. 106-120.

Flory, S. et al., "Ruled Surfaces For Rationalization and Design in Architecture," LIFE Information On Responsive Information and Variations in Architecture, 2010, pp. 103-109.

Fritsch, F.N. et al., "Monotone Piecewise Cubic Interpolation," SIAM J. Numer. Anal., vol. 17, No. 2, Apr. 1980, pp. 238-246.

Fürnstahl, P. et al., "Complex Osteotomies of Tibial Plateau Malunions Using Computer-Assisted Planning and Patient-Specific Surgical Guides," J. Orthop. Trauma, vol. 29, No. 8, Aug. 2015, 25 pages.

Gerbers, J.G. et al., "Computer-Assisted Surgery in Orthopedic Oncology.," Acta Orthop., vol. 85, No. 6, Dec. 2014, pp. 663-669.

Gladilin, E. et al., "Computational Modelling and Optimisation of Soft Tissue Outcome in Cranio-Maxillofacial Surgery Planning," Comput. Methods Biomech. Biomed. Engin., vol. 12, No. 3, Jun. 2009, pp. 305-318.

(56) References Cited

OTHER PUBLICATIONS

Gouin, L. et al., "Computer-Assisted Planning and Patient-Specific Instruments for Bone Tumor Resection within the Pelvis: A Series of 11 Patients," Sarcoma, 2014, pp. 1-9.
Han, Z. et al., "Isophote-Based Ruled Ssurface Aapproximation of Free-Form Surfaces and its Aapplication in NC Machining," Int. J. Prod. Res., vol. 39, No. 9, Jan. 2001, pp. 1911-1930.
Hao, Y., "The Accurate Surgical Margin Before Surgery For Malignant Musculoskeletal Tumors: A Retrospective Study.," Am. J. Transl. Res., vol. 10, No. 8, 2018, pp. 2324-2334.
Abstract of Hennessy, M. et al., "Complex Pelvic Reconstruction using Patient-Specific Instrumentation and a 3D-Printed Custom Implant following Tumor Resection," J. Hip Surg., vol. 02, No. 02, Jun. 2018, 2 pages.
Hoschek, J. et al., "Interpolation and Approximation With Ruled Surfaces," The Mathematics of Surfaces, vol. 8. 1998, pp. 213-231.
Jaffe, N. et al., "Osteosarcoma: Evolution of Treatment Paradigms," Sarcoma, vol. 2013, 2013, pp. 1-8.
Jentzach, L. et al., "Tumor Resection at the Pelvis Using Three-Dimensional Planning and Patient-Specific Instruments: A Case Series," World J. Surg. Oncol., vol. 14, No. 1, Dec. 2016, p. 249.
Jeys, L. et al., "Can Computer Navigation-Assisted Surgery Reduce the Risk of an Intralesional Margin and Reduce the Rate of Local Recurrence in Patients With a Tumour of the Pelvis or Sacrum?," Bone Joint J., vol. 95-B, No. 10, Oct. 2013, pp. 1417-1424.
Jivraj, J. et al., "Robotic Laser Osteotomy Through Penscriptive Structured Light Visual Servoing," Int. J. Comput. Assist. Radiol. Surg., vol. 14, No. 5, May 2019, pp. 809-818.
Kennedy, J. et al., "Particle Swarm Optimization," in Proceedings of ICNN'95—International Conference on Neural Networks, 1995, vol. 4, pp. 1942-1948.
Khan, F. et al., "Haptic Robot-Assisted Surgery Improves Accuracy of Wide Resection of Bone Tumors: A Pilot Study," Clin. Orthop. Relat. Res., vol. 471, No. 3, Mar. 2013, pp. 851-859.
Krettek, C. et al., "Computer Aided Tumor Resection In the Pelvis.," Injury, vol. 35 Suppl 1, Jun. 2004, pp. A79-83.
Lorensen, W.E. et al., "Marching Cubes: A High Resolution 3D Surface Construction Algorithm," ACM SIGGRAPH Comput. Graph., vol. 21, No. 4, Aug. 1987, pp. 163-169.
Massarwi, F. et al., "Papercraft Models Using Generalized Cylinders," in 15th Pacific Conference on Computer Graphics and Applications (PG'07), 2007, pp. 148-157.
McCormick, M. et al., "ITK: Enabling Reproducible Research and Open Science," Front. Neuroinform., vol. 8, 2014, 11 Pages.
Mitani, J. et al., "Making Papercraft Toys From Meshes Using Strip-Based Approximate Unfolding," ACM Trans. Graph., vol. 23, No. 3, Aug. 2004, p. 259.
Noble, J.H. et al., "Automatic Determination of Optimal Linear Drilling Trajectories For Cochlear Access Accounting For Drill-Positioning Error," Int. J. Med. Robot. Comput. Assist. Surg., vol. 6, No. 3, Sep. 2010, pp. 281-290.
Nolden, M. et al., "The Medical Imaging Interaction Toolkit: Challenges and Advances," Int. J. Comput. Assist. Radiol Surg.,vol. 8, No. 4, Jul. 2013, pp. 607-620.
Ozturk A.M. et al., "Multidisciplinary Assessment of Planning and Resection of Complex Bone Tumor Using Patient-Specific 3D Model," Indian J. Surg. Oncol., vol. 10, No. 1, Mar. 2019, pp. 115-124.
Pottman, H. et al., "Approximation Algorithms For Developable Surfaces," Comput. Aided Geom. Des., vol. 16, No. 6, Jul. 1999, pp. 539-556.
Ritacco, L.E.et al., "Accuracy of 3-D Planning and Navigation in Bone Tumor Resection," Orthopedics, vol. 36, No. 7, 2013, pp. e942-e950.
Saidi, K., "Potential Use of Computer Navigation in the Treatment of Primary Benign and Malignant Tumors in Children," Curr. Rev. Musculoskelet. Med., vol. 5, No. 2, Jun. 2012, pp. 83-90.
Shidid, D. et al., "Just-In-Time Design and Additive Manufacture of Patient-Specific Medical Implants," Phys. Procedia, vol. 83, 2016, pp. 4-14.
Shoemake, K., "Animating Rotation With Quaternion Curves," in SIGGRAPH '85: Proceedings of the 12th Annual Conference on Computer Graphics and Iinteractive Techniques, 1985, pp. 245-254.
So, T.Y.C. et al., "Computer-Assisted Navigation in Bone Tumor Surgery: Seamless Workflow Model and Evolution of Technique.," Clin. Orthop Relat. Res., vol. 468, No. 11, Nov. 2010, pp. 2985-2991.
Stein, O. et al., "Developability of Triangle Meshes," ACM Trans. Graph., vol. 37, No. 4, Aug. 2018, pp. 1-14.
Tang, K. et al. "Modeling Developable Folds on a Strip," J. Comput. Inf. Sci. Eng., vol. 5, No. 1, Mar. 2005, pp. 35-47.
Tang, P. et al., "Interactive Design of Developable Surfaces," ACM Trans. Graph., vol. 35, No. 2, May 2016, pp. 1-12.
Vodanovich, D.A. et al., "Soft-Tissue Sarcomas," Indian J. Orthop., vol. 52, No. 1,2018, pp. 35-44.
Wang, C.C.L. et al., "Multi-Dimensional Dynamic Programming in Rruled Surface Fitting," Comput. Des., vol. 51, Jun. 2014, pp. 39-49.
Wong, K. C. et al., "Computer-Assisted Tumor Surgery in Malignant Bone Tumors," Clin. Orthop. Relat. Res., vol. 471, No. 3, 2013, pp. 750-761.
Wong, K.-C. et al., "Use of Computer Navigation in Orthopedic Oncology," Curr. Surg. Reports, vol. 2, No. 4, 2014, 8 Pages.
Wong, K.-C. et al., "Patient-Specific Instrument Can Achieve Same Accuracy With Less Resection Time Than Navigation Assistance in Periacetabular Pelvic Tumor Surgery: A Cadaveric Study," Int. J. Comput. Assist. Radiol. Surg., vol. 11, No. 2, Feb. 2016, pp. 307-316.
Wong, K.C., "Joint-Preserving Tumor Resection and Reconstruction Using Image-Guided Computer Navigation.," Clin. Orthop. Relat. Res., vol. 471, No. 3, Mar. 2013, pp. 762-773.
Wong, T.M. et al., "The Use of Three-Dimensional Printing Technology in Orthopaedic Surgery," J. Orthop. Surg., vol. 25, No. 1, Jan. 2017, 7 Pages.
Young, P.S. et al., "The Evolving Role of Computer-Assisted Navigation in Musculoskeletal Oncology," Bone Jt. J., vol. 97-B, No. 2, 2015, pp. 258-264.
Zachow, S. et al., "Draw and Cut: Intuitive 3D Osteotomy Planning on Polygonal Bone Models," Int. Congr. Ser., vol. 1256, Jun. 2003, pp. 362-369.
Zha, X.F. "A New Approach to Generation of Ruled Surfaces and Its Aapplications in Engineering," Int. J. Adv. Manuf. Technol., vol. 13, No. 3, Mar. 1997, pp. 155-163.
Zhang, X.-M. et al., "Tool Path Optimisation for Flank Milling Ruled Surface Based on the Distance Function," Int. J. Prod. Res., vol. 48, No. 14, Jul. 2010, pp. 4233-4251.
Zhang, Y. et al., "Toward Precise Osteotomies: A Coarse-To-Fine 3D Cut Plane Planning Method for Image-Guided Pelvis Tumor Resection Surgery," IEEE Trans. Med. Imaging, vol. 14, No. 8, 2019, pp. e942-e950.
Zhang, Yu et al., "Toward Precise Osteotomies: A Coarse-To-Fine Cut Plane Planning Method for Image-Guided Pelvis Tumor Resection Surgery", Journal of Latex Class Files, vol. 14, No. 8, Aug. 2015, 13 pages.

* cited by examiner

| Tumor Volume (ml) | Bone Volume Removed (ml) | | | No-Go Volume Removed (ml) | |
|---|---|---|---|---|---|
| | Initial | Optimized | %Improvement | Initial | Optimized |
| 12.2 | 24.0 | 21.6 | 10.0 | 0.0 | 0.0 |
| 86.4 | 101.4 | 101.0 | 0.3 | 16.8 | 16.5 |
| 51.4 | 78.7 | 77.7 | 1.3 | 0.0 | 0.0 |
| 7.4 | 18.0 | 17.6 | 2.5 | 0.0 | 0.0 |
| 12.3 | 40.4 | 29.7 | 26.3 | 1.5 | 0.0 |

FIG. 13

| Margin Volume (ml) | Bone Volume Removed (ml) | | | No-Go Volume Removed (ml) | |
|---|---|---|---|---|---|
| | Initial | Optimized | %Improvement | Initial | Optimized |
| 46.4 | 64.7 | 61.0 | 5.7 | 0.0 | 0.0 |
| 129.7 | 136.4 | 136.4 | 0.0 | 25.7 | 25.6 |
| 108.2 | 119.3 | 117.8 | 1.3 | 0.0 | 0.0 |
| 44.3 | 67.1 | 66.3 | 1.2 | 2.0 | 1.8 |
| 54.8 | 81.4 | 69.0 | 15.2 | 11.8 | 4.9 |

FIG. 14

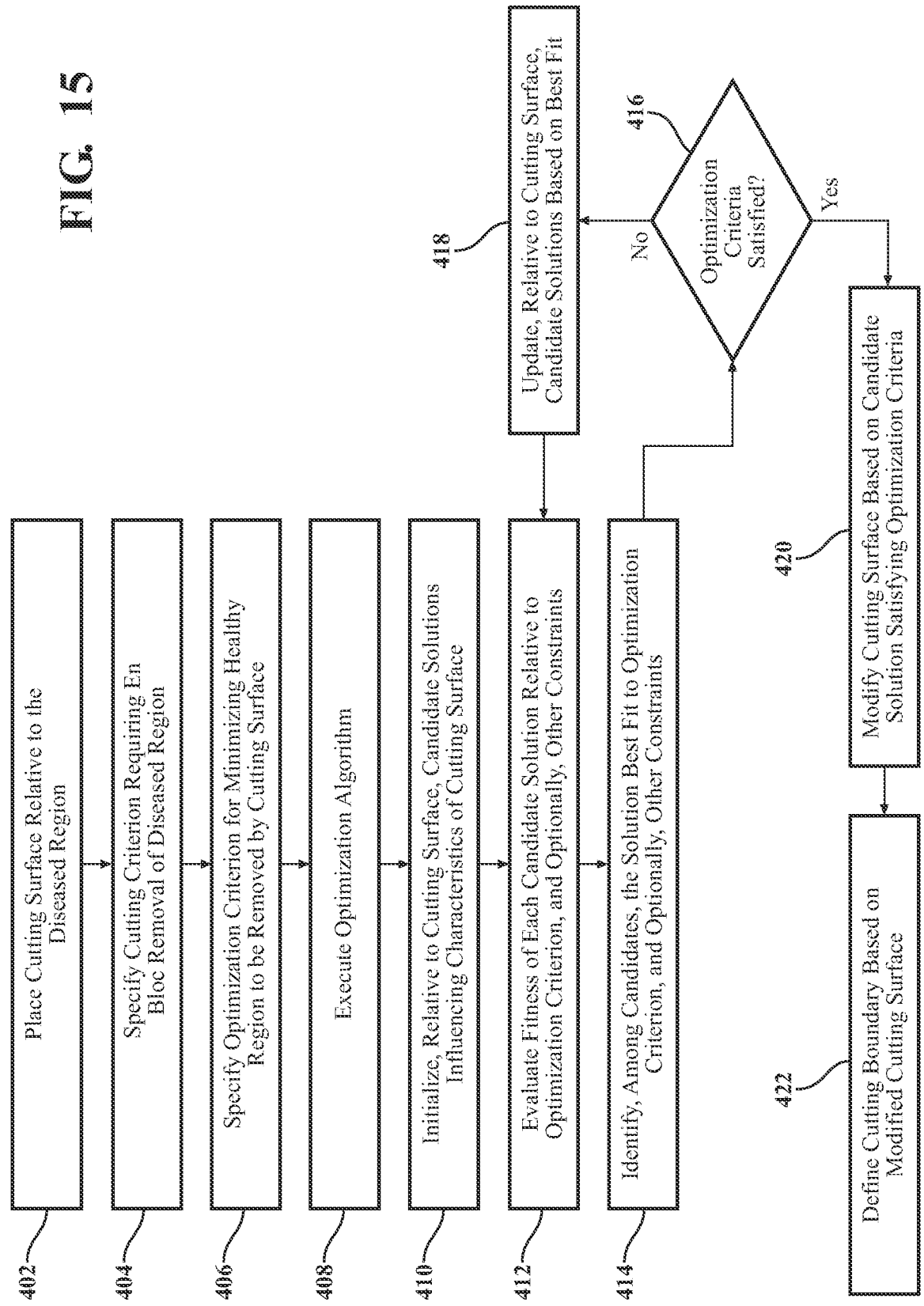

AUTOMATED CUT PLANNING FOR REMOVAL OF DISEASED REGIONS

CROSS-REFERENCE TO RELATED APPLICATIONS

The subject application claims priority to and all the benefits of U.S. Provisional Patent Application No. 62/990,038, filed Mar. 16, 2020, the entire disclosure of which is hereby incorporated by reference.

TECHNICAL FIELD

The subject disclosure relates to systems, methods, programs, and techniques for automated generation of surgical cutting plans for removing diseased regions of an anatomy, such as bone tumors.

BACKGROUND

A standard practice is to surgically remove malignant bone tumors with the lesion intact (remaining in one piece) to ensure no tumor cells remain which can cause local recurrence. A primary aim of excision or resection remains achieving tumor free margins, even at the expense of sacrificing some function of the limb (in the form of removing additional healthy bone). The definition of surgical margins of surrounding healthy tissue and subsequent planning of cutting planes are important steps in these procedures. Margin definition depends on several factors, including the size and position of the tumor, presence of skip or secondary lesions, and the infiltration of the tumor through multiple anatomical compartments (for example beyond the growth plates or into soft tissue).

The accuracy at which the surgeon can complete the planned cuts is a significant factor in the planning stage as it directly informs how wide the margins are defined as well as the final oncological and functional outcomes. Yet, conventional bone tumor removal planning is a technically demanding and time-consuming task that is heavily reliant on surgeon experience and skill. For example, surgeons manually identify landmarks representing the tumor margin on pre-operative images and manually position cutting planes.

Additionally, conventional means of planning bone tumor removal are limited to straight cutting planes. However, bone tumors can have complex geometries for which straight cutting planes are not particularly suitable. Furthermore, aside from post-operatively examining the tumor margins, there is no measure of the quality of a tumor cutting plan, nor is there means to numerically compare one cutting plan to another. There is a need to address at least the aforementioned challenges.

SUMMARY

This Summary introduces a selection of concepts in a simplified form that are further described below in the Detailed Description below. This Summary is not intended to limit the scope of the claimed subject matter, and does not necessarily identify each and every key or essential feature of the claimed subject matter.

According to a first aspect, a computer-implemented method is provided for automated planning of a cutting boundary for removal of a diseased region of an anatomy. The method utilizes a model of the diseased region and the computer-implemented method comprising: defining, relative to the model, a first plane and a second plane being spaced apart from the first plane; identifying a geometrical feature of the model; providing a first reference spline derived from the geometrical feature onto the first plane; providing a second reference spline derived from the geometrical feature onto the second plane; creating a first set of ruled surfaces extending between the reference splines; optimizing a shape of one or both of the reference splines to thereby define one or both of an optimized first spline and an optimized second spline, wherein optimizing is based on minimizing a volume bounded by the first set of ruled surfaces and the first and second planes; creating a second set of ruled surfaces extending between one of the reference splines and one of the optimized splines or extending between the optimized splines; and defining the cutting boundary based on the second set of ruled surfaces.

According to a second aspect, a computer-implemented method is provided for automated planning of a cutting boundary for removal of a diseased region of an anatomy, the method utilizing a model of the diseased region and a healthy region of the anatomy and utilizing a cutting surface defining a region to be removed from the anatomy, the computer-implemented method comprising: placing the cutting surface relative to the model of the diseased region; executing an optimization algorithm comprising: specifying an optimization criterion that minimizes an amount of healthy region to be removed by the cutting surface; initializing, relative to the cutting surface, candidate solutions influencing characteristics of the cutting surface; and iteratively performing the following sub-steps (1) to (3) until the candidate solution is identified that satisfies the optimization criterion: (1) evaluating fitness of each of the candidate solution relative to the optimization criterion; (2) identifying, among the candidate solutions, the candidate solution best fit to the optimization criterion; and (3) updating, relative to the cutting surface, the candidate solutions based on the candidate solution best fit to the optimization criterion; modifying characteristics of the cutting surface based on the identified candidate solution that satisfies the optimization criterion; and defining the cutting boundary relative to the model based on the modified cutting surface.

According to a third aspect, a computer-implemented method is provided for automated planning of a cutting boundary for removal of a diseased region of an anatomy, the method utilizing a model of the diseased region and a healthy region of the anatomy and utilizing one or more cutting geometries defining a region to be removed from the anatomy, the computer-implemented method comprising: automatically placing the one or more cutting geometries relative to the model; automatically optimizing one or more of a size, shape, position and orientation of the one or more cutting geometries relative to the model based on the following: a cutting criterion requiring that the one or more cutting geometries be planned for removal of an entirety of the diseased region as a single piece; and an optimization criterion that minimizes an amount of healthy region to be removed by the one or more cutting geometries; and automatically defining the cutting boundary relative to the model based on the optimized cutting geometry.

According to a fourth aspect, a non-transitory computer readable medium or computer program product is provided having stored thereon instructions, which when executed by one or more processors, implement the computer-implemented method of any one or more of the first, second, or third aspects.

According to a fifth aspect, a robotic surgical system is provided, comprising: a robotic device configured to support a surgical tool; and one or more controllers comprising a non-transitory computer readable medium having stored thereon instructions, which when executed by one or more processors, implement the computer-implemented method of any one or more of the first, second or third aspects, wherein the one or more controllers are configured to control the robotic device to move the surgical tool relative to the cutting boundary to remove the diseased region of the anatomy.

Any of the aspects above may be combined in-whole or in part.

Any of the aspects above may be utilized with any one or more of the following implementations, whether utilized individually or in combination:

Some implementations comprise the geometrical feature being a contour of the diseased region, or an outermost contour of the diseased region. Some implementations comprise: providing one or both reference splines to have a contour being proportionally similar to and proportionally larger than the outermost contour. Some implementations comprise: identifying the geometrical feature to be a closed-loop contour; and providing the first and second reference splines to be closed-loop contours.

Some implementations comprise: obtaining a primary axis along which to evaluate the diseased region; and aligning a z-axis of a coordinate system of the model to the primary axis; and identifying the geometrical feature within an x-y plane of the coordinate system of the model. Some implementations comprise: the primary axis further defined as an axis along which a surgical tool should access the diseased region, and identifying the primary axis by: receiving input of primary axis based on surgical plan or surgeon preference; or automatically determining the primary axis based on evaluation of the model.

Some implementations comprise: identifying one or more boundaries of the model relative to the primary axis; and defining one or both of the first or second planes at or beyond one of the boundaries of the model.

Some implementations comprise: defining the first and second planes to be parallel to one another; and defining the first and second planes to intersect the primary axis.

Some implementations comprise: projecting the geometrical feature along the primary axis onto one or both planes to define one or both reference splines wherein one or both reference splines has a geometry being congruent to the geometrical feature and having identical coordinates to the geometrical feature in the x-y plane of the coordinate system of the model.

Some implementations comprise: defining a third plane above the second set of ruled surfaces with reference to the z-axis; extending the second set of ruled surfaces to the third plane; defining a fourth plane below the second set of ruled surfaces with reference to the z-axis; and extending the second set of ruled surfaces to the fourth plane.

Some implementations comprise: further utilizing a model of healthy anatomy adjacent to the diseased region; and aligning the z-axis of a coordinate system of the model of healthy anatomy to the primary axis; identifying an uppermost reference and a lowermost reference of the model of healthy anatomy relative to the z-axis; defining the third plane at or above the uppermost reference of the model of healthy anatomy; and defining the fourth plane at or below the lowermost reference of the model of healthy anatomy.

Some implementations comprise: identifying locations of intersections among the second set of ruled surfaces occurring from extending the second set of ruled surfaces to the fourth plane; and defining an intersection reference geometry based on the identified locations of intersections. Some implementations comprise defining the cutting boundary based on the second set of ruled surfaces extending between the third plane and the intersection reference geometry.

Some implementations comprise: utilizing a model of healthy anatomy adjacent to the diseased region and minimizing the volume by minimizing a volume of healthy anatomy bounded by the first set of ruled surfaces and the first and second planes.

Some implementations comprise: optimizing a shape of one or both reference splines by: determining that one or more ruled surfaces of the first set intersects the model; and adjusting position and/or orientation of the one or more of the ruled surfaces of the first set to not intersect the model thereby adjusting the shape of one or both reference splines. Some implementations comprise: optimizing a shape of one or both reference splines and/or one or both optimized splines by: determining that one or more ruled surfaces intersects the model; and adjusting position and/or orientation of the one or more of the ruled surfaces to not intersect the model.

Some implementations comprise: optimizing a shape of one or both reference splines by: obtaining an access angle defining planned access angle of the diseased region by a surgical tool; and adjusting position and/or orientation of the one or more of the ruled surfaces of the first set to not exceed the access angle thereby adjusting the shape of one or both reference splines.

Some implementations comprise: utilizing a model of healthy anatomy adjacent to the diseased region, and comprising optimizing a shape of one or both reference splines by: identifying, with respect to the model of healthy anatomy, one or more virtual boundaries defining regions to be avoided by a surgical tool; and adjusting position and/or orientation of the one or more of the ruled surfaces of the first set to not intersect any of the one or more of virtual boundaries thereby adjusting the shape of one or both reference splines.

Some implementations comprise: identifying a geometric origin of the model; and defining the first or second plane to intersect the geometric origin of the model.

Some implementations comprise: defining points along the first reference spline to define a first reference point set; defining points along the second reference spline to define a second reference point set; and creating the first set of ruled surfaces such that each ruled surface of the first set has vertices defined by adjacent points in the first reference point set and adjacent points in the second reference point set.

Some implementations comprise: defining points along one or both of the optimized splines to define one or both first and second optimized point sets; and creating the second set of ruled surfaces such that each ruled surface of the second set has vertices defined by: adjacent points in one optimized point set and adjacent points in one reference point set; or adjacent points in the first optimized point set and adjacent points in the second optimized point set.

Some implementations comprise: modifying characteristics of the cutting surface comprises modifying one or more of a size, position, and orientation of the cutting surface.

Some implementations comprise a plurality of discrete cutting surfaces, and modifying characteristics of the discrete cutting surfaces comprises modifying one or more of: a size of one or more of the discrete cutting surfaces and a position and/or orientation of one or more of the discrete cutting surfaces.

Some implementations comprise: a plurality of cutting surfaces arranged in a hull, and modifying characteristics of the cutting surfaces comprises modifying one or more of: a size of the cutting surfaces; a position and/or orientation of the cutting surfaces; and a position and/or orientation of a vertex or focal point of the hull.

Some implementations comprise: one or more cutting surfaces defining a volume and modifying characteristics of the volume comprises modifying one or more of: a size of the volume and a position and/or orientation of the volume.

Some implementations comprise: the model of the healthy region comprising additional anatomical features to be avoided and specifying a criterion that penalizes or rewards one or more of the candidate solutions based on an amount of additional anatomical features to be avoided.

Some implementations comprise: the model is a three-dimension model, and the model and the cutting surface are positioned in a three-dimensional coordinate system. Some implementations comprise: automatically placing the cutting surface relative to the model. Some implementations comprise: manually placing the cutting surface relative to the model. Some implementations comprise: placing the cutting surface relative to the model such that the diseased region is included in the portion of the anatomy to be removed. Some implementations comprise: automatically placing the cutting surface relative to the model by automatically placing the cutting surface relative to one of the following: a most-distant point of the model of the diseased region determined relative to an axis of the three-dimensional coordinate system; an arbitrary location outside of a boundary of the model of the diseased region; and a centroid of the model of the diseased region.

Some implementations comprise: initializing, relative to the cutting surface, candidate solutions by initializing a random set of candidate solutions. Some implementations comprise: the optimization algorithm is an evolutionary algorithm, and optionally, wherein the evolutionary algorithm is a particle swarm optimization algorithm.

Some implementations comprise: specifying a cutting criterion to the optimization algorithm requiring that the cutting surface be planned for removal of an entirety of the diseased region as a single piece.

Some implementations provide visual or graphical depiction of aspects of the automated planning techniques, including the model, cutting surfaces, and features thereof. Some implementations provide that the automated planning technique be performed purely computationally, without visual or graphical depiction to the user.

BRIEF DESCRIPTION OF THE DRAWINGS

FIGS. 2A-4A illustrate example computer-generated models of an anatomy including healthy regions and diseased regions, in this example, bone tumors.

FIGS. 2B-4B illustrate example computer generated models, corresponding to those of FIGS. 2A-4A, respectively, showing cutting boundaries, defined according to automated planning techniques described herein, for removing the diseased region.

in FIG. 12B bone slice contours are identified; in FIG. 12C ruled surfaces are sliced into cut slice contours; in FIG. 12D corresponding bone and cut slice contour pairs are identified; in FIG. 12E the intersection of the contour pair is identified; and 12F the volume is computed using Simpson's rule for numerical approximation of integrals.

FIGS. 13 and 14 each provide a table illustrating sample results from implementation of the ruled surface approach to the automated cut planning techniques described herein for each of five test cases with surgical resection margins of 0 and 10 mm, respectively.

FIG. 15 is a flowchart of one implementation of an evolutionary algorithm optimization method to the automated cut planning techniques described herein.

DETAILED DESCRIPTION

I. Techniques for Automated Cut Planning for Bone Tumor Removal

With reference to the Figures, described herein are computer-implemented methods for automated planning of a cutting boundary (CB) for removal of a diseased region (DR) of an anatomy (A). The anatomy (A) can be any type of tissue or bone, such as, but not limited to a bone of a joint or long bones, such as arm or leg bones, including the lower end of the thighbone (femur), the upper end of the lower leg bone (tibia), and the upper end of the upper arm bone (humerus). The diseased region (DR) is any portion of the anatomy to be surgically removed due to abnormalities or damage. In one example, the diseased region (DR) is a tumor, such as a bone tumor. The tumor can be any type, benign or malignant, and can be osteochondroma, solitary bone cysts, giant cell tumors, enchondroma, fibrous dysplasia and/or aneurysmal bone cyst. The diseased region (DR) can also be any region requiring resection for partial or total knee or hip replacement surgery, shoulder replacement surgery, spine surgery, ankle surgery, and the like.

Figure 1:
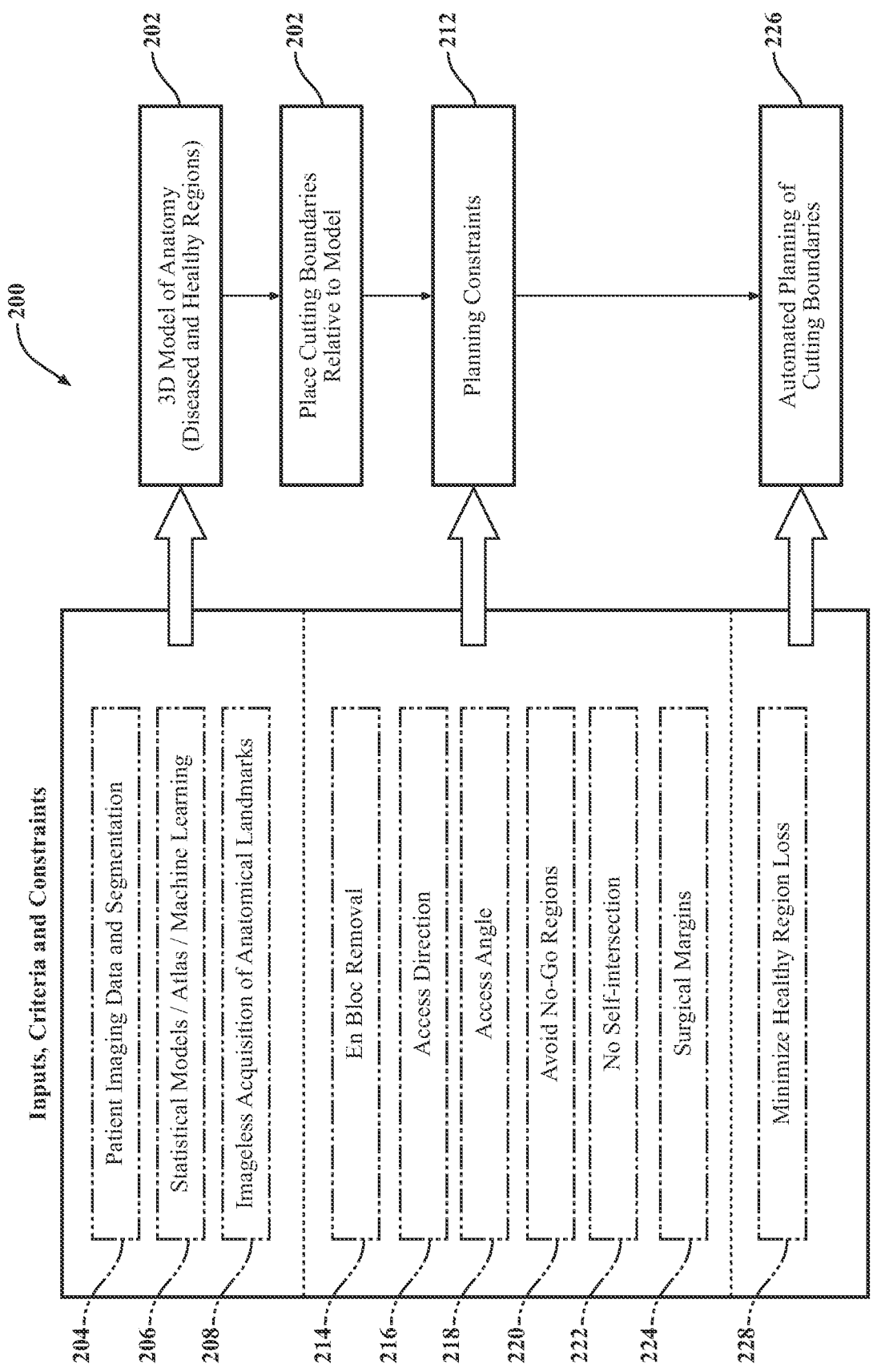
FIG. 1 is a block diagram of one implementation of an automated cut planning technique for generating cutting boundaries for removal of a diseased region.
Figure 2A:
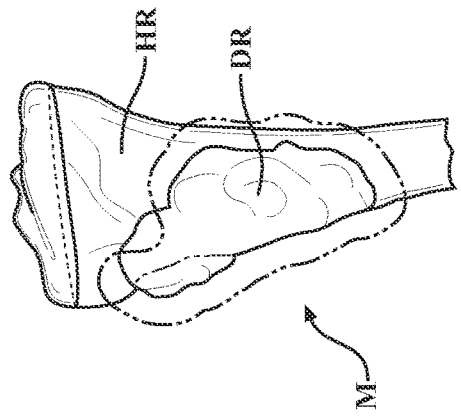

With reference to FIG. 1, an example method 200 is provided for automated planning with inputs, parameters, and constraints shown for each respective step. At step 202, a three-dimensional computer-generated model (M) of the diseased region (DR), and optionally a healthy region (HR), of the anatomy (A) are obtained. Examples of some models (M) are shown in FIG. 2.

In one example, at 204, the anatomy (A) is preoperatively or intraoperatively imaged using imaging techniques such as, but not limited to CT, x-ray, MRI, etc. The imaging data can be a DICOM image imported to the system. An image processing technique, such as segmentation, may be manually or automatically performed to convert the imaging data into the computer-generated model (M). Segmentation can be performed for the entire anatomy (A) and/or for the diseased region (DR) and healthy region (HR) individually, or in combination. Segmentation can also be performed to define "no-go zones" (N) for other critical structures of the anatomy (A) that should be avoided by cutting, such as nerves, vessels, articulating surfaces, ligament insertions, and the like. In some instances, at 206, the anatomy (A) model is generated based, in part or in whole, on statistical models or atlas data. In other examples, the model (M) can generated, modified, and/or segmented using machine learning, such as a neural networks trained to specific populations. The model (M) can also be generated using imageless techniques, shown at 208, wherein a tracked probe or digitizer is intraoperatively utilized to obtain landmarks of the anatomy (A). The model (M) can be represented as a mesh of polygonal elements (e.g., triangles) or a NURBS surface. Any other technique for generating the model (M) of the anatomy (A) is contemplated.

As will be described in detail below, once the model (M) is generated, one or more cutting boundaries (CB) are planned relative to the model (M) in a coordinate system of the model (M), shown at 210. The cutting boundaries (CB) can be initially placed relative to the model (M) based on an automated, manual or hybrid (manual and automated) process. The cutting boundaries (CB) delineate a region of the anatomy (A) intended for removal from a region of the anatomy (A) not intended for removal. The cutting boundaries (CB) can have various characteristics (shapes, sizes, volumes, positions, orientations, etc.). The cutting boundaries (CB) can be keep-in zones for keeping the tool within the boundary, keep-out zones for keeping the tool outside of a boundary, planar cut boundaries for keeping the tool on a planar cut path, and/or tool path boundaries for keeping the tool on a certain tool path. In some implementations, the cutting boundaries (CB) can be used to facilitate a complex cutting shapes, including corner cuts.

The techniques herein can automatically optimize characteristics of the one or more cutting boundaries (CB) relative to the diseased region (DR) based on a plurality of inputs, constraints, criterion or parameters, which we refer to as planning constraints, shown at 212. One such constraint is en bloc removal, shown at 214 in FIG. 1 and visually represented in FIG. 6. This is a cutting criterion requiring that the one or more cutting boundaries (CB) be planned for removal of an entirety of the diseased region (DR) as a single piece (en bloc) so as to prevent local recurrence. Intact removal of the complete diseased region (DR) may be implemented by constraints on the cutting boundary (CB) definition, such as requirements that the cutting boundary (CB) remain external to a surface of the diseased region (DR) without overlap and/or the cutting boundary (CB) fit be optimized to the to the surface of the diseased region (DR) as a whole, without division of the diseased region (DR).

Figure 5:
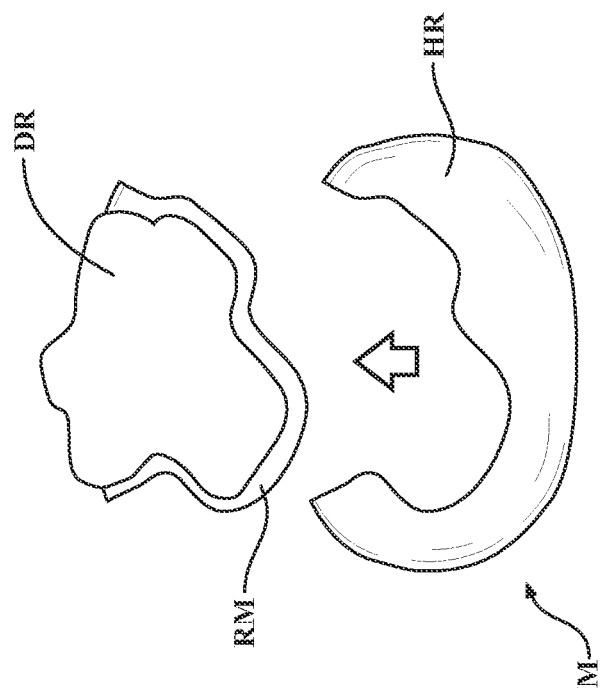
FIG. 5 illustrates an access direction and access angle defined relative to the diseased region, according to one example.

Additional planning constraints can be considered, such as requirements that the cutting boundary (CB) be accessed with respect to a defined approach direction or axis (AA), shown at 216 in FIG. 1 and visually represented in FIG. 5. The approach axis (AA) defines the planned primary approach for the surgeon to access the surgical site with a cutting tool. The approach direction or axis (AA) can be defined based on surgeon preference or can be determined (or optimized) based on automated techniques evaluating the position, orientation, and/or size of the model (M) of the diseased region (DR), e.g., relative to other features of the anatomy or limitations of the tool. In some implementations, the z-axis of the coordinate system in which the model (M) is located can be aligned to the approach axis (AA). Alternatively, the x or y-axis of the coordinate system in which the model (M) is located can be aligned to the approach axis (AA).

At 218 in FIG. 1 and as also visually represented in FIG. 5, an angle of access (Aθ) can also be inputted as a constraint into the optimization algorithm. The angle of access (Aθ) represents the degree of access to the surgical site desired or required to treat the tissue. An access angle (Aθ) of 0° limits the cutting direction to exactly along the access direction (i.e. as a cut out of the tumor) with greater angles meaning that the tool orientation can vary up to the desired value from the access direction (AA). In one non-limiting example, the approach axis (AA) and access angle (Aθ) can be understood as a three-dimensional representation, e.g., as a conical volume containing the diseased region (DR) whereby the axis of the cone is defined by the approach axis (AA) and the aperture of the cone is defined by the access angle (Aθ). In some implementations, the pose of the cutting boundary (CB) can be limited to an angle, or range of angles, to respect the limited access dictated by the approach axis (AA) and/or angle of access.

At 220, an addition requirement that can affect automated planning of the cutting boundary (CB) is that the cutting boundary (CB) does not pass through defined critical or no-go regions (N) or zones of the anatomy (A). Such regions are those beyond the diseased region (DR) and located in the healthy region (HR), which should be avoided by the cutting boundary (CB) to prevent removal of the critical structure. Such features include, but are not limited to nerves, vessels, articulating joint surfaces, ligaments or ligament insertions, tendons, and the like. These features can be imaged, segmented, and modeled to be included in the model (M) of the anatomy. The planning methods can position, orient, size and/or shape the cutting boundaries (CB) to avoid these regions.

To provide manageable cutting boundaries (CB), planning can also be constrained, as shown at 222, such that no cutting boundary (CB) intersects itself in the planning phase. Self-intersection can be addressed by proactively avoiding self-intersections or by allowing the self-intersection and removing portions of the cutting boundary (CB) that self-intersect. Additional examples of self-intersection are provided below.

Figure 6:
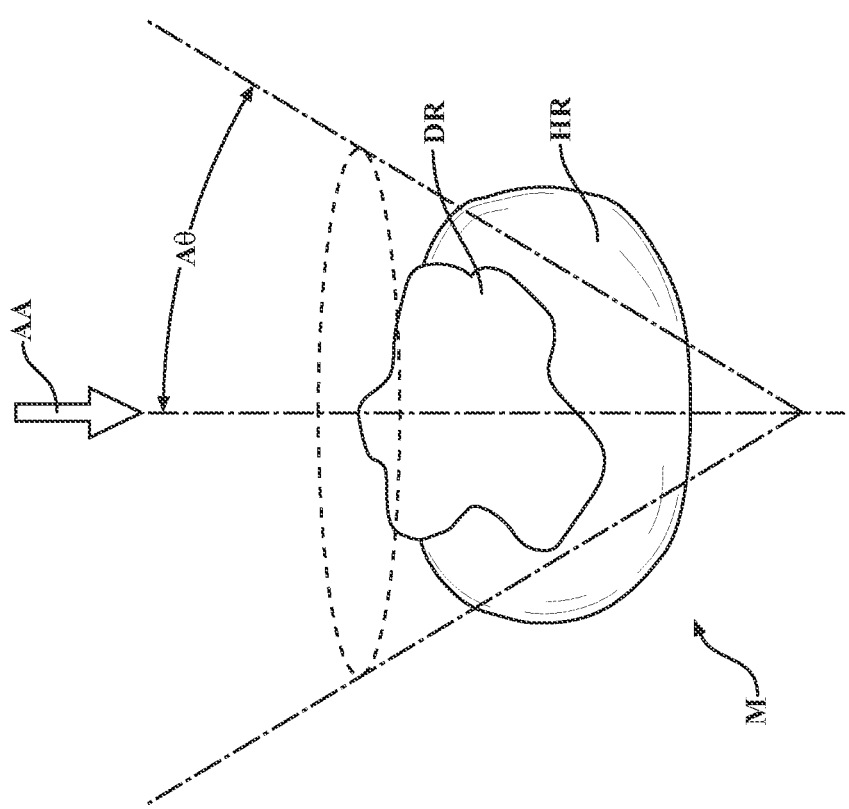
FIG. 6 illustrates en bloc removal of the diseased region relative to the access direction and angle of FIG. 5, and with surgical resection margins surrounding the diseased region, according to one example.

At 224 in FIG. 1, and as visually represented in FIG. 6, resection or surgical margin (RM) can also be inputted as a constraint on the automated planning techniques described herein. A margin (RM), as understood with respect to removal of malignant bone tumors, is the margin of non-tumorous tissue around the diseased region (DR) that has been surgically removed. The margin (RM) is described as negative when no cancer cells are present at the edge of the tissue, suggesting that all of the cancer has been removed. The margin (RM) is described as positive when cancer cells are present at the edge of the tissue, suggesting that all of the cancer has not been removed. The margin (RM) can be set based on surgical preferences, imaging data, default settings, tool geometry, and the like. In some examples, the margin (RM) can be: greater than 0 and less than 1 mm; greater than 5 mm and less than 10 mm, or any other margin that is appropriate for the given procedure or patient condition. The defined margins (RM) can affect how the cutting boundary (CB) is oriented or sized relative to the diseased region (DR). The margin (RM) can be uniform or variable in dimension.

At 226, the techniques herein automatically optimize characteristics of the one or more cutting geometries (C) relative to the diseased region (DR). One manner by which optimization is performed is shown at 228, and described in detail below, which is an optimization criterion requiring minimization of an amount of healthy region (HR) to be removed by the one or more cutting boundaries (CB) so as to keep as much of the healthy bone in tact after excision or resection. In practice, the minimization of healthy region (HR) does not necessarily mean total minimization such that no healthy region (HR) is removed. The amount of healthy region (HR) removed can depend on many factors, such as the presence or absence of other constraints on planning, such as en bloc removal 214, access direction (AA), access angle (Aθ), avoiding critical regions 220, avoiding self-intersection 222, and the definition of surgical margins (RM). Another planning constraint may be a requirement that removed region can be filled, e.g., either with an implant or a bone reconstruction material.

After optimization, the cutting boundary (CB) is defined such that the planning phase is largely complete. Using a clinical application 186, which can comprise the non-transitory memory storing the instructions for implementing the described automated planning techniques, the surgeon may be able to define, activate, or deactivate any of the parameters, inputs or criterion described above. The surgeon can also modify the optimized cutting boundary (CB) after its generation. The automated planning methods can be performed preoperatively or intraoperatively.

The automated planning methods may be implemented using any appropriate artificial intelligence or machine learning algorithms, including but not limited to any one or more of the following: supervised, unsupervised or reinforcement learning algorithms, neural networks, convolutional neural networks, support vector machining, Bayesian networks, K means prediction, Gaussian mixture models, Dirchlet processes, Q-learning, R-learning, TD learning, Random Forest, dimensionally reduction algorithms, gradient boosting algorithms, linear or logistic regression, k-nearest neighbors, k-means, evolutionary algorithms, genetic algorithms, particle swarm algorithms, or any combination thereof, or the like.

As will be appreciated from the disclosure herein, the automated planning techniques provide significant advantages over conventional means of planning. The automated techniques herein allow for significant reductions in healthy bone volume removed and overlap with critical structures as compared to baseline conformal cuts, while simultaneously allowing removal of malignant bone tumors with the lesion intact (remaining in one piece) to ensure no tumor cells remain which can cause local recurrence. The accuracy of the automated planning is improved as compared with conventional planning methods which are technically demanding and time-consuming and heavily reliant on surgeon experience and skill. The techniques herein also provide the capability to generate complex 3D cutting geometries where straight cutting planes are not particularly suitable. Furthermore, the techniques provide the automated measurement and comparison of the quality of a cutting plans for achieving optimal results with significantly less time required for planning as compared with conventional approaches.

Sections A and B provide detailed descriptions of two implementations for automated cut planning. The detail provided above can apply to either of the following implementations, in part or in whole. The following implementations are provided as example implementations for automated cut planning and are not intended to limit the scope of this description exclusively to one of these implementations or the other. It is contemplated that the automated planning techniques herein be utilized, in part or in whole, with certain aspects of either of the following implementations or certain aspects of both of these implementations. In view of the description above, it is also contemplated that the automated planning technique be implemented with no aspects of either of the following implementations.

A. Ruled Surface Approach

Described in this section is one example implementation for automated cut planning. For any given surface of the diseased region (DR), the ruled surface technique described herein is adapted to identify or form the ruled surface(s) (RS) to define the cutting boundary (CB) that enables intact removal of the complete diseased region (DR) (as a single piece, en bloc) and that minimizes the volume of bone that is removed along with the diseased region (DR).

Figure 7:
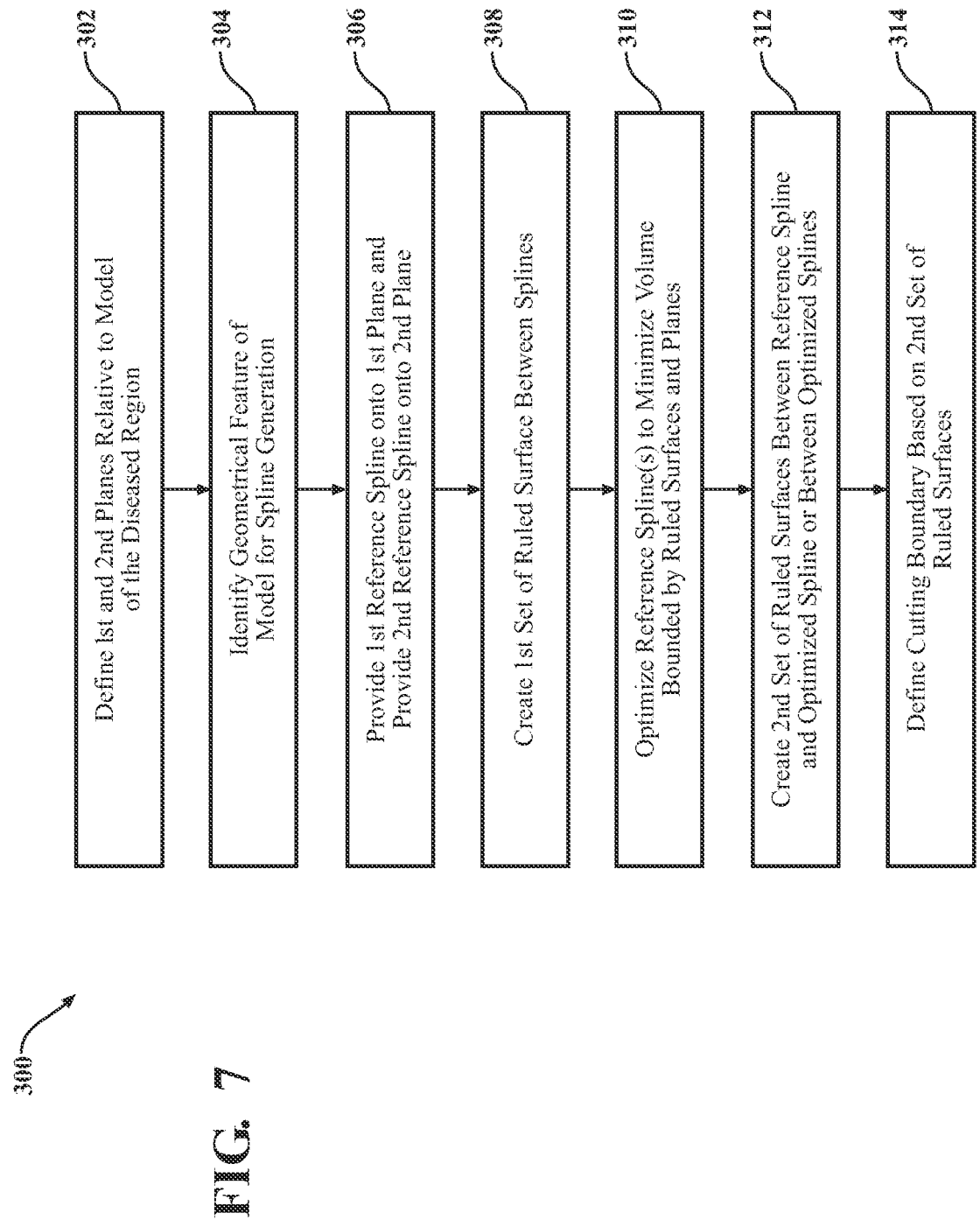
FIG. 7 is a flowchart of one implementation of a ruled surface approach to the automated cut planning techniques described herein, wherein ruled surfaces are utilized to generate cutting boundaries for removal of a diseased region.

In this approach, and with reference to method 300 described in FIG. 7, a first plane (P1) and a second plane (P2), spaced apart from the first plane (P1), are defined relative to the model (M) of the diseased region (DR), at step 302. At step 304, the automated planning technique identifies a geometrical feature (F) of the model (M) of the diseased region (DR). From the geometrical feature (F), and at step 306, a first reference spline (S1) is derived and provided onto the first plane (P1) and a second reference spline (S2) is derived and provided onto the second plane (P2). At step 308, the automated planning technique creates a first set of ruled surfaces (RS1) extending between the reference splines (S1, S2). At step 310, automated optimization of a shape of one or both of the reference splines (S1, S2) is performed to thereby define one or both of an optimized first spline (OS1) and an optimized second spline (OS2). In one implementation, optimizing is based on minimizing a volume bounded by the first set of ruled surfaces (RS1) and the first and second planes (P1, P2). At step 312, the automated planning technique creates a second set of ruled surfaces (RS2) extending between one of the reference splines (S1, S2) and one of the optimized splines (OS1, OS2) or extending between the optimized splines (OS1, OS2). At step 314, the cutting boundary (CB) is defined based on the second set of ruled surfaces (RS2). The enumerated steps can differ from the order listed. For example, the geometrical feature (F) can be defined before the planes (P1, P2) and/or the first spline (S1) can be provided after the second spline (S2). The above steps will be described in greater detail below.

In some implementations, the surface lines of the ruled surfaces (RS) can be limited to an angle, or range of angles, to respect the limited access dictated by the approach axis (AA) and/or angle of access (A$\theta$). To provide manageable cutting boundaries (CB), planning can also be constrained such that no ruled surface (RS) overlaps or intersects itself (no self-intersection). Additional constraints on the ruled surfaces (RS) can be the surgical margin (RM), or any other input, parameter, or criterion as described above.

1. Ruled Surface Computation

Ruled surfaces (RS) are surfaces that can be generated utilizing only straight lines. The rules surfaces (RS) can be created by sweeping a line along a curve, or by joining two curves with straight lines. A ruled surface can be represented parametrically as:

$$x(u,v)=s(u)+v\cdot r(u) \quad [1]$$

in which s(u) is the directrix (base curve) of the surface and r(u) represents the directions of the generating lines (generators), respectively and u, v$\in\mathbb{R}$ (over some interval, defined in further detail below). An alternative form of the parameterization is:

$$x(u,v)=(1-v)\cdot s(u)+v\cdot q(u) \quad [2]$$

in which s(u) is the directrix of the surface (as in equation [1]) and q(u) is a second directrix, given by:

$$q(u,v)=s(u)+r(u) \quad [3]$$

where s(u) is the directrix and r(u) the generators, as previously described.

Figure 8B:
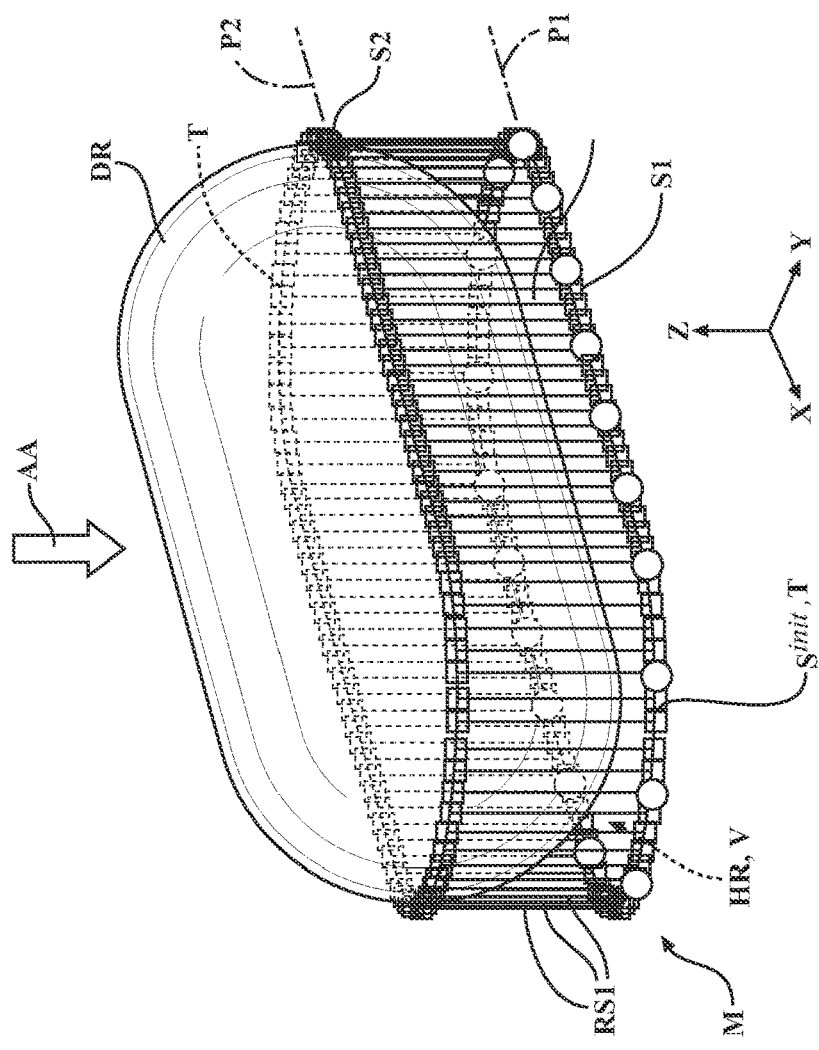
FIGS. 8A and 8B are respective top-down and perspective views of ruled surfaces defined with respect to a model of the diseased region, according to one implementation of a ruled surface approach to the automated cut planning techniques described herein.
Figure 8A:
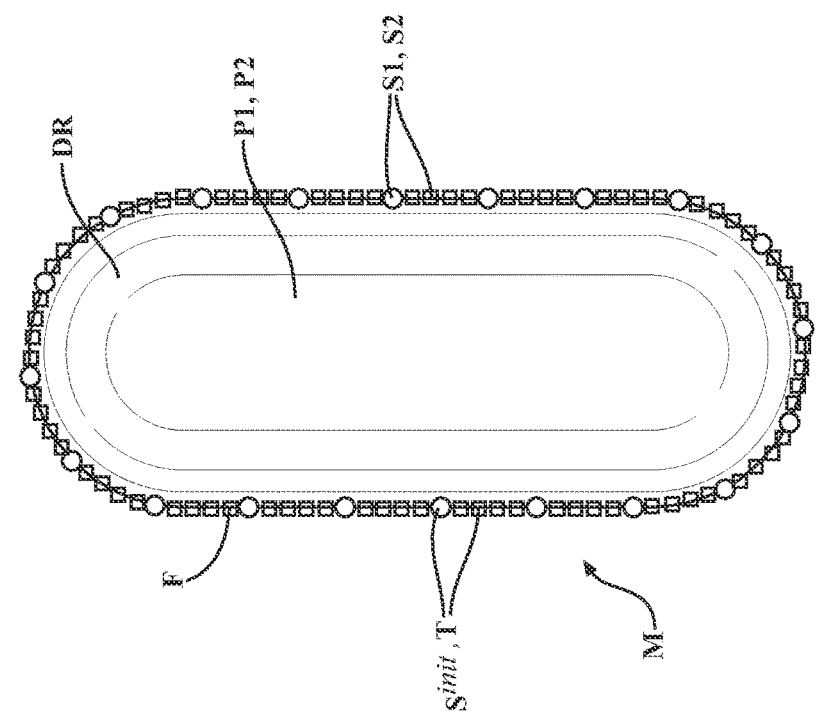

With reference to FIGS. 8A and 8B, the model (M) of the diseased region (DR) is shown for simplicity as a three-dimensional pill-shaped geometry and the healthy region (HR) is not shown. Of course, the model (M) of the diseased region (DR) can have more complex geometry, such as shown in FIGS. 2A-4A, with the adjacent healthy region (HR) present.

The first plane (P1) is defined relative to the model (M) of the diseased region (DR), at step 302. In one implementation, the first plane (P1) can be located at or beyond the limits of the diseased region (DR). For example, the first plane (P1) in FIG. 8B is located beneath the diseased region (DR) to ensure the cutting boundary (CB) will remove the diseased region (DR), en bloc. The automated planning program can identify limits or boundaries of the diseased region, e.g., along the access direction (AA). If the access direction (AA) is aligned to the z-axis, the limits can be at or beyond a nearest coordinate or most-distant coordinate of the diseased region (DR) identified relative to the z-axis and the first plane (P1) can be located in the x-y plane of the coordinate system. In other examples, the first plane (P1) can be oriented perpendicular, coincident, or transverse to the access direction (AA) or in an x-z plane or a y-z plane of the coordinate system. Alternatively, the first plane (P1) can intersect a geometric origin, centroid, center of gravity or other geometrical reference of the diseased region (DR). The first plane (P1) can be located at any other position and/or orientation relative to the diseased region (DR) including above, below or to the side of the diseased region (DR).

At step 304, the automated planning technique identifies a geometrical feature (F) of the model (M) of the diseased region (DR). In the instance where the first plane (P1) intersects the diseased region (DR), the geometrical feature (F) of the model (M) can be derived from the intersection itself. For example, the geometrical feature (F) can be a cross-sectional contour derived from the intersection of the first plane (P1) and the diseased region (DR). In one example, the first plane (P1) is located through the slice of the model (M) possessing the largest cross-sectional surface area or perimeter of the diseased region (DR) so that the geometrical feature (F) is an outermost or largest contour or perimeter of the diseased region (DR). This may be useful to ensure the diseased region (DR) is encompassed for en bloc removal. The automated planning techniques can automatically identify the largest cross-section by scanning the diseased region (DR) of the model (M) using image processing or segmentation techniques.

In other instances, the geometrical feature (F) can be derived from the model (M) of the diseased region (DR) with or without regard to intersection by the first plane (P1). For example, in FIG. 8B, the first plane (P1) is beneath the diseased region (DR) and the geometrical feature (F) can be based on determining a contour or outermost contour of the diseased region (DR) and projecting the contour or outermost contour onto the first plane (P1). In one implementation, the geometrical feature (F) can be computed by projecting mesh vertices of the contour of the diseased region (DR) onto the first plane (P1) and applying a-shapes (a generalization of the convex hull). The geometrical feature (F) can also be derived from predetermined data regarding dimensions (e.g., width, length and/or volume) of the diseased region (DR). These dimensions may include dimensions of the outermost contour of the diseased region (DR). The geometric feature (F) can be proportionally similar to or proportionally larger than any contour, including the outermost contour, of the diseased region (DR). The geometrical feature (F) can be any meaningful geometrical parameter of the diseased region (DR) including, but not limited to: volume, area, surface area, shape, size, contour, length, width, height, perimeter, vertices, diameter or radius, arc, tangent, angle, mass, center of gravity, center of mass, and the like. Any of these parameters can be utilized individually or in combination.

At step 306, a first reference spline (S1) is derived from the geometrical feature (F) and provided onto the first plane (P1). The first reference spline (S1) is the first directrix s(u) from which the ruled surfaces (RS) will be generated. The first reference spline (S1) can be sized to be congruent or larger than the geometrical feature (F) of the diseased region (DR) so as to constructively encompass the diseased region (DR) when viewed from the z-direction. The first reference spline (S1) can be given a shape (e.g., a customized or standard geometrical shape) that either corresponds to or is appropriately sized to encompass the largest perimeter or boundary of the diseased region (DR). Hence, the first reference spline (S1) need not necessarily be directedly derived from the geometrical feature (F), but can be indirectly based on, or sized to, the geometrical feature(s) of the diseased region (DR). In one implementation, wherein the geometrical feature (F) is a cross-sectional contour of the model of the diseased region, the first reference spline (S1) can be generated by projecting the contour onto the first plane (P1). The first reference spline (S1) can be formed to have a contour being congruent to the projected contour. In instances where the projection occurs along the approach axis (AA) (e.g., z-axis), and the first plane (P1) is placed in parallel with the cross-sectional plane from which the contour is derived, the first reference spline (S1) can have identical x-y coordinates to the cross-sectional contour. In some examples, more than the first plane (P1) and hence, more than the one first reference spline (S1) can be defined given the complexity of the geometry of the diseased region (DR).

In one implementation, the first reference spline (S1) is defined as a planar periodic spline (e.g., a closed loop). In other implementations, the first reference spline (S1) can be an open loop spline. This first reference spline (S1) is defined based on the positions of m knots. In one implementation, the first reference spline (S1) is formulated with derivatives and parameterization of monotone piecewise cubic Hermite interpolating polynomials. This formulation is shape-preserving (does not overshoot or oscillate and maintains the monotonicity of a curve), is locally defined (e.g., changes in one knot only affect adjacent knots not the complete shape of the curve), and is fast to compute.

In one non-limiting implementation, wherein the outermost contour of the diseased region (DR) is used for the plane (P1) in FIG. 8B, the first reference spline (S1) or directrix s(u) can be mathematically represented as:

$$s(u) = \begin{bmatrix} f_x(u) \\ f_y(u) \\ \min(tv.z) \end{bmatrix},$$

$\min(tv.z) := \text{minimum } \{v.z | v \text{ vertex of the } DR \text{ mesh}\}$ in which $f_x(u)$ and $f_y(u)$ are the interpolation functions for a monotonic first reference spline (S1), with the functions interpolating the x and y positions of the knots, and u is the distance of the knots along the spline (S1) (i.e. the chord length). Component tv·z is the z component of the diseased region (DR) mesh vertices and min( ) the minimum function as defined above. The knots for the directrix s(u) can be initialized based on the boundary of the diseased region (DR) along the defined access direction (AA). Once computed, m knots can be placed at intervals along the first reference spline (S1). The knots can be spaced equidistantly or non-equidistantly.

With continued reference to FIG. 8B, the second plane (P2) is also defined relative to the model (M) of the diseased region (DR), at step 302. The second plane (P2) is spaced apart from the first plane (P1) to provide spacing for generation of the ruled surfaces (RS). The second plane (P2) in FIG. 8B is located through a center of the volume of the diseased region (DR). However, the second plane (P2) can be located at any other pose relative to the diseased region (DR) including beyond the diseased region (DR). Any of the description above related to how the first plane (P1) is located or defined can apply equally to the second plane (P2) and is not repeated for simplicity in description. In one example, the first plane (P1) is at or below the bottom of diseased region (DR) and the second plane (P2) is at or above the top of the diseased region (DR), when viewed along the z-axis. In another example, the first plane (P1) intersects the diseased region (DR) and the second plane intersects the diseased region (DR). In another example, one of the planes (P1, P2) intersects the diseased region (DR) and the other plane (P1, P2) is located at or beyond the bottom of the diseased region (DR). The first and second planes (P1, P2) can be parallel to one another or non-parallel to one another. The first and second planes (P1, P2) can also intersect each other, or intersect the approach axis (AA). Additionally, it is contemplated that the first and second planes (P1, P2) have a more complex configuration than a planar shape, such as a paraboloid, e.g., elliptical, cylindrical, circular, or spherical paraboloid or any type of hyperboloid. In such scenarios, they can be referred to as first and/or second surfaces, instead of planes. Various configurations of the planes (P1, P2) are contemplated other than those described above.

At step 306, a second reference spline (S2) or second directrix q(u) is established, which is provided onto the second plane (P2). Optionally, the second reference spline (S2), similar to the first reference spline (S2) is derived from the geometrical feature (F) of the model of the diseased region (DR). Any of the description above related to how the first reference spline (S1) is derived from the geometrical feature (F) can apply equally to the second reference spline (S2) and is not repeated for simplicity in description. In one implementation, the second spline (S2) can be a copy of the first spline (S1), or vice versa. The first and second splines (S1, S2) can be congruent to one another, as shown in FIG. 8B, or they can be different. That is, different geometrical features (F) of the diseased region can be utilized to generate the splines (S1, S2). Alternatively, the same geometrical feature (F) can be utilized to generate the splines (S1, S2) but the feature (F) can be applied in different manners or by using certain components of the feature (e.g., using volume for the first spline and using width of the volume for the second spline). In other instances, the splines (S1, S2) whether congruent in shape or not, can be adjusted based on factors such as surgeon preference or input, resection margins (RM), access direction (AA), access angle (AΘ), avoiding critical regions 220, or avoiding self-intersection 222. Also, the first and second splines (S1, S2) can be generated simultaneously or at different times.

At step 308, and as illustrated in FIG. 8B, the automated planning technique creates a first set of ruled surfaces (RS1) extending between the reference splines (S1, S2). In one implementation, the generator directions r(u), along which the ruled surface (RS1) will be generated, are defined by interpolating p (where p=i·m, i∈ℕ) points along the first reference spline (S1) or first directrix s(u) resulting in the point set $S^{init}$. In the example of FIG. 8B, the initial points from the first spline (S1) are translated from the first plane (P1) to the second plane (P2), resulting in a second point set T (subsequently referred to as the reference point set). Thus:

$$T=S^{init}-[0,0,\min(tv\cdot z)] \quad [5]$$

The first set of ruled surfaces (RS1) are generated such that each ruled surface of the first set (RS1) has vertices defined by adjacent points in the first reference point set $S^{init}$ and respective adjacent points in the second reference point set T.

At step 310, automated optimization of a shape of one or both of the reference splines (S1, S2) is performed to thereby define one or both of an optimized first spline (OS1) and an optimized second spline (OS2). The method is configured to optimize only the first spline (S1), only the second spline (S2), or both splines (S1, S2). The first spline (S1), if optimized, becomes the optimized first spline (OS1) and the second spline (S2), if optimized, becomes the optimized second spline (OS2).

Figure 9B:
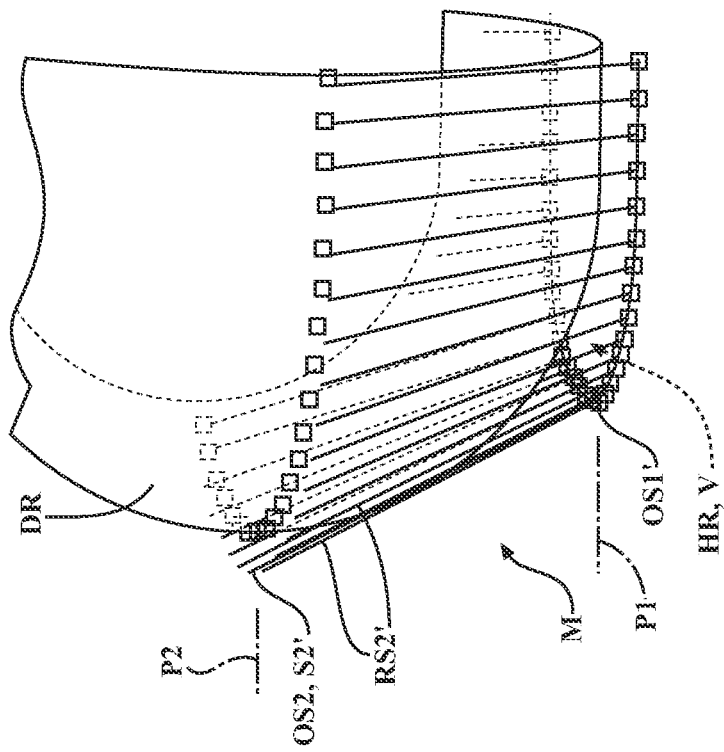
FIG. 9B illustrates the view of model of the diseased region of FIG. 9A with ruled surfaces being further optimized, or partially optimized, to avoid intersections with diseased region, according to one implementation.
Figure 9A:
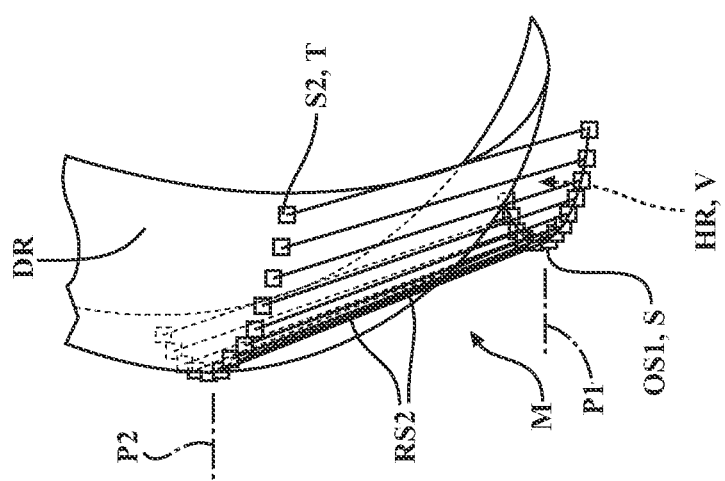
FIG. 9A is a partial-perspective view of the model of the diseased region of FIG. 8 with ruled surfaces being optimized, or partially optimized, to fit the diseased region and minimize removal of healthy region adjacent to the diseased region, according to one implementation.

In one implementation, the optimizing of one or both splines (S1, S2) is based on minimizing healthy region (HR) defined within or bounded by a volume (V). This is performed to reduce the amount of healthy bone removal. For example, in FIG. 8B, the healthy region (HR) surrounds the lower portion of the diseased region (DR). A portion of the healthy region (HR) is bound within the volume (V) defined by the first set of ruled surfaces (RS1) and the first and second planes (P1, P2). The healthy region (HR) can alternatively be bound by one plane or by more than two planes. During this optimization process, the first spline (S1) or second spline (S2) may shrink in size to fit to the diseased region (DR). In one example, as shown in FIG. 9A, the knots of the first spline (S1) from FIG. 8C are moved and points $S^{init}$ become S, a point set containing p points interpolated along s(u) where at least one of the knots of s(u) has been shifted from its initial position. This is subsequently referred to as the optimization point set of the optimized first spline (OS1). If the second splines (S2) is optimized, then the process would similarly yield an optimization point set of the optimized second spline (OS2). In one implementation, minimizing the volume of healthy region (HR) to be removed can be implemented as follows. A minimization metric of the volume of healthy region (HR) can be calculated for two iterations of the volume (V). If the second calculated metric is better than the previous first iteration, new knot positions for the first spline or second spline (S1, S2) are confirmed and the optimization algorithm moves onto the next knot. If the computed metric is worse than the previous best the step size is decreased, and the knot is returned to its previous position and the optimization algorithm moves onto the next point. Once all knots have been shifted and checked the optimization algorithm repeats until there is no improvement in the computed metric. This computation can be implemented using machine learning algorithms, such as neural networks.

At step 312, and as shown in the example of FIG. 9A, the automated planning technique creates a second set of ruled surfaces (RS2) extending between one of the reference splines (S1, S2) and one of the optimized splines (OS1, OS2) or extending between the optimized splines (OS1, OS2). If only the optimized first spline (OS1) is generated, such as in FIG. 9A, then the second set of ruled surfaces (RS2) are defined or re-defined between the optimized first spline (OS1) and the second spline (S2). In other words, p generator lines are generated between the corresponding adjacent points in the S (optimization) and T (reference) point sets. If both the optimized first and second splines (OS1, OS2) are generated, then the second set of ruled surfaces (RS2) are defined or re-defined between the optimized first spline (OS1) and the optimized second spline (OS2). In other words, p generator lines are generated between the corresponding adjacent points in two different S (optimization) point sets. The second set of ruled surfaces (RS2) can replace or modify the first set of ruled surfaces (RS1).

In one optional implementation, a shape of one or both of the reference splines (S1, S2) and/or one or both of the optimized splines (OS1, OS1) can be further optimized to avoid intersections of any ruled surfaces (RS1, RS2) with the model of the diseased region (DR). This step can be implemented at the stage after the first set of ruled surfaces (RS1) are defined (e.g., FIG. 8B, step 308) and/or at the stage after the second set of ruled surfaces (RS2) are defined (e.g., FIG. 9A, step 312). The optimization algorithm determines that one or more ruled surfaces (RS1, RS2) intersects the diseased region (DR) and then adjusts position and/or orientation of the one or more of the ruled surfaces (RS1, RS2) to not intersect the diseased region (DR). In turn, this adjustment will adjust the shape of one of the reference splines (S1, S2) and one of the optimized splines (OS1, OS1) or a shape of both optimized splines (OS2, OS2). Optimization based on minimization of volume of the bounded healthy region (HR) causes the second set of ruled surfaces (RS2) to intersect the diseased region (DR). In response, and as shown in FIG. 9B, the algorithm iteratively reorients each generator line such that it no longer intersects the diseased region (DR). In one example, this process creates a set of p generators R, from which we can recover r(u) by interpolating between the R generators using, e.g., spherical linear interpolation. In one implementation, normals in the respective plane (P1, P2) at each knot are calculated and each knot is moved inwards along its normal by a defined step size. As a result, a modified version of the second spline (S2') and/or optimized first spline (OS1') are generated with a modified version of the second set of ruled surfaces (RS2'), which closely capture the diseased region (DR) but do not intersect such. The modified version of the second spline (S2') can be understood as an optimized second spline (OS2). This adjustment may cause an increase or decrease in the amount of volume of healthy region (HR) to be removed. The intersection avoidance process can be implemented using means other than that described herein.

In one optional implementation, a shape of one or both of the reference splines (RS1, RS2) and/or one or both of the optimized splines (OS1, OS1) can be further optimized to avoid intersections through defined critical or no-go regions (N) or zones of the anatomy (A). Such regions are those beyond the diseased region (DR) and located in the healthy region (HR), which should be avoided by the cutting boundary (CB) to prevent removal of the critical structure. One example is shown in FIG. 3B, wherein the articulating surface of the tibia is defined as a no-go region (N). This step can be implemented at the stage after the first set of ruled surfaces (RS1) are defined (e.g., FIG. 8B, step 308) and/or at the stage after the second set of ruled surfaces (RS2) are defined (e.g., FIG. 9A, step 312). The optimization algorithm determines that one or more ruled surfaces (RS1, RS2) intersects the no-go region (N), or more specifically, a virtual boundary associated with the no-go region (N) that is provided in the model (M). The optimization algorithm adjusts position and/or orientation of the one or more of the ruled surfaces (RS1, RS2) to not intersect the no-go region (N). Modification of the splines can be implemented using an iterative process that moves each knot inwards or outwards until the criterion is met. In turn, this adjustment will adjust the shape of one of the reference splines (RS1, RS2) and one of the optimized splines (OS1, OS1) or a shape of both optimized splines (OS2, OS2). This adjustment may cause an increase or decrease in the amount of volume of healthy region (HR) to be removed. The no-go avoidance process can be implemented using means other than that described herein.

Optimization after step 308 or step 312 may be performed to account for the access angle (Aθ). The automated approach can adjust position and/or orientation of the one or more of the ruled surfaces of the first set (RS1) to not exceed the access angle (Aθ) thereby adjusting the shape of one or both reference splines. For example, with respect to FIG. 8, if access angle (Aθ) is defined by a conical volume with a 45 degree angle and a vertex of the cone being below the diseased region (DR) and the base of the cone being above the diseased region (DR), the first spline (S1) can be automatically tapered inwards to be within the boundary of the cone. The algorithm can identify intersections with the angle (Aθ) boundary and modify any splines or ruled surfaces accordingly. In one implementation, the direction in R is checked to make sure it is within the defined angle limit. If it is outside of the range the step size is decreased, the knot is returned to its previous position and the algorithm moves onto the next point. If all orientations are within the angle range, the optimization metric is calculated for the new cut surface: if the metric is better than the previous best the new knot position is confirmed and the algorithm moves onto the next knot. If the computed metric is worse than the previous best the step size is decreased, the knot is returned to its previous position and the algorithm moves onto the next point. This approach can also be implemented with respect to the optimized first spline (OS1) and/or the optimized second spline (OS2) after optimization for minimizing volume occurs. Optimization for access angle (Aθ) process can be implemented using means other than that described herein.

Figure 2B:
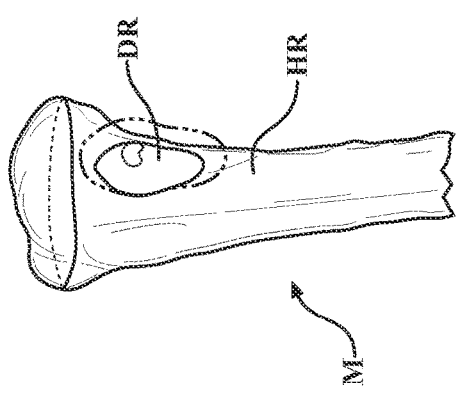
Figure 3B:
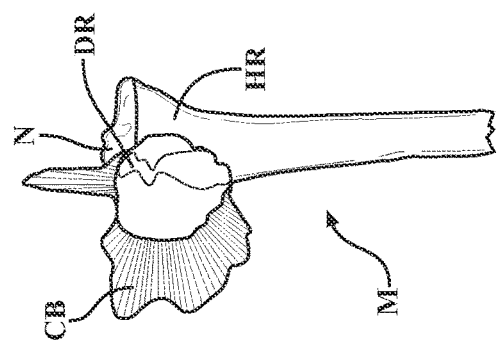
Figure 4B:
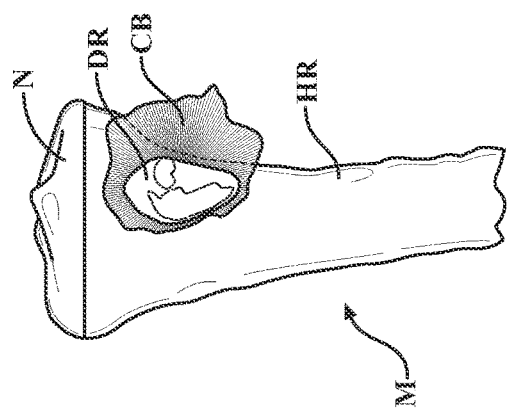

After any combination of the optimizations described above are implemented, the result will be the second set of ruled surfaces (RS2), which may be in original form, or modified or regenerated based on further optimizations. At this point the cutting boundary (CB) can be defined at step 314, wherein some examples of cutting boundaries (CB) are illustrated in FIGS. 2B, 3B and 4B.

Figures 10, 11:
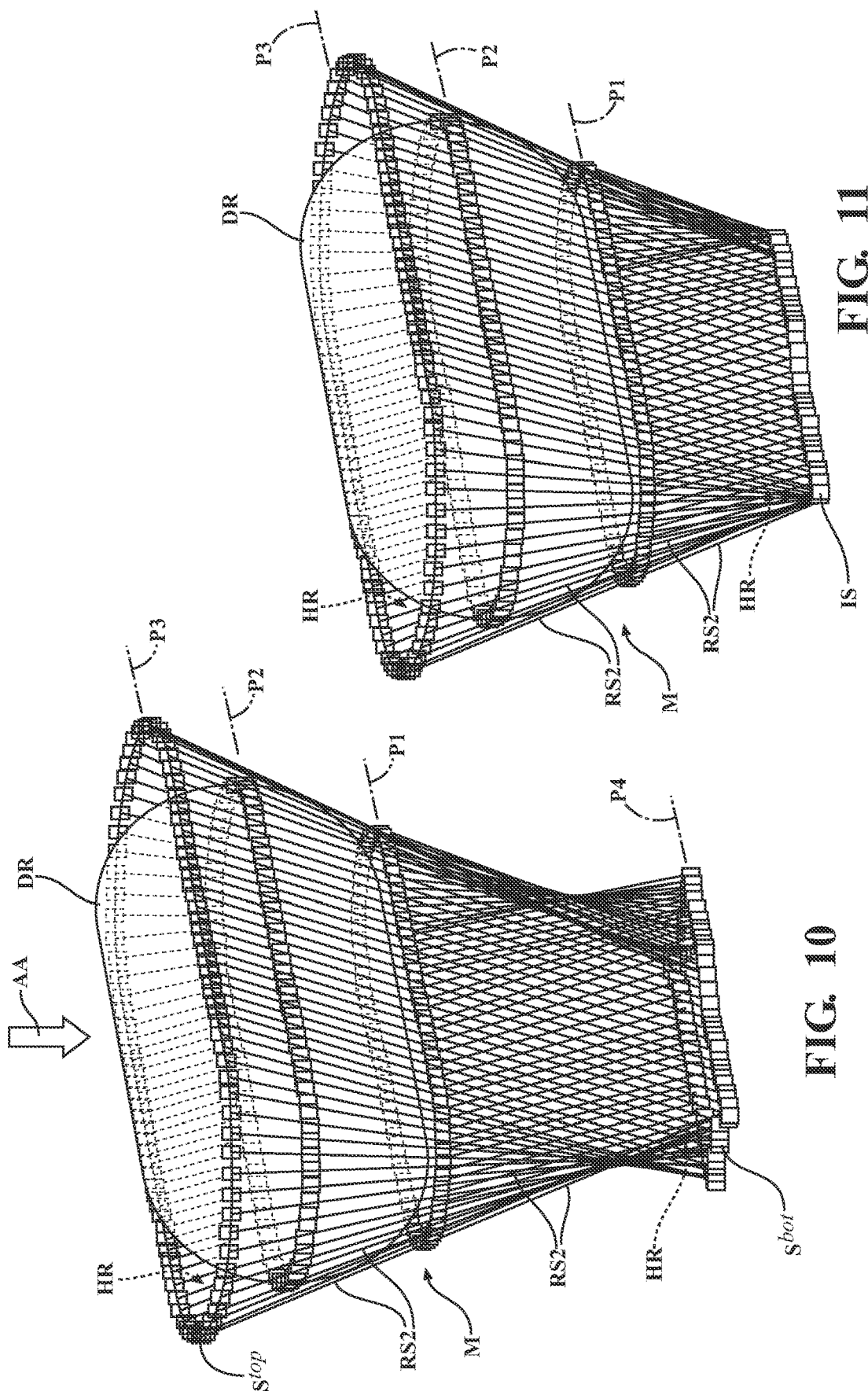
FIG. 10 illustrates the model of the diseased region of FIG. 9B with ruled surfaces being further optimized, or partially optimized, to extend beyond the limits of the ruled surfaces of FIG. 9B, according to one implementation.
FIG. 11 illustrates the model of the diseased region of FIG. 10 with ruled surfaces being further optimized, or partially optimized, to avoid self-intersection, according to one implementation.

It is contemplated to further modify the cutting boundary (CB) further for visualization and evaluation purposes. Specifically, with reference to FIGS. 10 and 11, the algorithm can define a third plane (P3) above the second set of ruled surfaces (RS2) with reference to the z-axis. Here, the second set of ruled surfaces (RS2), which were generated after step 314, are extended along respective generator lines to the third plane (P3). A fourth plane (P4) can then be defined below the second set of ruled surfaces (RS2) with reference to the z-axis. The second set of ruled surfaces (RS2) are extended along respective generator lines to the fourth plane (P4). The third and fourth planes (P3, P4) can be defined based on geometric features (F) of the diseased region (DR), using any implementation described above related to positioning of the first and second planes (P1, P2). One or both of the third and fourth planes (P3, P4) can intersect the diseased region (DR) or be located past the diseased region (DR). In one implementation, the z-axis of a coordinate system of the model (M) is aligned to the approach axis (AA), as shown in FIG. 10. The algorithm defines the planes (P3, P4) by identifying an uppermost and a lowermost reference or coordinate of the healthy region (HR) of the model relative to the z-axis. The third plane (P3) can be defined at or above the uppermost reference or coordinate and the fourth plane (P4) can be defined at or below the lowermost reference or coordinate of the model of healthy region (HR). This can be performed to expand the cutting boundary (CB) to account for practical constraints involved with surgically removing the diseased region (DR) with the tool and/or for accounting for an entirety of the diseased region (DR) up to the limits of the healthy region (HR) in instances where the second set of ruled surfaces (RS2) were generated with insufficient length. Furthermore, this process can assist the evaluation of the cutting boundary (CB) to be performed quickly enough that iterative optimization is feasible.

In one non-limiting implementation, the ruled surface extension computation can be performed as follows: on the directrix s(u) we have p interpolation points (elements of the point set S) and its associated generators R. The S points and R generators are used to define two new point sets $S^{top}$ and $S^{bot}$ by extending from S along R to the third plane (P3) above and fourth plane (P4) below the surface of the bone, such that:

$$S^{top} = S + d_{top} R \qquad [6A]$$

$$S^{bot} = S - d_{bot} R \qquad [6B]$$

where $d_{top}$ and $d_{bot}$ are the distances along each R from each point in S to the top and bottom planes (P3, P4), respectively, given a sub-case of the line-plane intersection equation in which the plane is parallel to the z-axis:

$$d_{top} = \frac{\max(bv.z) - S.z}{R.z}$$

$$d_{bot} = \frac{\min(bv.z) - S.z}{R.z}$$

in which max(bv·z) and min(bv·z) are the maximum and minimum z coordinates of the bone model (M) mesh vertices, respectively and S·z and R·z are the z components of the interpolation points and generators.

With reference to FIG. 11, the algorithm performs a process to ensure no cutting boundary (CB) intersects itself. Self-intersection can be addressed by proactively avoiding self-intersections or by allowing the self-intersection and removing portions of the cutting boundary (CB) that self-intersect. In one implementation, the algorithm identifies locations of intersections among the second set of ruled surfaces (RS2) occurring from extending the second set of ruled surfaces (RS2) to the fourth plane (P4). An intersection reference geometry is defined based on the identified locations of intersections. For example, in FIG. 11, the intersection reference geometry can be an intersection spline (IS) which is spline defined through points of self-intersection. The intersection reference geometry need not be a spline, or confined to a plane, as shown in FIG. 11. Instead, the intersection reference geometry can be any type of line, surface, point cloud, or complex geometry to provide some type of bounding property. The algorithm then defines the cutting boundary (CB) based on the second set of ruled surfaces (RS) extending between the third plane (P3) and the intersection reference geometry (IS).

In one non-limiting implementation, the self-intersection computation can be performed as follows: $S^{bot}$ is modified to remove self-intersections: adjacent pairs of $S^{top}$ and $S^{bot}$ points are converted to triangles and the intersections between the generator lines R and these triangles computed. $S^{bot}$ is modified such that it does not extend beyond the intersection with the closest triangle. This intersection process introduces approximation errors into $S^{bot}$ so the final step is to filter these points, smoothing the overall cutting surface. A two-dimensional weighted average filter is applied, with weights given by:

$$w_i^j = N(0, \sigma, \|S_i^{bot} - S_j^{bot}\|) \quad [8]$$

in which $w_i^j$ is the weight for point j relative to point i and $N(0,\sigma,\|S_i^{bot}-S_j^{bot}\|)$ is a sample of the normal distribution centered at 0, with a standard deviation of $\sigma$, taken at the 2d Euclidean distance $(\text{dist}(p,q):=\sqrt{(p\cdot x - q\cdot x)^2 + (p\cdot y - q\cdot y)^2})$ between the two points. The use of the 2d Euclidean distance means that differences in height between the points are ignored when calculating these weights. Thus, a single filtered position is calculated as the weighted average of the curve positions:

$$S_i^{bot} = \frac{\sum_{j=1}^{p} w_i^j S_j^{bot}}{\sum_{j=1}^{p} w_i^j}$$

After filtering, the line is reprojected, and the orientation and intersection recalculated, the ruled surface candidate is shown in FIG. 11.

2. Definition of Optimization Metric and Computation of Removed Volume

As previously described, the techniques described herein aim to find the ruled cutting surface that minimizes the volume of healthy region (HR) that is removed while optionally not passing through defined no-go regions (N). Thus, in one non-limiting implementation the value to be minimized can be defined as follows:

$$M = V_{bone}^{(1+V_{nogo})} \quad [10]$$

in which M is the optimization metric, $V_{bone}$ is the volume of bone removed by the cutting boundary (CB) and $V_{nogo}$ is the volume of the no-go regions (N) removed by the cutting boundary (CB), respectively. This metric can be read as follows: in the case where there is no interference with a no-go region (N) or no regions are defined (i.e. $V_{nogo}=0$), the metric is simply the volume of bone removed ($M=V_{bone}$); in cases in which there is some volume of no-go region (N) removed (i.e. $V_{nogo}>0$), M increases exponentially with the amount of no-go volume (N) removed.

Computation of $V_{bone}$ and $V_{nogo}$ requires the computation of the 3D intersection between the cutting boundary (CB) and bone/no-go meshes. As 3D intersection operations can be utilized for 3D intersection computation. Alternatively, an approach can be used for volume approximation based on the sum of area intersections (Cavalieri's principle) and the application of Simpson's rule as follows.

First, the bone and no-go meshes are sliced along the reference axis (AA) in steps of 1 mm (finer slice values can be used if better approximations are required), providing a set of n planar intersection contour sets for both the bone and no-go regions. Each of the n contour sets may contain more than one enclosed contour. This mesh slicing process is performed once as part of the data preparation and setup.

For each new ruled surface cut candidate, the surface is sliced along the same axis and at the same positions as the meshes, providing an additional set of n contour sets, representing the shape of the ruled surface at each slice position. This can be performed in the same manner as the extension of the ruled surface described above, with the z position of each slicing plane in place of min(bv·z) or max(bv·z).

Figure 12A:
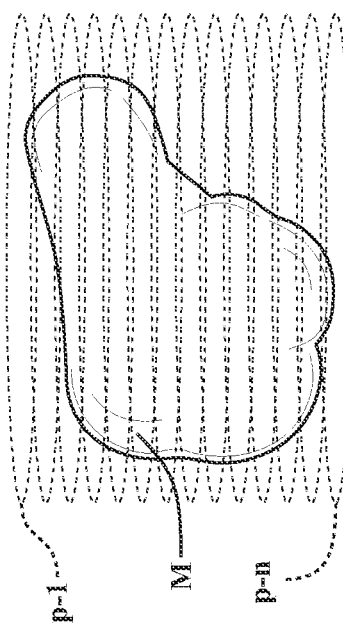
FIGS. 12A-12F illustrate one implementation of computation of removed volume of the anatomy, wherein in FIG. 12A the bone model is sliced.
Figure 12B:
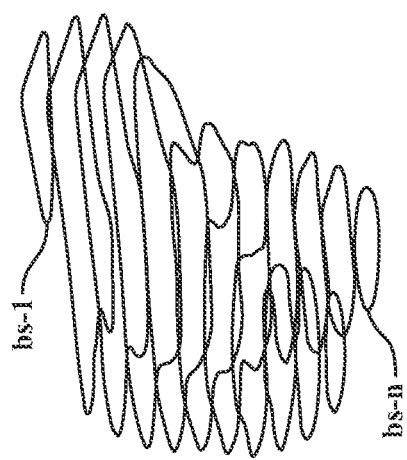
Figure 12C:
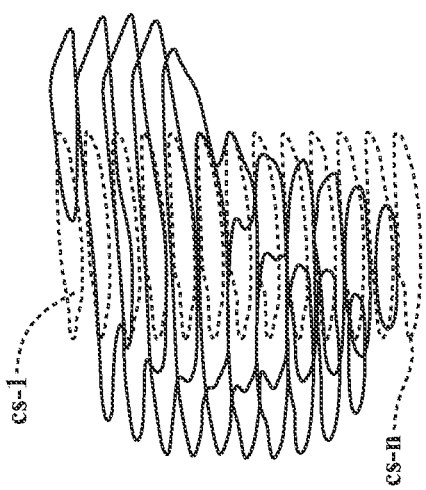
Figure 12D:
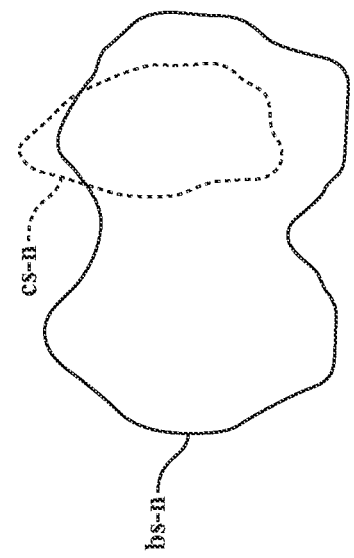
Figure 12E:
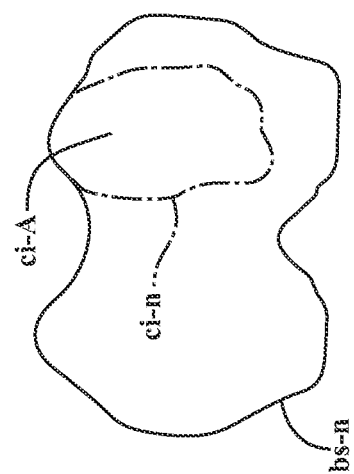
Figure 12F:
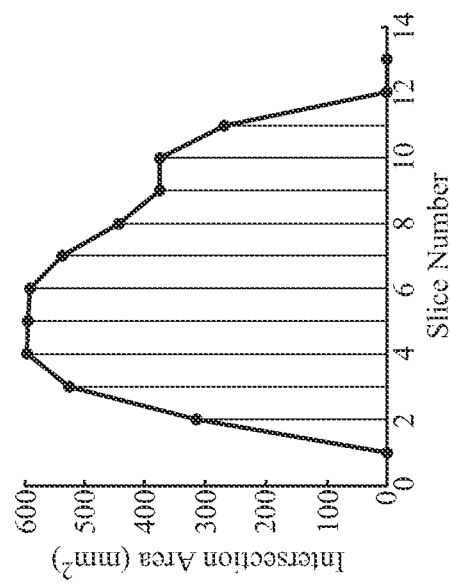

For each of the n contour sets the area of intersection between the planar cut and bone contours is computed:

$$A_i = \text{Area}(BS_i \cap CS_i) \quad [11]$$

in which $BS_i$ and $CS_i$ are the i-th sets of bone and cut surface contours, respectively and $A_i$ represents the area of intersection. The total bone volume removed is then approximated using Simpson's rule:

$$V_{bone} \approx \frac{1}{3}(A_0 + 4A_1 + 2A_2 + 4A_3 + 2A_4 \ldots + 2A_{n-2} + 4A_{n-1} + A_n)$$

in which $V_{bone}$ is the approximated bone volume removed by the cut, n is the total number of slices of the bone model (M) mesh and $A_{0 \ldots n}$ are the intersection areas as defined in eq. [11]. This process is repeated for computation of the removed volume of no-go regions and is shown in FIGS. 12A-12F, illustrating one instance of the volume approximation process, with reduced number of slices for visualization purposes. In FIG. 12A, during the initial case setup process the bone model (M) mesh is sliced with evenly spaced planes (p1-pn) resulting in 'n' bone slice contours (bs), as shown in FIG. 12B. In FIG. 12C, during optimization each ruled surface (RS1, RS2) cut candidate is sliced with the same planes, resulting in 'n' cut slice contours (cs). Contour pairs (bs, cs) are identified in FIG. 12D. For each of the contour pairs (bs, cs), a contour intersection (ci) is computed and the area of this intersection (ci-A) contour computed, as shown in FIG. 12E. The volume is then computed using Simpson's rule for numerical approximation of integrals, as shown in FIG. 12F.

3. Approach Evaluation and Results

Figure 3A:
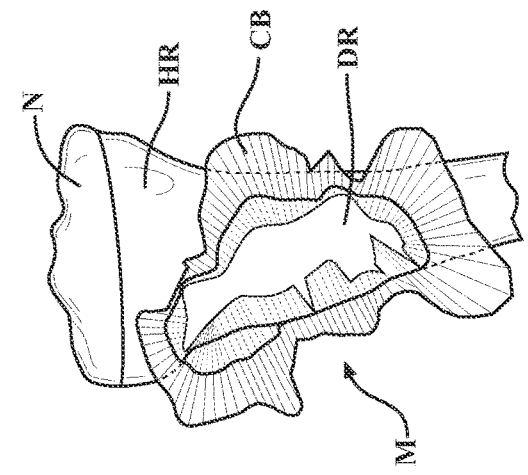
Figure 4A:
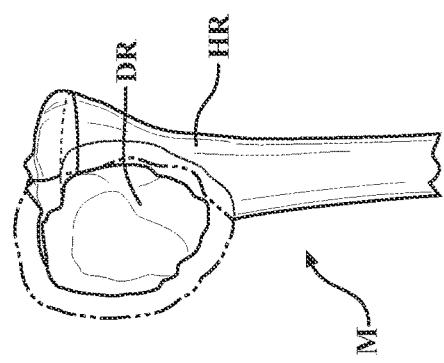

With reference to FIGS. 2-4, several example cases were utilized for evaluation of the described approach. As primary bone tumors often occur in the metaphysis of the long bones, particularly around the knee, cases in this area were utilized. All cases were based on real patient data, acquired with permission from the local ethical review board (approval ID: LNR/18/SVHM/21). Anonymized CT and MRI data were acquired and processed according to the approach described above. In all cases the articular surface of the bone was defined as a critical area (N) to be avoided. The access direction (AA) was defined as approximately anterior-posterior. However, a lateral-medial approach can also be utilized. A maximum access angle (A$\theta$) of 45° was defined for all cases. Ruled surface cuts were generated with margins (RM) of 0 mm (i.e. the tumor as segmented) and 10 mm. A summary of the parameters and values used is follows: number of knots—20; number of generator directions—100; filter standard deviation—1; maximum step size (mm)—0.25; step size decrease factor—0.8; slice thickness for volume calculation (mm)—1; maximum access angle (°)—45; margin (mm)—0/10. To determine the quantity of bone saved when utilizing the defined approach, optimized results were compared to single directional conformal cuts i.e. conformal cuts performed around the tumor along the access direction (AA). These cuts represent a baseline that is achievable using a robotic system with limited surgical site access.

Results for each of five test cases with margins (RM) of 0 and 10 mm are shown in the Tables of FIGS. 13 and 14, respectively. Improvement in bone volume removed ranged from 0.3% to 26.3% in the zero margin cases, and 0.0% to 15.2% in the 10 mm margin cases. Mean improvements of 8.1±10.9% and 4.7±6.3% were observed. Overall differences between initial and optimized bone volumes removed were statistically significant for pooled data (2-tailed paired t-test, p=0.043). Improvement in no-go volume removed varied from 0% (in cases where no interference with no-go regions was observed) to 100% (no intersection with no-go regions after optimization). The results at zero and 10 mm margins (RM) are summarized in the tables of FIGS. 13 and 14, respectively.

B. Evolutionary Algorithm Optimization

Described in this section is another example implementation for automated cut planning. For any given surface of the diseased region (DR), the evolutionary algorithm technique described herein is adapted to identify or form the cutting boundary (CB) that enables intact removal of the complete diseased region (DR) (as a single piece, en bloc) and that minimizes the volume of bone that is removed along with the diseased region (DR). Any of the description or features of the ruled surface technique described above can be implemented or applied relative to the evolutionary algorithm approach described herein, and vice-versa.

In this approach, and with reference to method 400 shown in FIG. 15, the computer-implemented method for automated planning of a cutting boundary (CB) for removal of a diseased region (DR) of an anatomy utilizes a model (M) of the diseased region (DR) and a healthy region (HR) as well as a cutting surface (CS) defining a region to be removed from the anatomy. The cutting surface (CS) is a planned virtual constraint on tool movement and/or operation. Although one cutting surface (CS) is described for simplicity, it will be understood that any number of cutting surfaces (CS) are contemplated for use in this algorithm. As will be described below, the cutting surfaces (CS) can be the same type or shape or different types or shapes. The terms cutting boundary (CB) described above for the ruled surface approach can be utilized interchangeably with cutting surface (CS) described herein.

At step 402, the cutting surface (CS) is placed relative to the model (M). Just as with the Ruled Surface approach, the model (M) is a three-dimension model and the model (M) and the cutting surface (CS) are positioned in a three-dimensional coordinate system. In one implementation, the cutting surface (CS) is placed such that the diseased region (DR) is included in the region to be removed from the anatomy. Virtual placement of the cutting surface (CS) can be automated or manual or a hybrid of both automated and manual input. When manual, the surgeon or planner can use the clinical application to place the cutting surface (CS) relative to the diseased region (DR). When automatic, placing the cutting surface (CS) relative to the model can be performed by the optimization algorithm evaluating feature(s) of the diseased region (DR). For example, the optimization algorithm may automatically identify a most-distant point of the model of the diseased region (DR) determined relative to an axis of the three-dimensional coordinate system, such as the Z-axis aligned with the approach axis (AA). The most-distant point can be below the diseased region (DR) such that when cutting is performed relative to the cutting surface (CS), the entire diseased region (DR) is removed. The optimization algorithm, in other cases, can automatically place the cutting surface (CS) at an arbitrary location outside of a boundary of the model of the diseased region (DR). The arbitrary location can be any distance away from the perimeter, or outer contour of the diseased region (DR) and on any suitable side of the diseased region (DR). The optimization algorithm, in other cases, can automatically place the cutting surface (CS) through the diseased region (DR) at any suitable reference of the diseased region (DR), such as through a centroid or a center of mass of the model of the diseased region (DR). Other examples of how the cutting surface (CS) can be placed are fully contemplated.

One input to the optimization algorithm is a cutting criterion, at step 404, requiring that the cutting surface (CS) be planned for removal of an entirety of the diseased region (DR) as a single piece, en bloc (see also 214, FIG. 1, FIG. 6). That is, the final solution of the cutting surface (CS) generated by the optimization algorithm will ensure removal of the entire diseased region (DR), assuming a surgical tool accurately cuts relative to the cutting surface (CS). The cutting criterion can be part of the optimization algorithm if not initially satisfied based on initial placement of the cutting surface (CS) relative to the diseased region (DR). Otherwise, the cutting criterion can separate from the optimization algorithm if initially satisfied based on initial placement of the cutting surface (CS) relative to the diseased region (DR).

At step 406, an optimization criterion is defined that minimizes an amount of healthy region (HR) to be removed by the cutting surface (CS). This optimization criterion serves as an input to the optimization algorithm such that the cutting surface (CS) is sized, shaped, positioned, and/or oriented to minimize the amount of healthy region (HR). The optimization criterion can be defined or modified at any time during planning, including prior to placing the cutting surface (CS) at step 402. The optimization criterion can be set to a volume, mass, area, surface area or any other mathematical form of measurement to determine the amount of healthy region (HR). The amount of healthy region (HR) can also be assessed using voxels, mesh analysis, or any type of image processing technique for evaluating the relationship between the cutting surface (CR) and the model (M). The optimization criterion can be set to any suitable value, threshold, limit or range of values, from 0 (i.e., no healthy region should be removed) to "N" (i.e., no more than "N" amount of healthy region should be removed). The optimization criterion can be implemented as any objective function that maps an event or values of one or more variables onto a real number to represent some cost or benefit associated with the event. The objective function can be a loss function, cost function, fitness function, utility function, or any version thereof.

The optimization criterion can also take into account any of the planning inputs, criterion and constraints described above, and shown in FIG. 1, including but not limited to, access direction (AA), angle access (Aθ), avoiding no-go region (N), avoiding self-intersections, or obeying surgical margins (RM). These planning constraints can be implemented according to any of the techniques described above and are not repeated in this section for simplicity.

At step 408, the optimization algorithm is executed. The optimization algorithm, in one implementation, is an evolutionary algorithm, or optimization technique based on ideas of evolution, which can use mutation, recombination, and/or selection applied to a population of candidate solutions in order to evolve iteratively better and better solutions. In one implementation, the optimization algorithm is a particle swarm optimization algorithm, or any version or equivalent thereof. Other types of algorithms are contemplated such as genetic algorithms, ant colony optimization, differential evolution, artificial bee colony, glowworm swarm optimization, and cuckoo search algorithm, or the like.

At step at 410, the optimization algorithm initializes, relative to the cutting surface (CS), candidate solutions (or phenotypes) influencing characteristics of the cutting surface (CS). Each candidate solution has a set of properties (e.g., genotype) which can be mutated and altered. Candidate solutions can influence the size, shape, position and/or orientation of the cutting surface (CS). These candidate solutions are associated with the cutting surface (CS) in a mathematical or virtual sense. Candidate solutions can be represented in binary or other encodings. In some implementations, the candidate solutions are initialized as random set, as a pseudo-random set, or as a predefined set of candidate solutions. The candidate solutions can be initialized by considering planning inputs, criterion and constraints described above.

At step 412-418, the optimization algorithm iteratively performs a sequence of sub-steps until the candidate solution is identified that satisfies the optimization criterion, and optionally, other constraints described above.

At step 412, the optimization algorithm evaluates fitness of each of the candidate solution relative to the optimization criterion, and optionally, other constraints described above. In one sense, the population of candidate solutions in each iteration called a generation. In each generation, the fitness of every candidate solution in the population is evaluated. The fitness may be a value of the objective function in the optimization criterion to be satisfied. One or more of the properties, i.e., size, shape, position and/or orientation, of each candidate solution can be used in the fitness evaluation.

In regards to evaluating the fitness of each candidate solution relative to the other planning constraints, the optimization algorithm can be modified to include one or more criteria specific to each planning constraint that penalizes or rewards one or more of the candidate solutions For example, there can be a penalty or reward based on quantitative and/or qualitative evaluation or compliance of each candidate solution relative to one or more of the following: access direction (AA), angle access (A$\theta$), avoiding no-go region (N), avoiding self-intersections, or obeying surgical margins (RM).

At step 414, the optimization algorithm, for the given generation, identifies, among the candidate solutions, the candidate solution best fit to the optimization criterion and optionally, other constraints described above. This step can be implemented by comparing the values of each candidate solution relative to the optimization criterion and choosing the best value among the candidates.

At step 416, the optimization algorithm assesses whether the optimization criterion is satisfied based on the candidate solution best fit to the optimization criterion, identified from step 414. Here, the term "best" does not necessarily mean absolute best solution but refers to the best solution among the candidates from the specific generation. If the identified candidate solution from step 414 is from an early or initial generation it is likely that the optimization criterion will not be yet satisfied. If so, the optimization algorithm determines that the optimization criterion is not yet satisfied at step 416, and proceeds to step 418. If the optimization criterion are satisfied, e.g., after only one generation, the optimization algorithm proceeds to step 420, which will be described below.

At step 418, the optimization algorithm updates, relative to the cutting surface (CS), the candidate solutions based on the candidate solution best fit to the optimization criterion based on the previous generation, identified from step 414. Here, the best fit candidate solution is stochastically selected from the population of the previous generation, and each candidate solution's genome is modified (recombined and possibly randomly mutated) to form a new generation. The updating can include generating a new random set of candidate solutions, which include properties that are slightly modified or tuned based on the properties of the candidate solution identified at step 414 from the previous generation. For a swarm implementation, tuning can include changes to candidate solution quantity, acceleration constant, inertia weight and/or maximum limited velocity. The new generation of candidate solutions is then used in the next iteration of the optimization algorithm.

The optimization algorithm then repeats steps 412, 414, and 416 with respect to the new generation to determine whether the best candidate solution for the new generation satisfies the optimization criterion. The optimization algorithm terminates the generation loop when a best candidate solution is identified which possesses satisfactory fitness level with respect to the optimization criterion, and optionally, other planning constraints. The optimization algorithm can also terminate the generation loop when a predetermined number of generations has been produced. This predetermined number of generational loops can be defined by the surgeon using the clinical application or can be defined automatically by the optimization algorithm.

Once the optimization criterion is satisfied by the identified best candidate solution, e.g., after N generations, the optimization algorithm proceeds to step 420, in which the optimization algorithm automatically modifies characteristics of the cutting surface (CS) based on the identified candidate solution that satisfies the optimization criterion. The modified cutting surface (CS) will comprise properties different from the cutting surface (CS) initially placed relative to the diseased region (DR), at step 402. The cutting surface (CS) is modified based on the properties (e.g., size, shape, position and/or orientation) of the identified candidate solution satisfying the optimization criterion. In one implementation, step 420 is performed by the updating step 418 for the last generation. Alternatively, step 420 can separate from the generational loop.

At step 422, the optimization algorithm can terminate the method 400 by finalizing the cutting boundary (CB) relative to the model (M) based on the modified cutting surface (CS).

Figure 18:
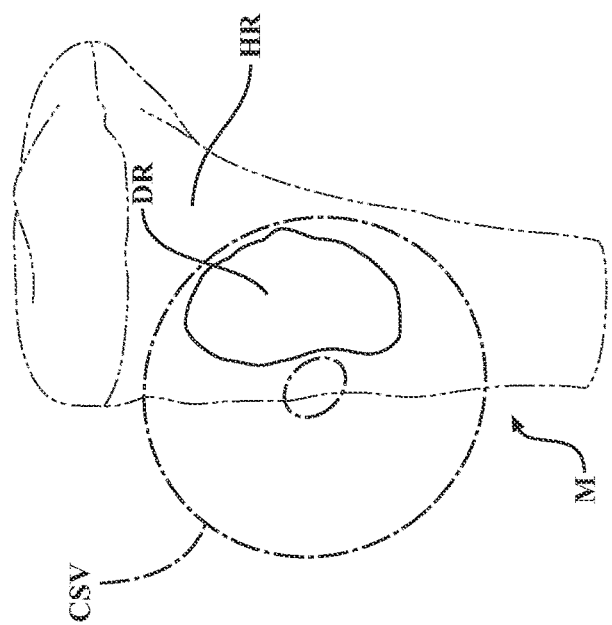
FIG. 18 illustrates one example of a closed 3D volume cutting surface arranged relative to the model of the diseased region for implementing the method of FIG. 15.
Figure 17:
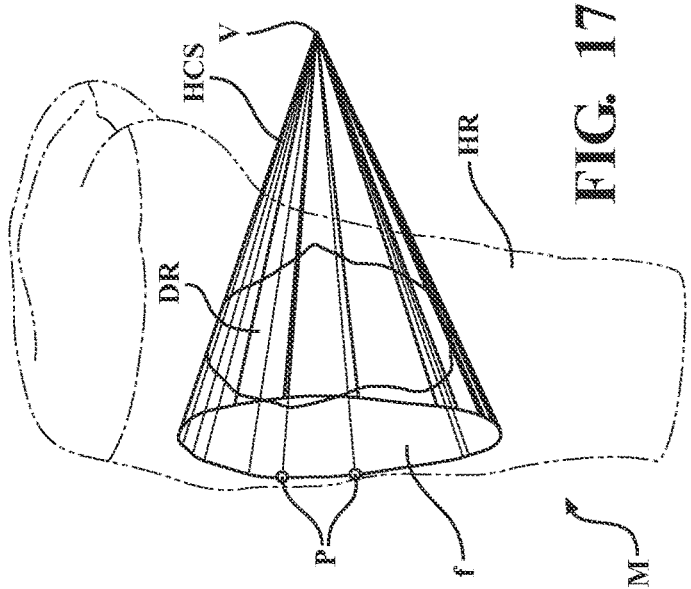
FIG. 17 illustrates one example of a 3D convex hull of cutting surfaces arranged relative to the model of the diseased region for implementing the method of FIG. 15.
Figure 16:
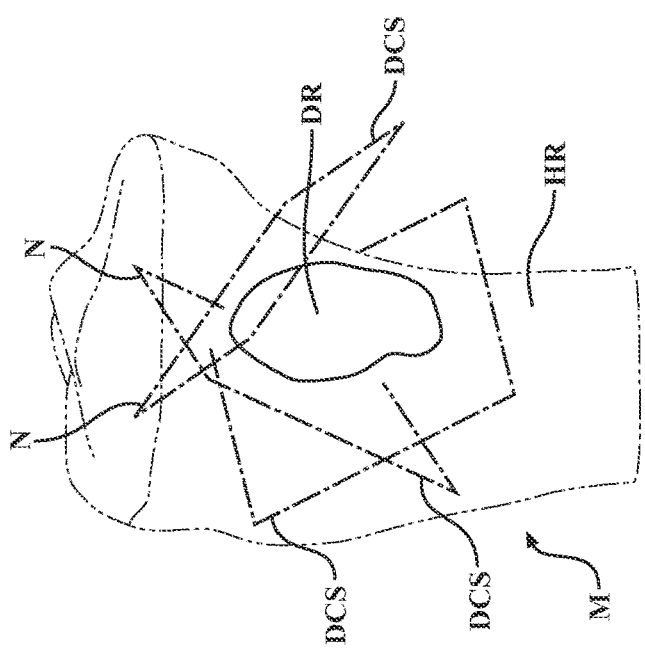
FIG. 16 illustrates one example of a plurality of discrete planar cut surfaces arranged relative to the model of the diseased region for implementing the method of FIG. 15.

With reference to FIGS. 16-18, the method 400 described can be implemented with various types and/or any number of cutting surfaces (CS). Any of the following cutting surface (CS) types can be utilized individually, or in combination.

In one example, as shown in FIG. 16, the method 400 can be implemented with a plurality of discrete cutting surfaces (DCS), such as, but not limited to discrete planar cutting surfaces (DCS). Alternatively, the discrete cutting surfaces (DCS) can a more complex configuration than a planar shape, such as triangular, quadrilateral, paraboloid, e.g., elliptical, cylindrical, circular, or spherical paraboloid or any type of hyperboloid. Modifying characteristics of the discrete cutting surfaces (DCS) can comprise modifying one or more of: a size of one or more of the discrete cutting surfaces (DCS) and a position and/or orientation of one or more of the discrete cutting surfaces (DCS).

In another example, as shown in FIG. 17, the method 400 can be implemented with a plurality of cutting surfaces arranged in a hull (HCS). In one implementation, the hull is a convex hull, in which a set of points (p) are defined as the smallest convex polygon enclosing all of the points (p) in the set. Applied to the diseased region (DR), the set of points (p) used to define the hull (HCS) can be identified based on the geometrical features (F) of the diseased region (DR), including most-distant points or outermost contours, as identified relative to any axis. The convex hull (HCS) in FIG. 17 is a polyhedron comprising several faces (f) containing the points (p), which in combination, bound the entire diseased region (DR) within the convex hull (HCS). The convex hull can be static or dynamic and can be implemented using any computational technique, such as Chan's algorithm, Quickhull, Gift wrapping, Graham scan, Monotone chain, divide-and-conquer, Kirkpatrick-Seidel algorithm, or the like. Modifying characteristics of the cutting surfaces hull (HCS) can comprise modifying one or more of: a size of the cutting surfaces; a position and/or orientation of the cutting surfaces; and a position and/or orientation of a vertex (v) or focal point of the hull, and/or the point set from which the hull is defined.

In another example, as shown in FIG. 18, the method 400 can be implemented with one or more cutting surfaces defining a volume (CSV). The cutting surface volume (CSV) can be an open volume or a close volume. The volume in FIG. 18 is a torus, but any volume is contemplated, such as a cylinder, cone, cube or cuboid, pyramid, prism, tetrahedron, sphere, and the like. Part or whole of the cutting surface volume (CSV) can be utilized to capture the diseased region (DR). Part or whole of the cutting surface volume (CSV) can exist outside of the boundaries of the model (M). Using the algorithm 400, modifying characteristics of the cutting surface volume (CSV) may include modifying one or more of: a size of the volume and a position and/or orientation of the volume.

1. Particle Swarm Optimization

Described in this section, and with reference to FIGS. 18 and 19, is one non-limiting implementation of the evolutionary optimization algorithm method 400. This approach can generate and compare several resection plans by rotating 3D data of the model (M) in space, then positioning the one or more cutting surfaces (CS) against the diseased region (DR), perpendicular to the rotation vector. The bone bounded by cutting surfaces (CS) is collaterally resected with the diseased region (DR). Particle Swarm Optimization is used to calculate the optimal position and orientation of the one or more cutting surfaces (CS) which removes the least amount of healthy region (HR). For a given resection plan, each cutting surface (CS) corresponds to a rotation in space, with the rotation for each cutting surface (CS) optimized to minimize the loss of amount of healthy region (HR). All aspects of the evolutionary optimization algorithm method 400 are incorporated with reference to this section.

a. Positioning of Cutting Surfaces

For this implementation, the cutting surfaces (CS) can be positioned relative to the model (M) according to any of the techniques described above. For example, the cutting surfaces (CS) can intersect or be spaced from the diseased region (DR), according to any planned or arbitrary location, or the like.

In one example, each bone surface mesh can be sliced to create a homogenous cubic voxel model (e.g., 2×2×2 mm cubic grid spacing, coordinates set at cube centers), with which resection plan volumes and the percentage of remaining bone could be compared from case to case. Bone voxels inside the diseased region (DR) surface mesh can be discarded, leaving two 3D arrays of surface points for the healthy region (HR) and diseased region (DR), and one 3D array of healthy region (HR) voxels. The coordinate system of the arrays can be defined by the principle axes of the segmented bone model (M). In one non-limiting example, both 3D surface arrays and the 3D voxel array can be uniformly repositioned in Cartesian coordinate space, such that the centroid of the diseased region (DR) array is set at the origin ($x_0$, $y_0$, $z_0$).

Figure 19B:
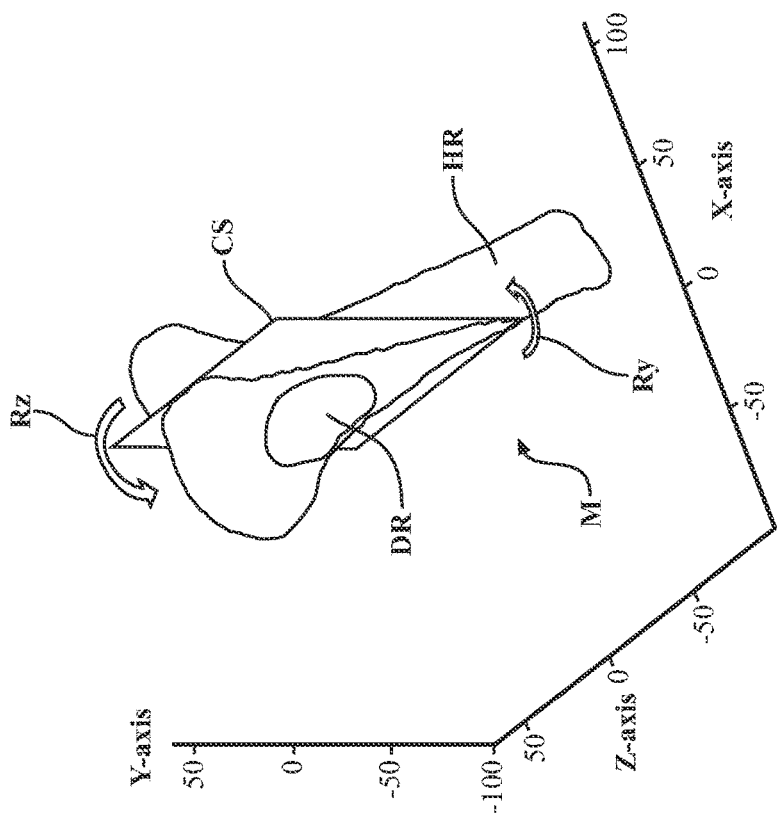
FIGS. 19A and 19B illustrate one example of a cutting surface placed relative to the diseased region wherein the cutting surface fitness is evaluated using one example of the evolutionary algorithm of FIG. 15, implemented by a particle swarm algorithm which rotates the cutting surface about y and z axes to assess volume of healthy region removed.
Figure 19A:
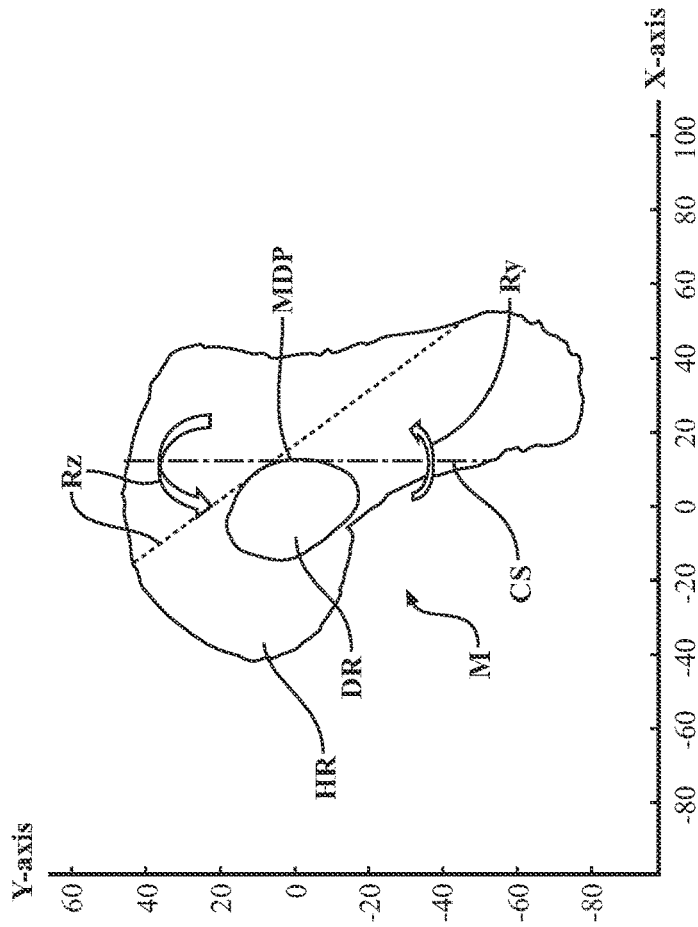

With reference to FIGS. 19A and 19B, for a given cutting surface (CS), the three arrays can be uniformly rotated by two angles (Ry) and (Rz), respectively, about the y and z axes, setting all three bone and diseased region (DR) arrays in a new orientation. In this new orientation the most distant point (MDP) of the diseased region (DR) surface mesh in the x-axis can be set as the cutting surface (CS). All bone voxels with an x-coordinate value less than the x coordinate of the most distant point (MDP) of the diseased region (DR) surface mesh can be marked as 'true' (a third rotation about the x-axis is unnecessary, as it would only spin the points about the x-axis). After recording the 'true' voxels for the healthy region (HR), the three arrays are reset to their initial orientation. Additional cutting surfaces (CS) add new pairs of rotation angles (Ry, Rz) about the y and z axes, respectively. After applying pairs of y and z rotations (Ry, Rz), each new cutting surface (CS) is set by the most distant point (MDP) of the diseased region (DR) surface mesh in the x axis. The total bone removed is the combination of voxels marked 'true' by all cutting surfaces (CS). This can be described mathematically as follows:

$$\cap_{i=1}^{n} n_i \cdot b_{xyz} < \max(n_i \cdot t_{xyz}) \qquad [13]$$

Equation [13] calculates the intersection of points of resected healthy region (HR), where n is the number of desired cutting surfaces (CS), $n_i$ is the normal of plane i, $b_{xyz}$ is the healthy region (HR) voxel points, and $t_{xyz}$ is the diseased region (DR) surface points.

b. Optimizing Cutting Surface via Particle Swarm

Particle Swarm Optimization (PSO) is a population-based stochastic optimization technique, capable of comparing many solutions for a single problem across a broad search space. A population of multivariable particles are encoded with values to generate candidate solutions, which are iteratively updated to produce new solutions. The values of the particle which generates the best solution is recorded, while the values of the particles of the rest of the population converge on the best solution. This process repeats until no improvement occurs, or some other termination condition is triggered.

In this technique, PSO is utilized to determine the position and/or orientation of a desired number of cutting surfaces (CS). The optimization parameter is the amount of healthy region (HR) collaterally resected by the cutting surfaces (CS). By optimizing the position and/or orientation of the cutting surfaces (CS), the PSO algorithm attempts to minimize bone loss. For any number of cutting surfaces (CS), their optimal position and/or orientation is that which minimizes loss of healthy region (HR). Using PSO, the y and z rotations (Ry, Rz) for each cutting surface (CS) are encoded in N multivariable particles, with values bounded between ±N degrees. In one example, 25 multivariable particles are utilized with values bounded between ±180°. However, other amounts of particles and bounding ranges are contemplated. The particles of the PSO function converge on the cutting surface (CS) rotation values (Ry, Rz) which generate solutions with fewer 'true' bone voxels. To illustrate, and with reference to FIGS. 19A and 19B, the model (M) of the bone is shown with the diseased and healthy regions (DR, HR). Each particle generates one potential resection. In the example of FIGS. 19A and 19B, the particle generates one cutting surface (CS) relative to the diseased region (DR), which is optionally set to the most distant point(s) (MDP) of the diseased region (DR) in the x-axis. The cutting surface (CS) corresponds to two random values between ±180° and the pair of values are rotated (Ry, Rz) about y and z axes, respectively. The amount of healthy region (HR) is computed and compared for each rotation (Ry, Rz). The candidate solution yielding the least amount of healthy region (HR) removed is set as the best solution.

c. Geometric Validation of Proposed Resection Plans

For solutions with fewer than three cutting surfaces (CS) there are no restrictions on the shape of the resection plan, as it is impossible to create a closed 3D shape with only three planar faces. As such, any resection plan generated by the algorithm with three cutting surfaces (CS) or fewer can be removed as the remaining (non-cutting surface) faces of the resection plan geometry will be comprised of the healthy bone (HR) and/or diseased region (DR) surface.

For solutions using four or more cutting surfaces (CS), it is possible that the cutting surfaces (CS) may be aligned in such a way that a generated resection plan cannot be removed from the bone. To confirm solutions can be removed after cutting along the cutting surfaces (CS), the resection plan can be further assessed for an 'exit path', which in one example, can be a 2D projection of the resection plan, perpendicular to the line of intersection between two cutting surfaces (CS), where no cutting surfaces (CS) are pointing toward the 'exit path'. The directionality of each cutting surface (CS) can be determined by the z value of the cutting surface (CS) normal, where a negative value indicates the cutting surface (CS) points away from the viewing angle and allows the resection, and a positive value indicates the cutting surface (CS) points toward the viewing angle, and occludes the resection.

This assessment of viability is performed on each candidate solution, in every iteration of the optimization. A viewing angle is set as the line of intersection between a pair of cutting surfaces (CS), then, with respect to the selected viewing angle, the relative alignment of each cutting surface (CS) is determined. For a single candidate solution, if any of the remaining cutting surfaces (CS) are found to occlude the resection, from that particular viewing angle, the algorithm moves to the next pair of cutting surfaces (CS), and performs the same checks with respect to the new viewing angle. If a particular viewing angle results in each remaining cutting surface (CS) having a negative relative z normal value, then no cutting surface (CS) occludes the resection, and the candidate solution is viable.

Figure 20A:
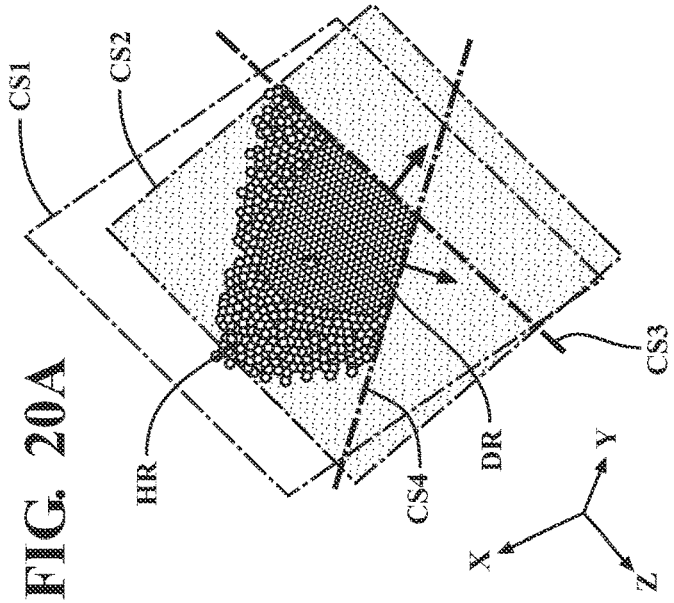
FIGS. 20A-20C illustrate a technique for evaluating viability of three 2D projections of a resection plan generated using the particle swarm algorithm, according to one example.
Figure 20B:
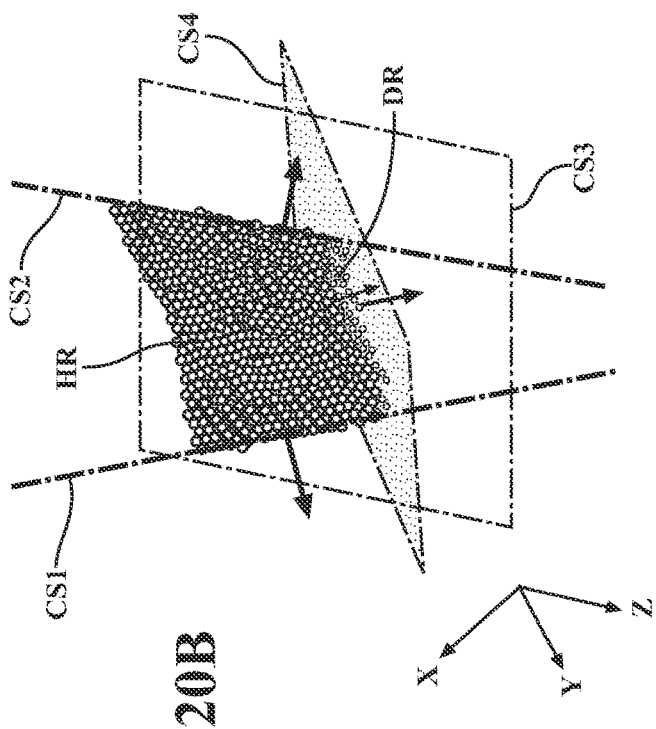
Figure 20C:
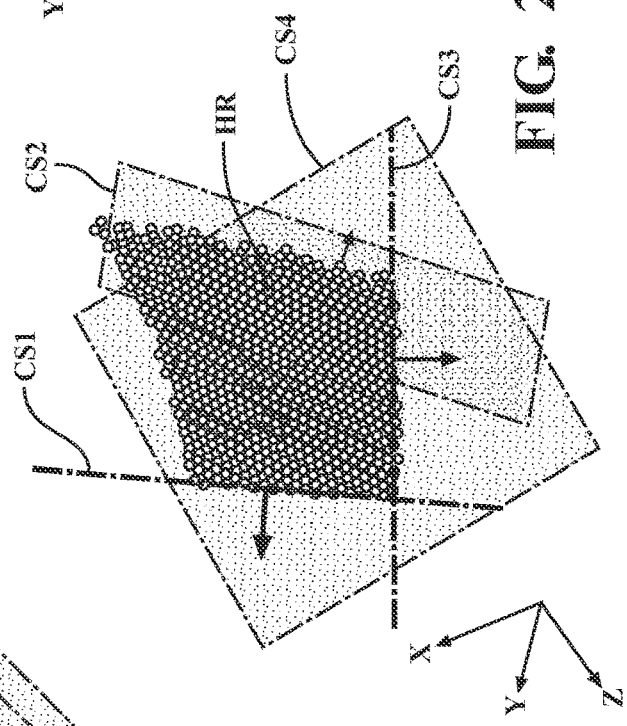

If no cutting surface (CS) pair projection allows removal, then that single particle's candidate solution from the current iteration of the PSO algorithm is penalized and the next solution is assessed. One example of a process of checking whether the resection plan geometry is viable is shown in FIGS. 20A-20C, illustrating an example with three 2D projections of a resection plan with four cutting surfaces (CS1-CS4). Here, the bone model (M) surface and volume points are projected in two dimensions and include the diseased region (DR) and the planned portion of healthy region (HR) to be removed. Each view is aligned with the line of intersection between a pair of cutting surfaces (CS). Cutting surfaces (CS) are shown with the corresponding normal vector. FIGS. 20A and 20B show that the resection plan cannot be removed along the corresponding projection. Specifically, as shown in FIG. 20A, cutting surface (CS2) is occluding (shown in the FIGS. 20A-20C by shading) the resection with normal vector pointing towards the viewing angle. Also, as shown in FIG. 20B, the cutting surface (CS4) is slightly occluding the resection. FIG. 20C shows a projection in which the resection can be removed, as no cutting surface (CS) normal vector points 'toward' the viewing angle.

Another method for geometry validation of the plan can be implemented by comparing the quantity of surface points to volume points for each view. Surface and volume points can be approximated, e.g., rounded towards the nearest whole number. The evaluation described can be implemented computationally without need for visually depicting the same to the user. However, graphical representation is contemplated to enable user input or feedback to the evaluation. The above describes some implementations of assessing viability of the plan, however, other methods are contemplated.

II. Overview of System for Use with Automated Cut Planning Techniques

The techniques for automated cut planning, as described above, may be fully utilized, executed, surgically performed or otherwise involved with any aspects, features, or capabilities of the surgical system 100 and methods described in the following section.

Figure 21:
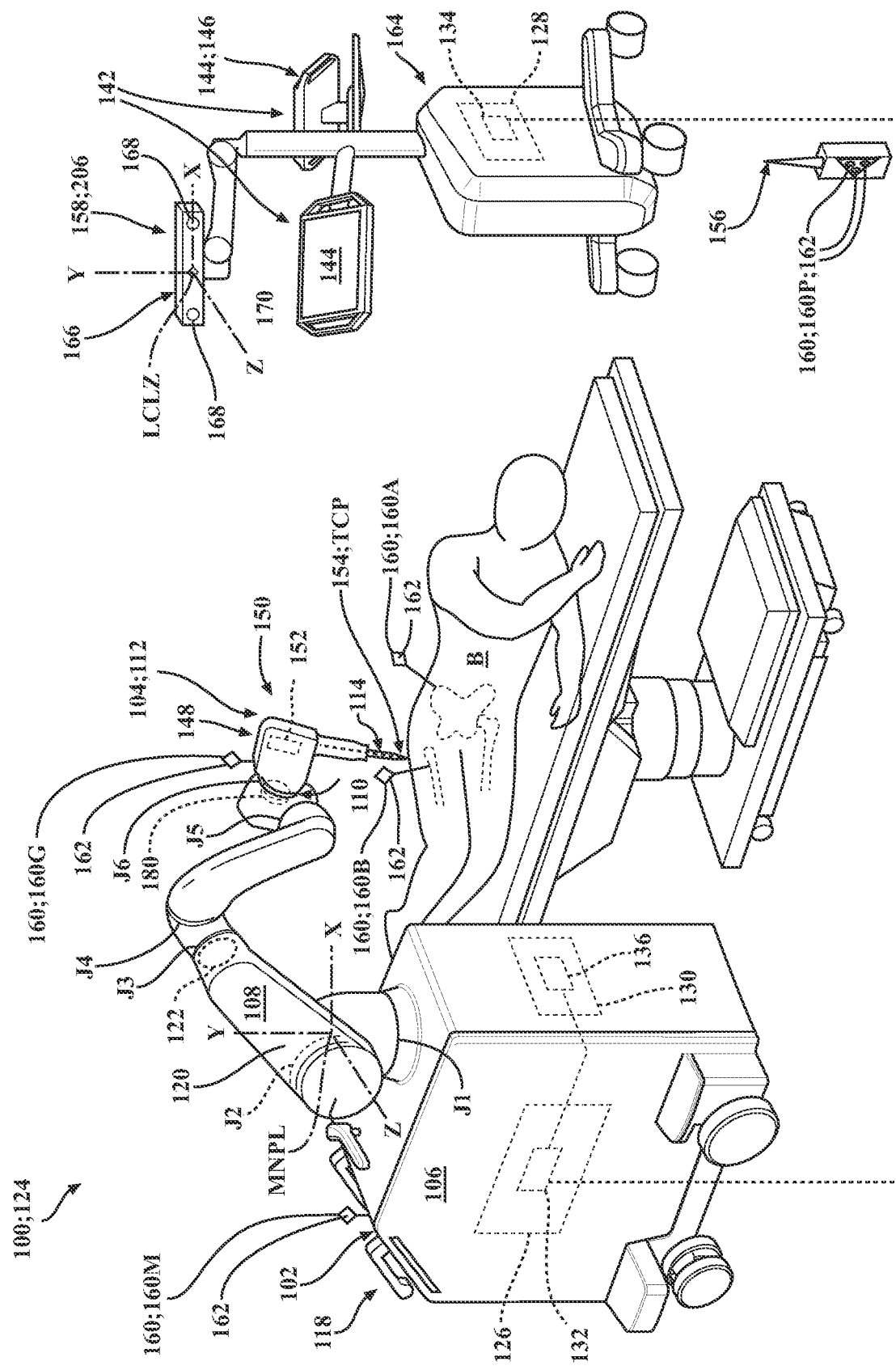
FIG. 21 is a perspective view of an example surgical system configured for executing a surgical plan generated by the techniques for automated cut planning as described herein.

Referring now to FIG. 21, a surgical system 100 comprising a robotic manipulator 102 supporting a tool 104 is shown. The surgical system 100 is useful for treating an anatomical volume or target site TS of a patient's P body B, such as bone or soft tissue. To this end, the manipulator 102 generally comprises a base 106, a robotic arm 108, and a coupling 110. The robotic arm 108 is supported by the base 106 and is configured to move, maintain, or otherwise control the position and/or orientation of the coupling 110 relative to the base 106 during use. The coupling 110 is adapted to releasably secure one or more types of tools 104 which, in turn, generally support or otherwise include an instrument 112 utilized in connection with various types of surgical procedures. In some embodiments, the instrument 112 may be configured to support, drive, rotate, oscillate, vibrate, and/or otherwise direct energy to an energy applicator 114 (e.g., drill bits, taps, burs, router, end mill, blades, saws, reamers, lasers, and the like) used to effect treatment at or adjacent to the target site TS. The end effector can also be a surgical cutting guide, such one comprising slots for guiding a hand-held saw on a cutting plane. In some embodiments, the instrument 112 may be configured to support, position, align, and/or guide implantable components 116 (e.g., cups, stems, screws, pins, rods, wires, anchors, prostheses, and the like) at or with respect to the target site TS, such as along a trajectory T maintained by the manipulator 102.

In FIG. 21, the patient P is undergoing an illustrative surgical procedure where the target site TS includes or is otherwise defined by portions of the patient's hip and femur. However, it will be appreciated that various types of surgical procedures are contemplated by the present disclosure, including without limitation surgical procedures involving bone tumor resection, partial or total knee or hip replacement surgery, shoulder replacement surgery, spine surgery, ankle surgery, and the like. The surgical procedure may involve tissue removal or other forms of treatment (e.g., cutting, drilling, reaming, coagulating, lesioning, other in-situ tissue treatments, and the like). In some embodiments, the surgical system 100 may be designed to facilitate cutting away material to be replaced by implantable components 116 (also referred to as "implants"), such as hip and knee implants, including unicompartmental, bicompartmental, multicompartmental, or total knee implants. Some types of implantable components 116 are shown in U.S. Pat. No. 9,381,085, entitled "Prosthetic Implant and Method of Implantation," the disclosure of which is hereby incorporated by reference in its entirety. However, and as will be appreciated from the subsequent description below, other configurations are contemplated, and the surgical system 100 could be utilized in connection with a number of different surgical procedures and may employ various types, styles, and configurations of manipulators 102, tools 104, instruments 112, energy applicators 114, and/or implantable components 116 without departing from the scope of the present disclosure. Furthermore, the surgical system 100 and techniques disclosed herein may be used to perform other procedures, surgical or non-surgical, or may be used in industrial applications or other applications where robotic systems are utilized.

The manipulator 102 (also referred to as a "surgical robot") moves the tool 104 relative to the target site TS and relative to the base 106 via the robotic arm 108 to, among other things, assist medical professionals in carrying out various types of surgical procedures with precise control over movement and positioning of the tool 104, the instrument 112, the energy applicator 114, and/or the implantable component 116. As noted above, the manipulator 102 generally comprises the base 106, the robotic arm 108, and the coupling 110. The base 106 is fixed to a manipulator cart 118 and supports the robotic arm 108 which, in turn, is configured to move, maintain, or otherwise control the position and/or orientation of the coupling 110 relative to the base 106 during use. To this end, the robotic arm 108 illustrated in FIG. 21 comprises a plurality of links 120 and joints J arranged in a serial arm configuration. However, it will be appreciated that the manipulator 102 could employ a different configuration without departing from the scope of the present disclosure. By way of non-limiting example, the manipulator 102 may have a parallel arm configuration, or any other suitable configuration. In some embodiments, more than one manipulator 102 may be utilized in a multiple arm configuration. One exemplary arrangement of the robotic arm 108 is described in U.S. Pat. No. 9,119,655, entitled "Surgical Manipulator Capable of Controlling a Surgical Instrument in Multiple Modes," the disclosure of which is hereby incorporated by reference in its entirety. It will be appreciated that the robotic arm 108 and other portions of the manipulator 102 may be arranged in a number of different configurations without departing from the scope of the present disclosure.

In the example shown in FIG. 21, the manipulator 102 comprises a plurality of joint encoders 122 located at the joints J for determining position data of the joints J. For simplicity, only one joint encoder 122 is labeled in FIG. 21, although other joint encoders 122 may be similarly illustrated. In the representative embodiment illustrated herein, the robotic arm 108 has six joints J1, J2, J3, J4, J5, J6 implementing at least six degrees of freedom (DOF) for the manipulator 102. However, the manipulator 102 may have any suitable number of degrees of freedom, may have any suitable number of joints J, and may have redundant joints J. The manipulator 102 need not require joint encoders 122 but may alternatively, or additionally, utilize motor encoders present on motors at each joint J. Furthermore, the manipulator 102 need not require rotary joints, but may alternatively, or additionally, utilize one or more prismatic joints. Any suitable combination of joint types are contemplated.

The surgical system 100 is able to monitor, track, and/or determine changes in the relative position and/or orientation of one or more parts of the manipulator 102, the robotic arm 108, the tool 104, the instrument 112, the energy applicator 114, and/or the implantable component 116, as well as various parts of the patient's body B, within a common coordinate system by utilizing various types of trackers (e.g., multiple degree-of-freedom optical, inertial, and/or ultrasonic sensing devices), navigation systems (e.g., machine vision systems, charge coupled device cameras, tracker sensors, surface scanners, and/or range finders), anatomical computer models (e.g., magnetic resonance imaging scans of the patient's P anatomy), data from previous surgical procedures and/or previously-performed surgical techniques (e.g., data recorded during prior steps of the surgical procedure), and the like. To these ends, and as is depicted schematically in FIG. 22, the surgical system 100 employs a control system 124 (also referred to as a "controller" 124) which may comprise or otherwise communicate with one or more of a robotic control system 126, a navigation system 128, and a tool control system 130 which cooperate to facilitate positioning, moving, and/or driving the tool 104 relative to the target site TS and other parts of the surgical system 100 via the manipulator 102, as described in greater detail below. Exemplary control methodologies are described in U.S. Pat. No. 10,327,849, entitled "Robotic System and Method for Backdriving the Same," the disclosure of which is hereby incorporated by reference in its entirety.

The base 106, or another portion of the manipulator 102, generally provides a fixed reference coordinate system for other components of the manipulator 102 and/or other components of the surgical system 100. Generally, the origin of a manipulator coordinate system MNPL is defined at the fixed reference of the base 106. The base 106 may be defined with respect to any suitable portion of the manipulator 102, such as one or more of the links 120. Alternatively or additionally, the base 106 may be defined with respect to the manipulator cart 118, such as where the manipulator 102 is physically attached to the cart 118. In some embodiments, the base 106 is defined at an intersection of the axis of joint J1 and the axis of joint J2. Thus, although joint J1 and joint J2 are moving components in reality, the intersection of the axes of joint J1 and joint J2 is nevertheless a virtual fixed reference pose, which provides both a fixed position and orientation reference and which does not move relative to the manipulator 102 and/or the manipulator cart 118. In some embodiments, the manipulator 102 could be hand-held such that the base 106 would be defined by a base portion of a tool (e.g., a portion held free-hand by the user) with a tool tip (e.g., an end effector) movable relative to the base portion. In this embodiment, the base portion has a reference coordinate system that is tracked, and the tool tip has a tool tip coordinate system that is computed relative to the reference coordinate system (e.g., via motor and/or joint encoders and forward kinematic calculations). Movement of the tool tip can be controlled to follow a path since its pose relative to the path can be determined. One example of this type of hand-held manipulator 102 is shown in U.S. Pat. No. 9,707,043, entitled "Surgical Instrument Including Housing, A Cutting Accessory that Extends from the Housing and Actuators that Establish the Position of the Cutting Accessory Relative to the Housing," the disclosure of which is hereby incorporated by reference in its entirety. It will be appreciated that the forgoing is a non-limiting, illustrative example, and other configurations are contemplated by the present disclosure.

Figure 22:
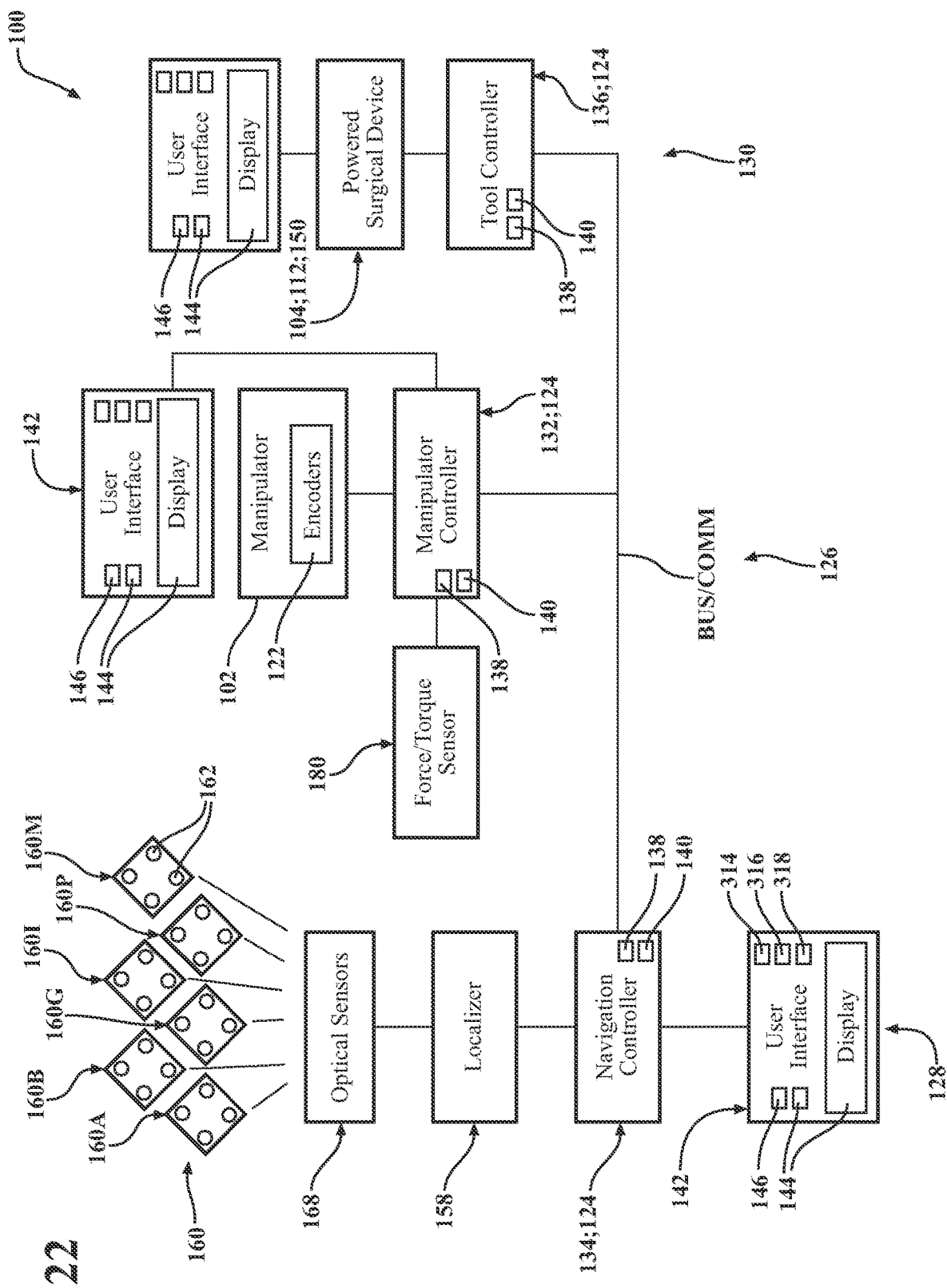
FIG. 22 is an example block diagram of a control system for controlling the surgical system of FIG. 21.

As is depicted schematically in FIG. 22, the robotic control system 126 comprises a manipulator controller 132, the navigation system 128 comprises a navigation controller 134, and the tool control system 130 comprises a tool controller 136. In the illustrated embodiment, the manipulator controller 132, the navigation controller 134, and the tool controller 136 are generally disposed in communication with each other (e.g., directly or indirectly), and/or with other components of the surgical system 100, such as via physical electrical connections (e.g., a tethered wire harness) and/or via one or more types of wireless communication (e.g., with a WiFi™ network, Bluetooth®, a radio network, and the like). The manipulator controller 132, the navigation controller 134, and/or the tool controller 136 may be realized as or with various arrangements of computers, processors, control units, and the like, and may comprise discrete components or may be integrated (e.g., sharing hardware, software, inputs, outputs, and the like). Other configurations are contemplated.

The manipulator controller 132, the navigation controller 134, and/or the tool controller 136 may each be realized as a computer with a processor 138 (e.g., a central processing unit) and/or other processors, memory 140, and/or storage (not shown), and are generally loaded with software as described in greater detail below. The processors 138 could include one or more processors to control operation of the manipulator 102, the navigation system 128, or the tool 104. The processors 138 could be any type of microprocessor, multi-processor, and/or multi-core processing system. The manipulator controller 132, the navigation controller 134, and/or the tool controller 136 may additionally or alternatively comprise one or more microcontrollers, field programmable gate arrays, systems on a chip, discrete circuitry, and/or other suitable hardware, software, and/or firmware capable of carrying out the functions described herein. The term "processor" is not intended to limit any embodiment to a single processor. The robotic control system 126, the navigation system 128, and/or the tool control system 130 may also comprise, define, or otherwise employ a user interface 142 with one or more output devices 144 (e.g., screens, displays, status indicators, and the like) and/or input devices 146 (e.g., push button, keyboard, mouse, microphone, voice-activation devices, gesture control devices, touchscreens, foot pedals, pendants, and the like). Other configurations are contemplated.

As noted above, one or more tools 104 (sometimes referred to as "end effectors") releasably attach to the coupling 110 of the manipulator 102 and are movable relative to the base 106 to interact with the anatomy of the patient P (e.g., the target site TS) in certain modes. The tool 104 may be grasped by the user (e.g., a surgeon). The tool 104 generally includes a mount 148 that is adapted to releasably attach to the coupling 110 of the manipulator 102. The mount 148 may support or otherwise be defined by the instrument 112 which, in some embodiments, may be configured as a powered surgical device 150 which employs a power generation assembly 152 (e.g., a motor, an actuator, geartrains, and the like) used to drive the energy applicator 114 attached thereto (e.g., via a chuck, a coupling, and the like). One exemplary arrangement of this type of manipulator 102, tool 104, and instrument 112 is described in U.S. Pat. No. 9,119,655, entitled "Surgical Manipulator Capable of Controlling a Surgical Instrument in Multiple Modes," previously referenced. The manipulator 102, the tool 104, and/or the instrument 112 may be arranged in alternative configurations. In some embodiments, the tool 104 and/or the instrument 112 may be like that shown in U.S. Pat. No. 9,566,121, entitled "End Effector of a Surgical Robotic Manipulator," the disclosure of which is hereby incorporated by reference in its entirety. In some embodiments, the tool 104 and/or the instrument 112 may be like that shown in U.S. Patent Application Publication No. US 2019/0231447 A1, entitled "End Effectors And Methods For Driving Tools Guided By Surgical Robotic Systems," the disclosure of which is hereby incorporated by reference in its entirety. Other configurations are contemplated. In some embodiments, and as is described in greater detail below, the instrument 112 may not be configured as a powered surgical device 150.

In some embodiments, the energy applicator 114 is designed to contact and remove the tissue of the patient P at the target site TS. To this end, the energy applicator 114 may comprise a bur 154 in some embodiments. The bur 154 may be substantially spherical and comprise a spherical center, a radius, and a diameter. Alternatively, the energy applicator 114 may be a drill bit, a saw blade, undercutting saw, an ultrasonic vibrating tip, and the like. The tool 104, the instrument 112, and/or the energy applicator 114 may comprise any geometric feature, including without limitation a perimeter, a circumference, a radius, a diameter, a width, a length, a volume an area, a surface/plane, a range of motion envelope (along any one or more axes), and the like. The geometric feature may be considered to determine how to locate the tool 104 relative to the tissue at the target site TS to perform the desired treatment. In some of the embodiments described herein, a spherical bur 154 having or otherwise defining tool center point (TCP) will be described for convenience and ease of illustration, but is not intended to limit the tool 104, the instrument 112, and/or the energy applicator 114 to any particular form. In some of the embodiments described herein, the tool center point TCP is defined by a portion of the instrument 112 or the tool 104 rather than the energy applicator 114. Other configurations are contemplated.

In some embodiments, such as where the instrument 112 is realized as a powered surgical device 150, the tool 104 may employ the tool controller 136 to facilitate operation of the tool 104, such as to control power to the power generation assembly 152 (e.g., a rotary motor), control movement of the tool 104, control irrigation/aspiration of the tool 104, and the like. The tool controller 136 may be in communication with the manipulator controller 132 and/or other components of the surgical system 100. In some embodiments, the manipulator controller 132 and/or the tool controller 136 may be housed in the manipulator 102 and/or the manipulator cart 118. In some embodiments, parts of the tool controller 136 may be housed in the tool 104. Other configurations are contemplated. The tool control system 130 may also comprise the user interface 142, with one or more output devices 144 and/or input devices 146, which may formed as a part of the tool 104 and/or may be realized by other parts of the surgical system 100 and/or the control system 124 (e.g., the robotic control system 126 and/or the navigation system 128). Other configurations are contemplated.

The manipulator controller 132 controls a state (position and/or orientation) of the tool 104 (e.g., the tool center point TCP) with respect to a coordinate system, such as the manipulator coordinate system MNPL. The manipulator controller 132 can control (linear or angular) velocity, acceleration, or other derivatives of motion of the tool 104. The tool center point TCP, in one example, is a predetermined reference point defined at the energy applicator 114. However, as noted above, other components of the tool 104 and/or instrument 112 could define the tool center point TCP in some embodiments. In any event, the tool center point TCP has a known pose relative to other coordinate systems. The pose of the tool center point TCP may be static or may be calculated. In some embodiments, the geometry of the energy applicator 114 is known in or defined relative to a tool center point TCP coordinate system. The tool center point TCP may be located at the spherical center of the bur 154 of the energy applicator 114 supported or defined by the instrument 112 of the tool 104 such that only one point is tracked. The tool center point TCP may be defined in various ways depending on the configuration of the energy applicator 114, the instrument 112, the tool 104, and the like.

The manipulator 102 could employ the joint encoders 122 (and/or motor encoders, as noted above), or any other non-encoder position sensing method, to enable a pose of the tool center point TCP to be determined. The manipulator 102 may use joint J measurements to determine the tool center point TCP pose, and/or could employ various techniques to measure the tool center point TCP pose directly. It will be appreciated that the control of the tool 104 is not limited to a center point. For example, any suitable primitives, meshes, and the like can be used to represent the tool 104. Other configurations are contemplated.

With continued reference to FIG. 21, as noted above, the surgical system 100 also includes the navigation system 128 which, among other things, is configured to track, monitor, detect, or otherwise sense movement of various objects, such as the tool 104, a pointer 156 used for registering objects (e.g., portions of the anatomy, trackers, and the like), and parts of the patient's body B (e.g., bones or other anatomy at or adjacent to the target site TS). To this end, the navigation system 128 employs a localizer 158 configured to sense the position and/or orientation of trackers 160 within a localizer coordinate system LCLZ. The navigation controller 134 is disposed in communication with the localizer 158 and gathers position and/or orientation data for each tracker 160 sensed within a field of view of the localizer 158 in the localizer coordinate system LCLZ.

It will be appreciated that the localizer 158 can sense the position and/or orientation of a plurality of trackers 160 to track a corresponding plurality of objects within the localizer coordinate system LCLZ. By way of example, and as is depicted in FIG. 21, trackers 160 may comprise a pointer tracker 160P coupled to the pointer 156, a manipulator tracker 160M coupled to the base 106 of the manipulator 102, one or more tool trackers 160G, 160I coupled to portions of the tool 104, a first patient tracker 160A coupled to one portion of the anatomy of the patient P, and a second patient tracker 160B coupled to another portion of the anatomy of the patient P, as well as additional patient trackers, trackers for additional medical and/or surgical tools, instruments, and the like.

In some embodiments, and as is shown in FIG. 21, the one or more tool trackers 160G, 160I may each be firmly affixed to different portions of the tool 104, such as those that may be configured to move relative to each other and/or to the manipulator tracker 160M, which is firmly affixed to the base 106 of the manipulator 102. By way of non-limiting example, and as is described in greater detail below, a first tool tracker 160G could be coupled to the mount 148 (or to another part of the tool 104) for concurrent movement with the coupling 110 via the manipulator 102, and a second tool tracker 160I could be coupled to a different portion of the tool 104 which moves relative to the mount 148 and/or the coupling 110 in one or more degrees of freedom. While the first tool tracker 160G and the second tool tracker 160I depicted in FIG. 21 can be used by the navigation system 128 to readily determine the relative positions and/or orientations of different parts of the tool 104 via the localizer 158, certain embodiments of the present disclosure may be configured to facilitate this determination in other ways (e.g., such as with one or more sensors). Here, other configurations are contemplated by the present disclosure, and it will be appreciated that various combinations of trackers 160, sensors, predetermined geometric relationships, and the like can be utilized in order to track certain objects or otherwise relate those objects to a tracked object.

With continued reference to FIG. 21, the first patient tracker 160A is firmly affixed to one bone of the patient's body B at or adjacent to the target site TS (e.g., to the pelvis near the acetabulum), and the second patient tracker 160B is firmly affixed to a different bone (e.g., to a portion of the femur). While not shown in detail, it will be appreciated that the patient trackers 160A, 160B can be coupled to a number of different bones in the patient's body B in various ways, such as by threaded engagement, clamping, or by other techniques. Similarly, the first tool tracker 160G and/or the second tool tracker 160I could be fixed to portions of the tool 104 in various ways, such as by integration during manufacture or by releasable attachment ahead of or during a surgical procedure. It will be appreciated that various trackers 160 may be firmly affixed to different types of tracked objects (e.g., discrete bones, tools, pointers, and the like) in a number of different ways. For example, trackers 160 may be rigidly fixed, flexibly connected (optical fiber), or not physically connected at all (ultrasound), as long as there is a suitable (e.g., supplemental) way to determine the relationship (e.g., measurement) of that respective tracker 160 to the object or anatomy that it is associated with.

The position and/or orientation of the trackers 160 relative to the objects or anatomy to which they are attached can be determined by utilizing known registration techniques. For example, determining the pose of the patient trackers 160A, 160B relative to the portions of the patient's body B to which they are attached can be accomplished with various forms of point-based registration, such as where a distal tip of the pointer 156 is used to engage against specific anatomical landmarks (e.g., touching specific portions of bone) or is used to engage several parts of a bone for surface-based registration as the localizer 158 monitors the position and orientation of the pointer tracker 160P. Conventional registration techniques can then be employed to correlate the pose of the patient trackers 160A, 160B to the patient's anatomy (e.g., to each of the femur and the acetabulum).

Other types of registration are also possible, such as by using patient trackers 160A, 160B with mechanical clamps that attach to bone and have tactile sensors (not shown) to determine a shape of the bone to which the clamp is attached. The shape of the bone can then be matched to a three-dimensional model of bone for registration. A known relationship between the tactile sensors and markers 162 on the patient tracker 160A, 160B may be entered into or otherwise known by the navigation controller 134 (e.g., stored in memory 140). Based on this known relationship, the positions of the markers 162 relative to the patient's anatomy can be determined. Position and/or orientation data may be gathered, determined, or otherwise handled by the navigation controller 134 using a number of different registration/navigation techniques to determine coordinates of each tracker 160 within the localizer coordinate system LCLZ or another suitable coordinate system. These coordinates are communicated to other parts of the control system 124, such as to the robotic control system 126 to facilitate articulation of the manipulator 102 and/or to otherwise assist the surgeon in performing the surgical procedure, as described in greater detail below.

In the representative embodiment illustrated herein, the manipulator controller 132 and the tool controller 136 are operatively attached to the base 106 of the manipulator 102, and the navigation controller 134 and the localizer 158 are supported on a mobile cart 164 which is movable relative to the base 106 of the manipulator 102. The mobile cart 164 may also support the user interface 142 to facilitate operation of the surgical system 100 by displaying information to, and/or by receiving information from, the surgeon or another user. While shown as a part of the navigation system 128 in the representative embodiment illustrated in FIG. 21, it will be appreciated that the user interface 142 could form part of, or otherwise communicate with, other parts of the control system 124 such as the robotic control system 126 and/or the tool control system 130. To this end, the user interface 142 may be disposed in communication with navigation controller 134, the manipulator controller 132, and/or the tool controller 136, and may likewise comprise one or more output devices 144 (e.g., monitors, indicators, display screens, and the like) to present information to the surgeon or other users (e.g., images, video, data, graphics, navigable menus, and the like), and one or more input devices 146 (e.g., physical or virtual input controls, buttons, touch screens, keyboards, mice, gesture or voice-based input devices, and the like). One type of mobile cart 164 and user interface 142 utilized in this type of navigation system 128 is described in U.S. Pat. No. 7,725,162, entitled "Surgery System," the disclosure of which is hereby incorporated by reference in its entirety.

Because the mobile cart 164 and the base 106 of the manipulator 102 can be positioned relative to each other and also relative to the patient's body B, one or more portions of the surgical system 100 are generally configured to transform the coordinates of each tracker 160 sensed via the localizer 158 from the localizer coordinate system LCLZ into the manipulator coordinate system MNPL (or to other coordinate systems), or vice versa, so that articulation of the manipulator 102 can be performed based at least partially on the relative positions and/or orientations of certain trackers 160 within a common coordinate system (e.g., the manipulator coordinate system MNPL, the localizer coordinate system LCLZ, or another common coordinate system). It will be appreciated that coordinates within the localizer coordinate system LCLZ can be transformed into coordinates within the manipulator coordinate system MNPL (or other coordinate systems), and vice versa, using a number of different transformation techniques. One example of the translation or transformation of data between coordinate systems is described in U.S. Pat. No. 8,675,939, entitled "Registration of Anatomical Data Sets", the disclosure of which is hereby incorporated by reference in its entirety.

In the illustrated embodiment, the localizer 158 is an optical localizer and includes a camera unit 166 with one or more optical sensors 168 and, in some embodiments, a video camera 170. The localizer 158 may also comprise a localizer controller (not shown) which communicates with the navigation controller 134 or otherwise forms part of the navigation system 128. The navigation system 128 employs the optical sensors 168 of the camera unit 166 to sense the position and/or orientation of the trackers 160 within the localizer coordinate system LCLZ. In the representative embodiment illustrated herein, the trackers 160 each employ a plurality of markers 162 (see FIG. 21) which can be sensed by the optical sensors 168 of the camera unit 166. One example of a navigation system 128 of this type is described in U.S. Pat. No. 9,008,757, entitled "Navigation System Including Optical and Non-Optical Sensors," the disclosure of which is hereby incorporated by reference in its entirety. In some embodiments, the markers 162 are active markers (e.g., light emitting diodes "LEDs") which emit light that can be sensed by the localizer 158. In some embodiments, the trackers 160 may employ passive markers (e.g., reflectors) which reflect light emitted from the localizer 158 or another light source. Although one embodiment of the navigation system 128 is illustrated throughout the drawings, the navigation system 128 could have any suitable configuration for monitoring trackers 160 which, as will be appreciated from the subsequent description below, may be of various types and configurations. For example, the navigation system 128 may comprise multiple localizers 158 and/or trackers 160 of the same or different type.

In some embodiments, the navigation system 128 and/or the localizer 158 are radio frequency (RF) based. For example, the navigation system 128 may comprise an RF transceiver coupled to the navigation controller 134 and/or to another computing device, controller, and the like. Here, the trackers 160 may comprise RF emitters or transponders, which may be passive or may be actively energized. The RF transceiver transmits an RF tracking signal, and the RF emitters respond with RF signals such that tracked states are communicated to (or interpreted by) the navigation controller 134. The RF signals may be of any suitable frequency. The RF transceiver may be positioned at any suitable location to track the objects using RF signals effectively. Furthermore, it will be appreciated that embodiments of RF-based navigation systems may have structural configurations that are different than the active marker-based navigation system 128 illustrated herein.

In some embodiments, the navigation system 128 and/or localizer 158 are electromagnetically (EM) based. For example, the navigation system 128 may comprise an EM transceiver coupled to the navigation controller 134 and/or to another computing device, controller, and the like. Here, the trackers 160 may comprise EM components attached thereto (e.g., various types of magnetic trackers, electromagnetic trackers, inductive trackers, and the like), which may be passive or may be actively energized. The EM transceiver generates an EM field, and the EM components respond with EM signals such that tracked states are communicated to (or interpreted by) the navigation controller 134. The navigation controller 134 may analyze the received EM signals to associate relative states thereto. Here too, it will be appreciated that embodiments of EM-based navigation systems may have structural configurations that are different than the active marker-based navigation system 128 illustrated herein.

In some embodiments, the navigation system 128 and/or the localizer 158 could be based on one or more types of imaging systems that do not necessarily require trackers 160 to be fixed to objects in order to determine location data associated therewith. For example, an ultrasound-based imaging system could be provided to facilitate acquiring ultrasound images (e.g., of specific known structural features of tracked objects, of markers or stickers secured to tracked objects, and the like) such that tracked states (e.g., position, orientation, and the like) are communicated to (or interpreted by) the navigation controller 134 based on the ultrasound images. The ultrasound images may be three-dimensional, two-dimensional, or a combination thereof. The navigation controller 134 may process ultrasound images in near real-time to determine the tracked states. The ultrasound imaging device may have any suitable configuration and may be different than the camera unit 166 as shown in FIG. 21. By way of further example, a fluoroscopy-based imaging system could be provided to facilitate acquiring X-ray images of radio-opaque markers (e.g., stickers, tags, and the like with known structural features that are attached to tracked objects) such that tracked states are communicated to (or interpreted by) the navigation controller 134 based on the X-ray images. The navigation controller 134 may process X-ray images in near real-time to determine the tracked states. Similarly, other types of optical-based imaging systems could be provided to facilitate acquiring digital images, video, and the like (e.g., via a charge-coupled device "CCD" sensor such as the video camera 170) of specific known objects (e.g., based on a comparison to a virtual representation of the tracked object or a structural component or feature thereof) and/or markers (e.g., stickers, tags, and the like that are attached to tracked objects) such that tracked states are communicated to (or interpreted by) the navigation controller 134 based on the digital images. The navigation controller 134 may process digital images in near real-time to determine the tracked states.

Accordingly, it will be appreciated that various types of imaging systems, including multiple imaging systems of the same or different type, may form a part of the navigation system 128 without departing from the scope of the present disclosure. Those having ordinary skill in the art will appreciate that the navigation system 128 and/or localizer 158 may have other suitable components or structure not specifically recited herein. For example, the navigation system 128 may utilize solely inertial tracking or any combination of tracking techniques, and may additionally or alternatively comprise fiber optic-based tracking, machine-vision tracking, and the like. Furthermore, any of the techniques, methods, and/or components associated with the navigation system 128 illustrated in FIG. 21 may be implemented in a number of different ways, and other configurations are contemplated by the present disclosure.

In some embodiments, the surgical system 100 is capable of displaying a virtual representation of the relative positions and orientations of tracked objects to the surgeon or other users of the surgical system 100, such as with images and/or graphical representations of the anatomy of the patient's body B, the tool 104, the instrument 112, the energy applicator 114, and the like presented on one or more output devices 144 (e.g., a display screen). The manipulator controller 132 and/or the navigation controller 134 may also utilize the user interface 142 to display instructions or request information such the surgeon or other users may interact with the robotic control system 126 (e.g., using a graphical user interface GUI) to facilitate articulation of the manipulator 102. Other configurations are contemplated.

As noted above, the localizer 158 tracks the trackers 160 to determine a state of each of the trackers 160 which corresponds, respectively, to the state of the object respectively attached thereto. The localizer 158 may perform known triangulation techniques to determine the states of the trackers 160 and associated objects. The localizer 158 provides the state of the trackers 160 to the navigation controller 134. In some embodiments, the navigation controller 134 determines and communicates the state of the trackers 160 to the manipulator controller 132. As used herein, the state of an object includes, but is not limited to, data that defines the position and/or orientation of the tracked object, or equivalents/derivatives of the position and/or orientation. For example, the state may be a pose of the object, and may include linear velocity data, and/or angular velocity data, and the like. Other configurations are contemplated.

Referring to FIG. 22, the surgical system 100 generally comprises the control system 124 which, among other components, may include or otherwise be defined as the manipulator controller 132, the navigation controller 134, the tool controller 136, and/or various components of the robotic control system 126, the navigation system 128, and/or the tool control system 130 as noted above. The control system 124 may also include one or more software modules shown in FIG. 22. The software modules may be part of one or more programs that operate on the manipulator controller 132, the navigation controller 134, the tool controller 136, or any combination thereof, to process data used to facilitate or otherwise assist with control of the surgical system 100. The software programs and/or modules include computer readable instructions stored in non-transitory memory 140 on the manipulator controller 132, the navigation controller 134, the tool controller 136, or a combination thereof, to be executed by one or more processors 138 of one or more of the controllers 136, 132, 134. The non-transitory memory 140 can store the instructions for implementing the above described automated planning techniques.

The memory 140 may be of any suitable configuration, such as random access memory (RAM), non-volatile memory, and the like, and may be implemented locally or from a remote location (e.g., a database, a server, and the like). Additionally, software modules for prompting and/or communicating with the user may form part of the modules or programs, and may include instructions stored in memory 140 on the manipulator controller 132, the navigation controller 134, the tool controller 136, or any combination thereof. The user may interact with any of the input devices 146 and/or output devices 144 of any of the user interfaces 142 (e.g., the user interface 142 of the navigation system 128 shown in FIG. 22) to communicate with the software modules and/or programs. The control system 124 may also comprise user interfaces 142 (e.g., a graphical user interface GUI) or other software or modules that could run on a separate device from the manipulator controller 132, the navigation controller 134, and/or the tool controller 136 (e.g., a portable electronic device such as a tablet computer). Other configurations are contemplated.

The control system 124 may comprise any suitable arrangement and/or configuration of input, output, and processing devices suitable for carrying out the functions and methods described herein. The surgical system 100 may comprise the manipulator controller 132, the navigation controller 134, or the tool controller 136, or any combination thereof, or may comprise only some of these controllers, or additional controllers, any of which could form part of the control system 124 as noted above. The controllers 132, 134, 136 may communicate via a wired bus or communication network as shown in FIG. 22, via wireless communication, or otherwise. The control system 124 may also be referred to as a controller, and may likewise comprise one or more microcontrollers, field programmable gate arrays, systems on a chip, discrete circuitry, sensors, displays, user interfaces, indicators, and/or other suitable hardware, software, or firmware that is capable of carrying out the functions described herein. Other configurations are contemplated.

Figure 23:
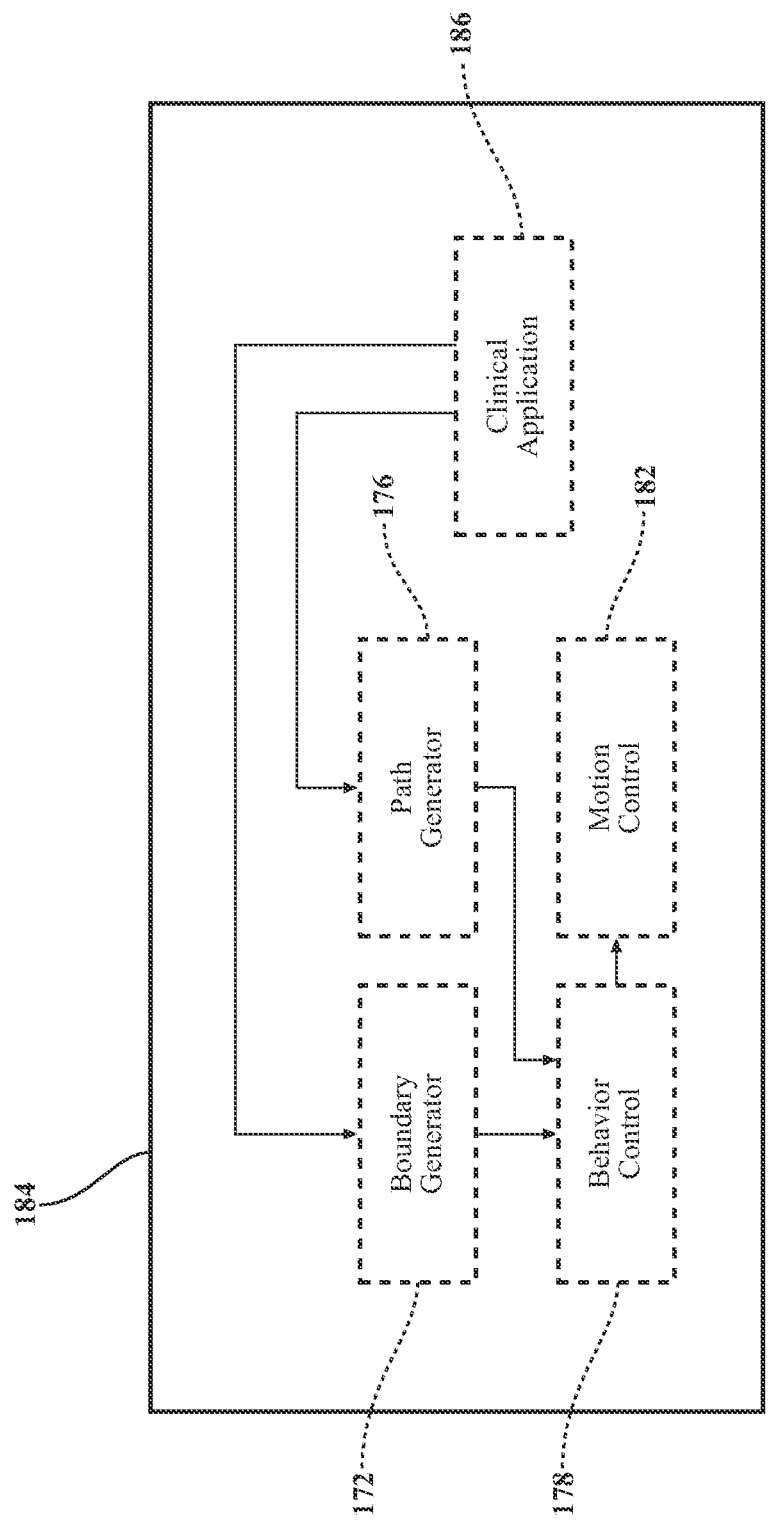
FIG. 23 is an example functional block diagram of a software program of the control system of FIG. 22.

Referring to FIG. 23, in some embodiments, the software employed by the control system 124 may include a boundary generator 172. As shown in FIG. 23, the boundary generator 172 is a software program or module that generates a virtual boundary 174 for constraining movement and/or operation of the tool 104. In one implementation, the virtual boundary 174 is the cutting boundary (CB) generated from the above-described planning techniques. The virtual boundary 174 may be one-dimensional, two-dimensional, or three-dimensional, and may comprise a point, line, axis, trajectory, plane, or other shapes, including complex geometric shapes.

Figure 24:
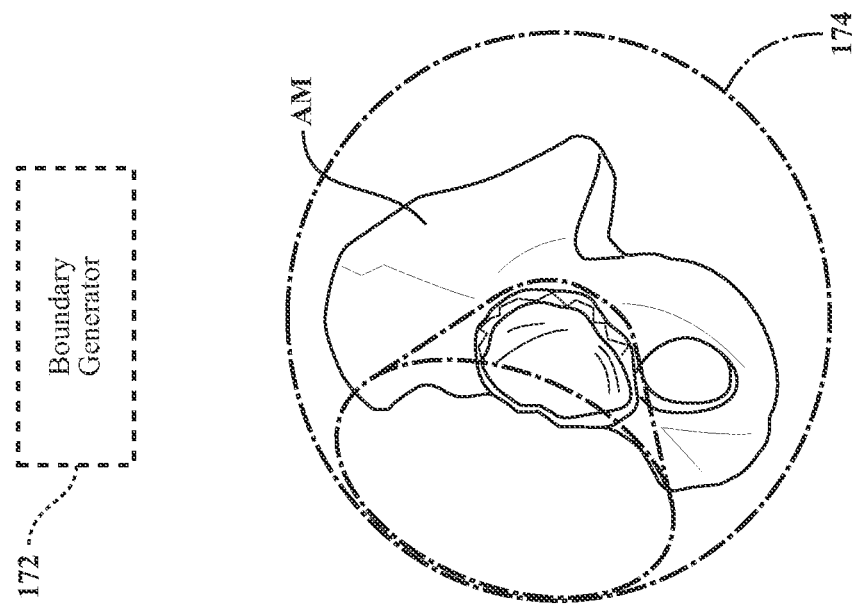
FIG. 24 is an illustrative view of an example target site depicting an output of a boundary generator of the software program of FIG. 23.

In some embodiments, the virtual boundary 174 is a surface defined by a triangle mesh. Such virtual boundaries 174 may also be referred to as virtual objects. The virtual boundaries 174 may be defined with respect to an anatomical model AM, such as a three-dimensional bone model. The anatomical model Am is associated with the real anatomy of the patient P by virtue of the anatomical model AM being mapped to the anatomy of the patient P via registration or other processes. In the example of FIG. 24, the virtual boundaries 174 comprises a generally spherical mesh substantially surrounding an acetabulum with an entry portion (e.g., an opening) that provides access to the acetabulum. The entry portion has a funnel or conical shape. In this representative embodiment, the virtual boundary 174 is associated with a three-dimensional model of the acetabulum of the pelvis.

The anatomical model AM and associated virtual boundaries 174 are registered to one or more patient trackers 160A, 160B. Thus, the anatomical model AM (and the associated real anatomy of the patient P) and the virtual boundaries 174 fixed to the anatomical model AM can be tracked by the patient trackers 160A, 160B. The virtual boundaries 174 may be implant-specific (e.g., defined based on a size, shape, volume, and the like of an implantable component 116) and/or patient-specific (e.g., defined based on the anatomy of the patient P). The virtual boundaries 174 may be boundaries that are created pre-operatively, intra-operatively, or combinations thereof. In other words, the virtual boundaries 174 may be defined before the surgical procedure begins, during the surgical procedure (including during tissue removal), or combinations thereof. In any event, the control system 124 obtains the virtual boundaries 174 by storing/retrieving the virtual boundaries 174 in/from memory 140, obtaining the virtual boundaries 174 from memory 140, creating the virtual boundaries 174 pre-operatively, creating the virtual boundaries 174 intra-operatively, and the like.

The manipulator controller 132 and/or the navigation controller 134 may track the state of the tool 104 relative to the virtual boundaries 174. In some embodiments, the state of the tool center point TCP is measured relative to the virtual boundaries 174 for purposes of determining haptic forces to be applied to a virtual rigid body VRB model via a virtual simulation VS so that the tool 104 remains in a desired positional relationship to the virtual boundaries 174. The results of the virtual simulation VS are commanded to the manipulator 102. The control system 124 (e.g., the manipulator controller 132 of the robotic control system 126) controls/positions the manipulator 102 in a manner that emulates the way a physical handpiece would respond in the presence of physical boundaries/barriers. The boundary generator 172 may be implemented on the manipulator controller 132. Alternatively, the boundary generator 172 may be implemented on other components, such as the navigation controller 134, or other portions of the control system 124. Other configurations are contemplated.

Figure 25:
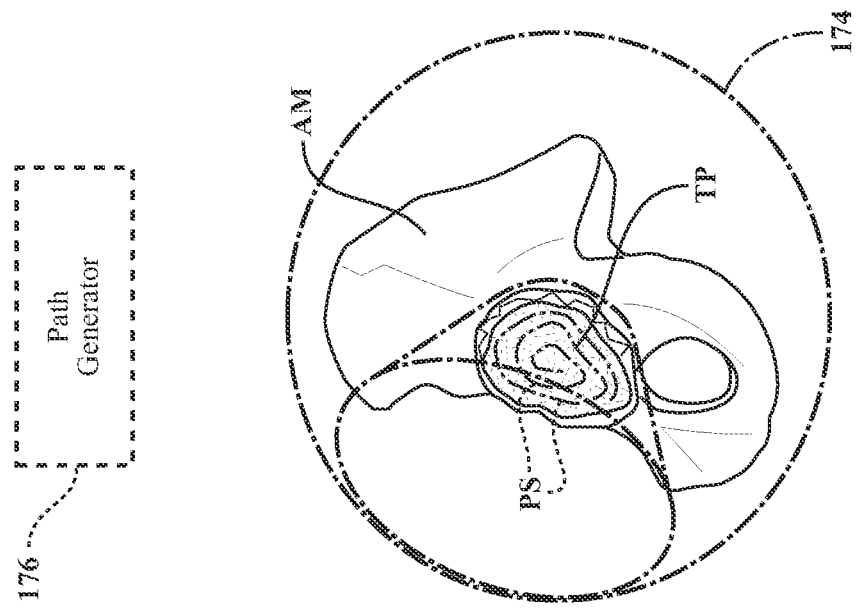
FIG. 25 is an illustrative view of the target site depicting an output of a path generator of the software program of FIG. 23.

Referring to FIG. 23 and FIG. 25, a path generator 176 is another software program or module that may be run by the control system 124. In some embodiments, the path generator 176 is run by the manipulator controller 132. The path generator 176 generates a tool path TP for the tool 104 to traverse, such as for removing sections of the anatomy of the patient P at the target site TS to receive an implantable component 116. The tool path TP may comprise a plurality of path segments PS, or may comprise a single path segment PS. The path segments PS may be straight segments, curved segments, combinations thereof, and the like. The tool path TP may also be defined with respect to the anatomical model AM. The tool path TP may be implant-specific (e.g., defined based on a size, shape, volume, and the like of an implantable component 116) and/or patient-specific (e.g., defined based on the anatomy of the patient P). Other configurations are contemplated.

In some embodiments described herein, the tool path TP is defined as a tissue removal path adjacent to the target site TS. However, in some embodiments, the tool path TP may be used for treatment other than tissue removal. One example of the tissue removal path described herein comprises a tool path TP. It should be understood that the term "tool path" generally refers to the path of the tool 104 in the vicinity of the target site TS for milling the anatomy, and is not intended to require that the tool 104 be operably milling the anatomy throughout the entire duration of the path. For instance, the tool path TP may comprise sections or segments where the tool 104 transitions from one location to another without milling. Additionally, other forms of tissue removal along the tool path TP may be employed, such as tissue ablation, and the like. The tool path TP may be a predefined path that is created pre-operatively, intra-operatively, or combinations thereof. In other words, the tool path TP may be defined before the surgical procedure begins, during the surgical procedure (including during tissue removal), or combinations thereof. In any event, the control system 124 obtains the tool path TP by storing/retrieving the tool path TP in/from memory 140, obtaining the tool path TP from memory 140, creating the tool path TP pre-operatively, creating the tool path TP intra-operatively, and the like. The tool path TP may have any suitable shape, or combinations of shapes, such as circular, helical/corkscrew, linear, curvilinear, combinations thereof, and the like. Other configurations are contemplated.

One example of a system and method for generating the virtual boundaries 174 and/or the tool path TP is described in U.S. Pat. No. 9,119,655, entitled "Surgical Manipulator Capable of Controlling a Surgical Instrument in Multiple Modes," previously referenced. Further examples are described in U.S. Pat. No. 8,010,180, entitled "Haptic Guidance System and Method;" and U.S. Pat. No. 7,831,292, entitled "Guidance System and Method for Surgical Procedures With Improved Feedback," the disclosures of which are each hereby incorporated by reference in their entirety. In some embodiments, the virtual boundaries 174 and/or the milling paths MP may be generated offline rather than on the manipulator controller 132, navigation controller 134, or another component of the surgical system 100. Thereafter, the virtual boundaries 174 and/or milling paths MP may be utilized at runtime by the manipulator controller 132.

Referring back to FIG. 23, another software program or module which may be run on the manipulator controller 132 and/or the navigation controller 134 is shown for performing behavior control 178. Behavior control 178 is the process of computing data that indicates the next commanded position and/or orientation (e.g., pose) for the tool 104. In some cases, only the position or orientation of the tool center point TCP is output from the behavior control 178, while in other cases, the position and the orientation of the tool center point TCP is output from the behavior control 178. In some embodiments, output from the boundary generator 172, the path generator 176, and a sensor 180 (e.g., a six degree of freedom DOF force/torque transducer) may feed as inputs into the behavior control 178 to determine the next commanded position and/or orientation for the tool 104. The behavior control 178 may process these inputs, along with one or more virtual constraints as described in greater detail below, to determine a commanded pose.

With continued reference to FIG. 23, another software program or module which may be run on the manipulator controller 132 and/or the navigation controller 134 is shown for performing motion control 182. One aspect of motion control 182 is the control of the manipulator 102. The motion control 182 receives data defining the next commanded pose from the behavior control 178. Based on these data, the motion control 182 determines the next position of the joint angles of the joints J of the robotic arm 108 of the manipulator 102 (e.g., via inverse kinematics and Jacobian calculators) so that the manipulator 102 is able to position the tool 104 as commanded by the behavior control 178 (e.g., at the commanded pose). In other words, the motion control 182 processes the commanded pose, which may be defined in Cartesian space, into joint angles of the manipulator 102, so that the manipulator controller 132 can command the joint motors accordingly in order to move the joints J of the manipulator 102 to commanded joint angles corresponding to the commanded pose of the tool 104. In some embodiments, the motion control 182 regulates the joint angle of each joint J of the robotic arm 108 and continually adjusts the torque that each joint motor outputs in order to, as closely as possible, ensure that the joint motor drives the associated joint J to the commanded joint angle.

The boundary generator 172, the path generator 176, the behavior control 178, and the motion control 182 may be sub-sets (e.g., modules) of a software program 184. Alternatively, each may be a software program that operates separately and/or independently, or any combination thereof. The term "software program" is used herein to describe the computer-executable instructions that are configured to carry out the various capabilities of the technical solutions described. For simplicity, the term "software program" is intended to encompass, at least, any one or more of the boundary generator 172, the path generator 176, the behavior control 178, and/or the motion control 182. The software program 184 can be implemented on the manipulator controller 132, navigation controller 134, or any combination thereof, or may be implemented in any suitable manner by the control system 124.

In some embodiments, a clinical application 186 may be provided to facilitate user interaction and coordinate the surgical workflow, including pre-operative planning, implant placement, registration, bone preparation visualization, post-operative evaluation of implant fit, and the like. The clinical application 186 may be configured to output data to the output devices 144 (e.g., displays, screens, monitors, and the like), to receive input data from the input devices 146, or to otherwise interact with the user interfaces 142, and may include or form part of a graphical user interface GUI. The clinical application 186 may run on its own separate processor or may run alongside the navigation controller 134, the manipulator controller 132, and/or the tool controller 136, or any other suitable portion of the control system 124. The clinical application 186 can comprise non-transitory memory to store the instructions for implementing the above described automated planning techniques.

In some embodiments, the clinical application 186 interfaces with the boundary generator 172 and/or path generator 176 after implant placement is set by the user, and then sends the virtual boundary 174 and/or the tool path TP returned by the boundary generator 172 and/or the path generator 176 to the manipulator controller 132 for execution. Here, the manipulator controller 132 executes the tool path TP as described herein. The manipulator controller 132 may additionally create certain segments (e.g., lead-in segments) when starting or resuming machining to smoothly get back to the generated tool path TP. The manipulator controller 132 may also process the virtual boundaries 174 to generate corresponding virtual constraints as described in greater detail below.

The surgical system 100 may operate in a manual mode, such as described in U.S. Pat. No. 9,119,655, entitled "Surgical Manipulator Capable of Controlling a Surgical Instrument in Multiple Modes," previously referenced. Here, the user manually directs, and the manipulator 102 executes movement of the tool 104 and its energy applicator 114 at the surgical site. The user (e.g., the surgeon) physically contacts the tool 104 to cause movement of the tool 104 in the manual mode. In some embodiments, the manipulator 102 monitors forces and torques placed on the tool 104 by the user in order to position the tool 104. To this end, the surgical system 100 may employ the sensor 180 (e.g., a multiple degree of freedom DOF force/torque transducer) that detects and measures the forces and torques applied by the user to the tool 104 and generates corresponding input used by the control system 124 (e.g., one or more corresponding input/output signals). The forces and torques applied by the user at least partially define an external force $F_{ext}$ that is used to determine how to move the tool 104 in the manual mode (or other modes). The external force $F_{ext}$ may comprise other forces and torques, aside from those applied by the user, such as gravity-compensating forces, backdrive forces, and the like, as described in U.S. Pat. No. 9,119,655, entitled "Surgical Manipulator Capable of Controlling a Surgical Instrument in Multiple Modes," previously referenced. Thus, the forces and torques applied by the user at least partially define the external force $F_{ext}$, and in some cases may fully define the external force $F_{ext}$ that influences overall movement of the tool 104 in the manual mode and/or in other modes as described in greater detail below.

The sensor 180 may comprise a six degree of freedom DOF force/torque transducer arranged to detect forces and/or torque occurring between the manipulator 102 and the target site TS (e.g., forces applied to the tool 104 by the user). For illustrative purposes, the sensor 180 is generically-depicted adjacent to or otherwise as a part of the coupling 110 of the manipulator 102 (e.g., coupled to joint J6 of the robotic arm 108). However, other configurations and arrangements are contemplated. The manipulator controller 132, the navigation controller 134, the tool controller 136, and/or other components of the surgical system 100 may receive signals (e.g., as inputs) from the sensor 180. In response to the user-applied forces and torques, the manipulator 102 moves the tool 104 in a manner that emulates the movement that would have occurred based on the forces and torques applied by the user. Movement of the tool 104 in the manual mode may also be constrained in relation to the virtual boundaries 174 generated by the boundary generator 172. In some embodiments, measurements taken by the sensor 180 are transformed from a sensor coordinate system SN of the sensor 180 to another coordinate system, such as a virtual mass coordinate system VM, in which a virtual simulation VS is carried out on a virtual rigid body VRB model of the tool 104 so that the forces and torques can be virtually applied to the virtual rigid body VRB in the virtual simulation VS to ultimately determine how those forces and torques (among other inputs) would affect movement of the virtual rigid body VRB, as described below.

The surgical system 100 may also operate in a semi-autonomous mode in which the manipulator 102 autonomously moves the tool 104 along the tool path TP, such as by operating active joints J of the manipulator 102 to move the tool 104 without requiring force/torque on the tool 104 from the user. Examples of operation in the semi-autonomous mode are also described in U.S. Pat. No. 9,119,655, entitled "Surgical Manipulator Capable of Controlling a Surgical Instrument in Multiple Modes," previously referenced. In some embodiments, when the manipulator 102 operates in the semi-autonomous mode, the manipulator 102 is capable of moving the tool 104 free of user assistance. Here, "free of user assistance" may mean that the user does not physically contact the tool 104 or the robotic arm 108 to move the tool 104. Instead, the user may use some form of remote control (e.g., a pendant; not shown) to control starting and stopping of movement. For example, the user may hold down a button of the remote control to start movement of the tool 104 and release the button to stop movement of the tool 104. Examples of this type of remote control embodied in user pendant are described in U.S. Pat. No. 10,117,713, entitled "Robotic Systems and Methods for Controlling a Tool Removing Material from Workpiece," the disclosure of which is hereby incorporated herein by reference in its entirety. Other configurations are contemplated.

In the manual mode, it may be challenging for the user to move the tool 104 from a current state to a target state (e.g., to a target position, a target orientation, or a target pose). It may be desirable for the tool 104 to be moved to a particular target state for any number of reasons, such as to place the tool 104 in a desired proximity to the tool path TP, to place the tool 104 at an orientation suitable for preparing tissue to receive an implantable component 116, for aligning the tool 104 with a particular trajectory/plane, and the like. However, it may be difficult for the user to place the tool 104 with sufficient precision. This can be especially difficult when the anatomy of the patient P is partially obstructed from the user's view by soft tissue, fluids, and the like. Here, the surgical system 100 may be switched from the manual mode to the semi-autonomous mode, such as in the manner described in U.S. Pat. No. 9,119,655, entitled "Surgical Manipulator Capable of Controlling a Surgical Instrument in Multiple Modes," previously referenced. Accordingly, to place the tool 104 at the target state, the manipulator 102 may autonomously move the tool 104 from the current state to the target state.

Several examples have been discussed in the foregoing description. However, the examples discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A computer-implemented method for operating a surgical system to facilitate removal of a diseased region of an anatomy, wherein the surgical system comprises a surgical tool, a navigation system comprising a localizer configured to track the surgical tool and the anatomy, and a control system coupled to the surgical tool and the navigation system and the control system implementing a boundary generator, the computer-implemented method comprising:
performing, with the control system and the boundary generator, an automated planning of a virtual cutting boundary by:
obtaining a virtual model of the diseased region;
defining, relative to the virtual model of the diseased region, a first plane and a second plane being spaced apart from the first plane;
identifying a geometrical feature of the virtual model of the diseased region;
providing a first reference spline derived from the geometrical feature onto the first plane;
providing a second reference spline derived from the geometrical feature onto the second plane;
creating a first set of ruled surfaces extending between the reference splines;
optimizing a shape of one or both of the reference splines to thereby define one or both of an optimized first spline and an optimized second spline, wherein optimizing is based on minimizing a volume bounded by the first set of ruled surfaces and the first and second planes;
creating a second set of ruled surfaces extending between one of the reference splines and one of the optimized splines or extending between the optimized splines; and
defining the virtual cutting boundary based on the second set of ruled surfaces;
registering, with the navigation system, the virtual cutting boundary to the anatomy; and
controlling, with the control system, operation of the surgical tool to facilitate removal of the diseased region by utilizing the registered virtual cutting boundary for constraining movement and/or operation of the surgical tool in response to the surgical tool interacting with the registered virtual cutting boundary.

2. The computer-implemented method of claim 1, comprising:
obtaining a primary axis along which to evaluate the diseased region in a coordinate system of the virtual model of the diseased region; and
wherein obtaining the primary axis occurs by:
receiving input of primary axis based on surgical plan or surgeon preference; or
automatically determining the primary axis based on evaluation of the virtual model of the diseased region.

3. The computer-implemented method of claim 2, comprising:
identifying one or more boundaries of the virtual model of the diseased region relative to the primary axis; and
defining one or both of the first or second planes at or beyond one of the boundaries of the virtual model of the diseased region.

4. The computer-implemented method of claim 2, comprising:
defining the first and second planes to be parallel to one another; and
defining the first and second planes to intersect the primary axis.

5. The computer-implemented method of claim 2, wherein the geometrical feature is a contour of the virtual model of the diseased region and comprising projecting the contour along the primary axis onto one or both planes to define one or both reference splines wherein one or both reference splines has a contour being congruent to the contour of the diseased region.

6. The computer-implemented method of claim 2, comprising:
defining a third plane above the second set of ruled surfaces with reference to the primary axis;
extending the second set of ruled surfaces to the third plane;

defining a fourth plane below the second set of ruled surfaces with reference to the primary axis; and
extending the second set of ruled surfaces to the fourth plane.

7. The computer-implemented method of claim 6, further utilizing a virtual model of a healthy region of the anatomy adjacent to the diseased region, and the method comprising:
identifying an uppermost reference and a lowermost reference of the virtual model of the healthy region relative to the primary axis;
defining the third plane at or above the uppermost reference of the virtual model of the healthy region; and
defining the fourth plane at or below the lowermost reference of the virtual model of the healthy region.

8. The computer-implemented method of claim 7, comprising:
identifying locations of intersections among the second set of ruled surfaces occurring from extending the second set of ruled surfaces to the fourth plane;
defining an intersection reference geometry based on the identified locations of intersections; and
defining the virtual cutting boundary based on the second set of ruled surfaces extending between the third plane and the intersection reference geometry.

9. The computer-implemented method of claim 1, further utilizing a virtual model of a healthy region of the anatomy adjacent to the diseased region, and the method comprising:
minimizing the volume by minimizing a volume of the healthy region bounded by the first set of ruled surfaces and the first and second planes.

10. The computer-implemented method of claim 1, further comprising optimizing a shape of one or both reference splines or one or both optimized splines by:
determining that one or more ruled surfaces intersects the virtual model of the diseased region; and
adjusting position and/or orientation of the one or more of the ruled surfaces to not intersect the virtual model of the diseased region.

11. The computer-implemented method of claim 1, wherein optimizing a shape of one or both reference splines comprises:
obtaining an access angle defining planned access angle of the diseased region by a surgical tool; and
adjusting position and/or orientation of the one or more of the ruled surfaces of the first set to not exceed the access angle thereby adjusting the shape of one or both reference splines.

12. The computer-implemented method of claim 1, further utilizing a virtual model of healthy anatomy adjacent to the diseased region, and comprising optimizing a shape of one or both reference splines by:
identifying, with respect to the virtual model of healthy anatomy, one or more virtual boundaries defining regions to be avoided by a surgical tool; and
adjusting position and/or orientation of the one or more of the ruled surfaces of the first set to not intersect any of the one or more of virtual boundaries thereby adjusting the shape of one or both reference splines.

13. The computer-implemented method of claim 1, comprising: defining the first or second plane to intersect the virtual model of the diseased region.

14. The computer-implemented method of claim 1, wherein the geometrical feature is one or more of the following features of the virtual model of the diseased region: a contour, an outermost contour, a cross-sectional area, a cross-sectional perimeter, a volume, an area, a surface area, a shape, a size, a length, a width, a height, a perimeter, vertices, a diameter or radius, an arc, a tangent, an angle, a mass, a center of gravity, a center of mass, and a centroid.

15. The computer-implemented method of claim 1, comprising:
defining points along the first reference spline to define a first reference point set;
defining points along the second reference spline to define a second reference point set; and
creating the first set of ruled surfaces such that each ruled surface of the first set has vertices defined by adjacent points in the first reference point set and adjacent points in the second reference point set.

16. The computer-implemented method of claim 15, comprising:
defining points along one or both of the optimized splines to define one or both first and second optimized point sets; and
creating the second set of ruled surfaces such that each ruled surface of the second set has vertices defined by:
adjacent points in one optimized point set and adjacent points in one reference point set; or
adjacent points in the first optimized point set and adjacent points in the second optimized point set.

* * * * *